US010792365B2

(12) United States Patent
Nishio et al.

(10) Patent No.: US 10,792,365 B2
(45) Date of Patent: Oct. 6, 2020

(54) PEPTIDE DERIVATIVE AND USE THEREOF

(71) Applicant: Toray Industries, Inc., Tokyo (JP)

(72) Inventors: Yukihiro Nishio, Kamakura (JP);
Shinya Yokosaka, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 243 days.

(21) Appl. No.: 16/084,994

(22) PCT Filed: Mar. 29, 2017

(86) PCT No.: PCT/JP2017/012797
§ 371 (c)(1),
(2) Date: Sep. 14, 2018

(87) PCT Pub. No.: WO2017/170637
PCT Pub. Date: Oct. 5, 2017

(65) Prior Publication Data
US 2019/0038757 A1 Feb. 7, 2019

(30) Foreign Application Priority Data

Mar. 29, 2016 (JP) ................................. 2016-065737

(51) Int. Cl.
| | |
|---|---|
| *A61K 47/42* | (2017.01) |
| *A61K 47/34* | (2017.01) |
| *A61P 31/00* | (2006.01) |
| *A61P 37/06* | (2006.01) |
| *A61P 35/00* | (2006.01) |
| *C07K 5/02* | (2006.01) |
| *C07K 14/435* | (2006.01) |

(52) U.S. Cl.
CPC .............. *A61K 47/42* (2013.01); *A61K 47/34* (2013.01); *A61P 31/00* (2018.01); *A61P 35/00* (2018.01); *A61P 37/06* (2018.01); *C07K 5/02* (2013.01); *C07K 14/43504* (2013.01)

(58) Field of Classification Search
CPC ......... A61K 47/42; A61K 47/34; A61P 31/00; A61P 37/06; A61P 35/00; C07K 5/02; C07K 14/43504
See application file for complete search history.

(56) References Cited

U.S. PATENT DOCUMENTS

| 4,816,444 A | 3/1989 | Pettit et al. | |
|---|---|---|---|
| 2017/0095525 A1* | 4/2017 | Papot | A61K 47/60 |

FOREIGN PATENT DOCUMENTS

| EP | 0 598 129 A1 | 5/1994 |
|---|---|---|
| JP | H02-167278 A | 6/1990 |
| WO | 93/03054 A1 | 2/1993 |
| WO | 95/09864 A1 | 4/1995 |
| WO | 02/088172 A2 | 11/2002 |
| WO | 2004/010957 A2 | 2/2004 |
| WO | 2012/171020 A1 | 12/2012 |
| WO | 2013/173393 A1 | 11/2013 |
| WO | 2014/086952 A1 | 6/2014 |
| WO | 2015/113760 A1 | 8/2015 |
| WO | 2015/118497 A1 | 8/2015 |

OTHER PUBLICATIONS

K. Miyazaki et al., "Synthesis of dolastatin 10 analogs", Peptide Chemistry, 1993: Y.Okade (Ed.), pp. 85-88.
The Extended European Search Report dated Nov. 18, 2019, of counterpart European Application No. 17775174.0.
George R. Pettit et al., "The isolation and structure of a remarkable marine animal antineoplastic constituent: dolastatin 10," Journal of the American Chemical Society, vol. 109 (22), 1987, pp. 6883-6885 (Abstract only).
Koichi Miyazaki et al., "Synthesis and Antitumor Activity of Novel Dolastatin 10 Analogs," Chemical and Pharmaceutical Bulletin, vol. 43 (10), 1995, pp. 1706-1718.
Svetlana O. Doronina et al., "Novel Peptide Linkers for Highly Potent Antibody-Auristatin Conjugate," Bioconjugate Chemistry, vol. 19 (10), 2008, pp. 1960-1963 (Abstract only).
Jun Y. Axup et al., "Synthesis of site-specific antibody-drug conjugates using unnatural amino acids," PNAS, vol. 109, No. 40, 2012, pp. 16101-16106.
Pamela A. Trail, "Antibody Drug Conjugates as Cancer Therapeutics," Antibodies, vol. 2 (1), 2013, pp. 113-129 (Abstract only).
Andreas Maderna et al., "Discovery of Cytotoxic Dolastatin 10 Analogues with N-Terminal Modifications," Journal of Medicinal Chemistry, vol. 57 (24), 2014, pp. 10527-10543 (Abstract only).
Michael P. VanBrunt et al., "Genetically Encoded Azide Containing Amino Acid in Mammalian Cells Enables Site-Specific Antibody-Drug Conjugates Using Click Cycloaddition Chemistry," Bioconjugate Chemistry, vol. 26 (11), 2015, pp. 2249-2260 (Abstract only).
Nareshkumar Jain et al., "Current ADC Linker Chemistry," Pharmaceutical Research, vol. 32, 2015, pp. 3526-3540.
Jeffrey C. Kern et al., "Discovery of Pyrophosphate Diesters as Tunable, Soluble, and Bioorthogonal Linkers for Site-Specific Antibody-Drug Conjugates," Journal of the American Chemical Society, vol. 138 (4), 2016, pp. 1430-1445 (Abstract only).

* cited by examiner

*Primary Examiner* — Timothy R Rozof
(74) *Attorney, Agent, or Firm* — DLA Piper LLP (US)

(57) ABSTRACT

A peptide derivative represented by Formula (I) or a pharmaceutically acceptable salt thereof:

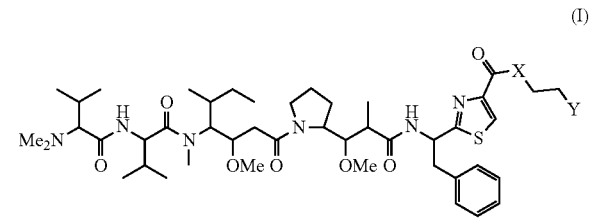

(I)

wherein X represents an oxygen atom or NR, Y represents $NH_2$, N(Me)H, SH, OH, or phenyl in which any one of hydrogen atoms is replaced by $NH_2$ or OH, and R represents a hydrogen atom or $C_1$-$C_3$ alkyl, provided that the derivative where X is NH, and Y is $NH_2$, and the derivative where X is NH, and Y is N(Me)H are excluded.

19 Claims, No Drawings

PEPTIDE DERIVATIVE AND USE THEREOF

TECHNICAL FIELD

This disclosure relates to a peptide derivative and use thereof.

BACKGROUND

A plurality kinds of cytotoxic peptide derivatives have been isolated from *Dolabella auricularia* inhabiting the ocean. As a compound that is a type of those peptide derivatives and has extremely high cytotoxicity, Dolastatin 10 is known (JP 02-167278 A and Pettil et al., Journal of the American Chemical Society (1987) 109, pp 6883-6885).

It has been shown that the cytotoxicity of Dolastatin 10 is exerted by a tubulin polymerization inhibitory action and, to date, the structure activity relationships thereof have been reported (WO 1993/003054 and WO 1995/009864, and Miyazaki et al., Chemical and Pharmaceutical Bulletin (1995) 43, pp 1706-1718). Moreover, as another similar peptide derivative having the tubulin polymerization inhibitory action, there is monomethyl auristatin (WO 2002/088172 and WO 2004/010957). It is known that this compound is utilized for an antibody-drug conjugate in which the compound is bound to a specified amino acid of an antibody via a specified structure referred to as a linker.

Pharmaceutical products available for the antibody-drug conjugate need to have a specified substituent (e.g., amino, sulfhydryl, or hydroxy group) capable of binding to the linker or the antibody. Furthermore, medical efficacy of the conjugate is greatly affected by its binding manner, and the uses of a plurality kinds of substituents have been reported to date (Jain et al., Pharmaceutical Research (2015) 32, pp 3526-3540, Trais et al., Antibodies (2013) 2, pp 113-129, and Kern et al., Journal of the American Chemical Society (2016) 138, pp 1430-1445).

As the derivatives having the functional groups available for the conjugates among the tubulin inhibitors, monomethyl auristatin above or PF-063801010 that has an amino group at N-terminus (Maerna et al., Journal of Medicinal Chemical Society (2014) 57, pp 10527-43), or auristatin F derivatives that have an amino group, hydroxy group, carboxylic acid, hydroxylamine, or alkyne at C-terminus (WO) 2012/171020 and Doronia et al., Bioconjugate Chemistry (2008), 19, pp 1960-1963, Axup et al., Proceedings of the National Academy of Sciences (2012) 109, pp 16101-16106, and Van Brunt et al., Bioconjugate Chemistry (2015) 26, pp 2249-2260) have been reported to date.

Meanwhile, for developments from C-terminus of Dolastatin 10, a derivative that has ethyl ester, ethyl amide, or thiazole amide has been reported (Miyazaki et al., Peptide Chemistry (1993), pp 85-88).

However, the Dolastatin 10 derivatives that have a functional group available for formation of the conjugate at C-terminus have not been reported to date.

Furthermore, it is considered that the derivatives having the same skeleton but having different types of substituents are useful for the creation of a novel conjugate and verifying effect of the conjugate's composition on the cytotoxicity. However, such derivatives have not been reported.

It could therefore be helpful to provide a Dolastatin 10 derivative having a functional group(s) available for formation of a conjugate at C-terminus.

SUMMARY

We found that a novel peptide derivative with a specified functional group at C-terminus or a pharmaceutically acceptable salt thereof has high cytotoxicity on a plurality of cancer cells.

We thus provide:

A peptide derivative represented by Formula (I) or a pharmaceutically acceptable salt thereof:

(I)

wherein X represents an oxygen atom or NR, Y represents $NH_2$, N(Me)H, SH, OH, or phenyl in which any one of hydrogen atoms is replaced by $NH_2$ or OH, and R represents a hydrogen atom or $C_1$-$C_3$ alkyl, provided that the derivative where X is NH, and Y is $NH_2$, and the derivative where X is NH, and Y is N(Me)H are excluded.

In the peptide derivative represented by Formula (I) or a pharmaceutically acceptable salt thereof, X is preferably an oxygen atom.

In this case, high cytotoxicity can be expected.

In the peptide derivative represented by Formula (I) or a pharmaceutically acceptable salt thereof, more preferably, X is an oxygen atom, and Y is $NH_2$, N(Me)H, SH, or OH.

In this case, higher cytotoxicity can be expected.

In the peptide derivative represented by Formula (I) or a pharmaceutically acceptable salt thereof, X is preferably NR.

In this case, higher cytotoxicity can be expected.

In the peptide derivative represented by Formula (I) or a pharmaceutically acceptable salt thereof, more preferably, X is NR, and R is $C_1$-$C_3$ alkyl.

In this case, higher cytotoxicity can be expected.

In the peptide derivative represented by Formula (I) or a pharmaceutically acceptable salt thereof, still more preferably, X is NR, and R is methyl.

In this case, still higher cytotoxicity can be expected.

Furthermore, we provide a conjugate or a pharmaceutically acceptable salt thereof that includes the peptide derivative represented by Formula (I) and a targeting ligand or a polymer.

Furthermore, we provide a cytotoxic agent including, as an active ingredient, the peptide derivative represented by Formula (I) or a pharmaceutically acceptable salt thereof, or the conjugate or a pharmaceutically acceptable salt thereof.

Our peptide derivatives or pharmaceutically acceptable salts thereof have high cytotoxicity and therefore can be used as cytotoxic agents.

Furthermore, our peptide derivatives have various functional groups at C-terminus. Therefore, the peptide derivative or a prodrug thereof, and a targeting ligand or a polymer can be conjugated. The resultant conjugates or pharmaceutically acceptable salts thereof can be used as cytotoxic agents.

DETAILED DESCRIPTION

Our peptide derivative is characteristically represented by Formula (I):

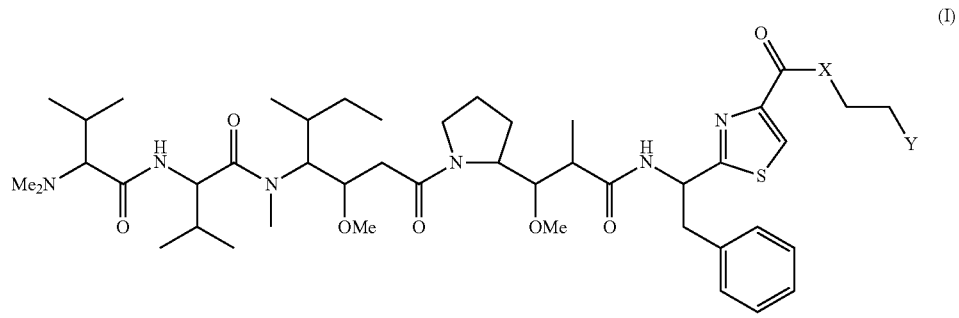

(I)

wherein X represents an oxygen atom or NR, Y represents NH₂, N(Me)H, SH, OH, or phenyl in which any one of hydrogen atoms is replaced by NH₂ or OH, and R represents a hydrogen atom or $C_1$-$C_3$ alkyl, provided that the derivative where X is NH, and Y is NH₂, and the derivative where X is NH, and Y is N(Me)H are excluded.

Unless otherwise specified, the following terms used herein are as defined below.

The term "phenyl in which any one of hydrogen atoms is replaced by NH₂ or OH" means 2-aminophenyl, 3-aminophenyl, 4-aminophenyl, 2-hydroxyphenyl, 3-hydroxyphenyl, or 4-hydroxyphenyl.

The term "$C_1$-$C_3$ alkyl" means methyl, ethyl, propyl, or isopropyl.

Specific examples of preferable compounds of the peptide derivatives represented by Formula (I) are indicated in Table 1, but this disclosure is not limited thereto.

TABLE 1

Structural Formula

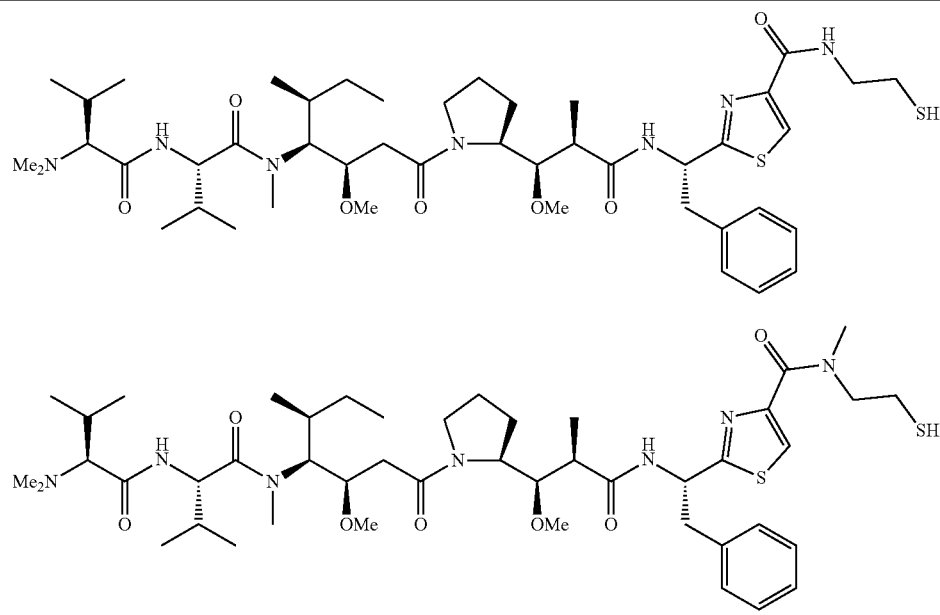

TABLE 1-continued
Structural Formula
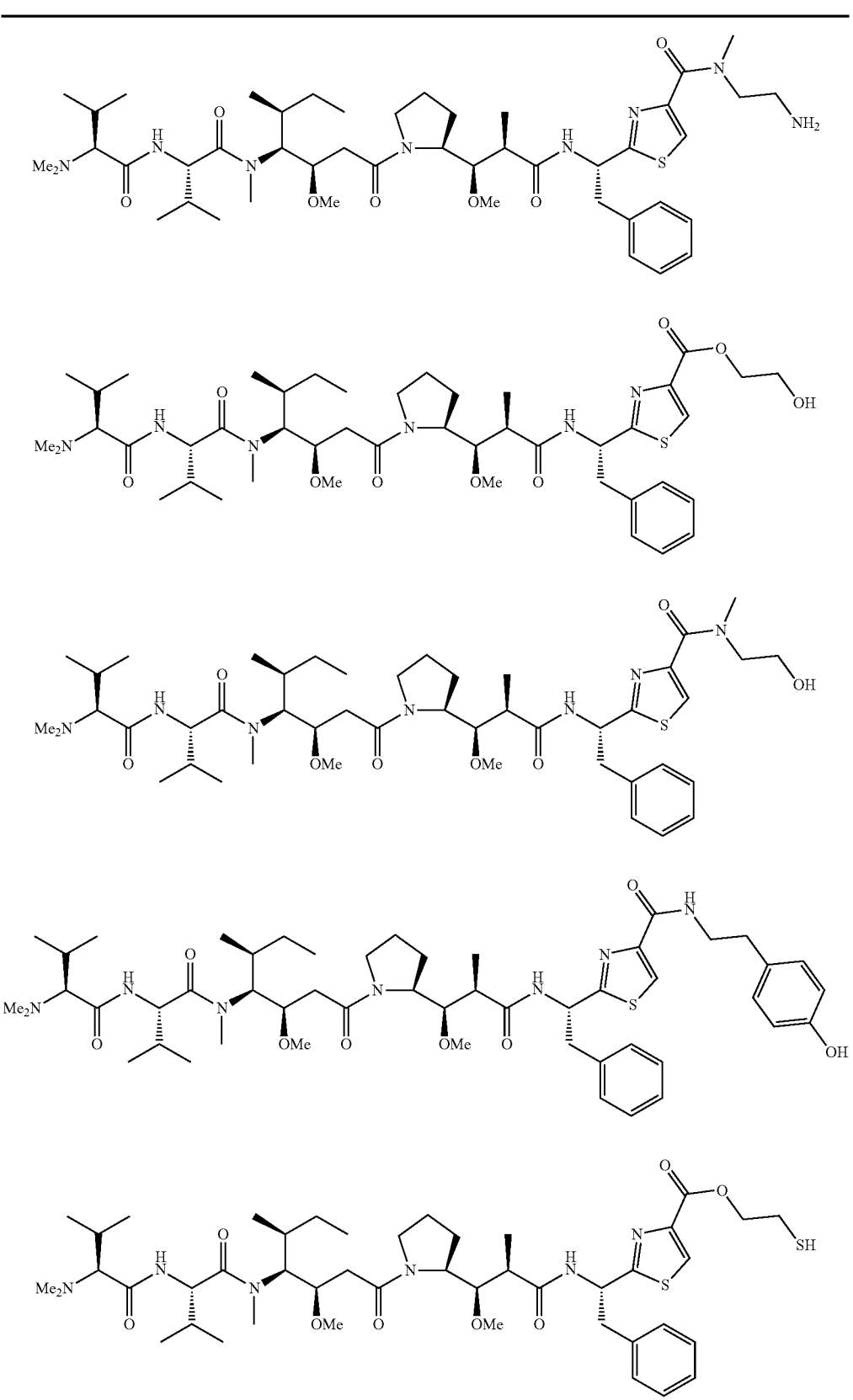

TABLE 1-continued

Structural Formula

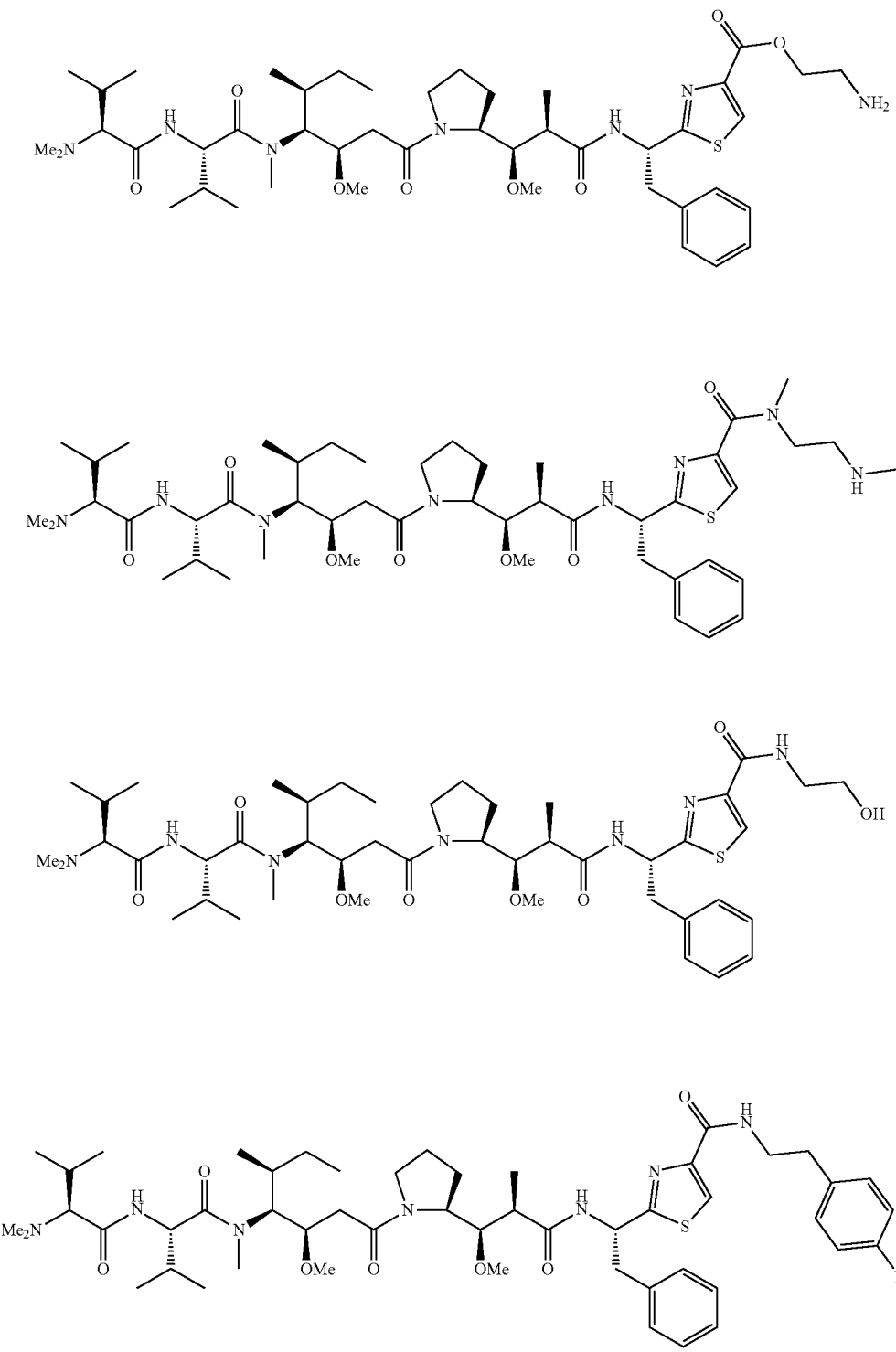

The compounds described in Table 1 also include pharmaceutically acceptable salts thereof.

When the peptide derivative represented by Formula (I) (hereinafter, peptide derivative (I)) contains conformational isomers, rotational isomers, tautomers, optical isomers, diastereomers, epimers or the like, the peptide derivative (I) also includes any one of the isomers as well as mixture thereof. In addition, when optical isomers of the peptide derivative (I) exist, an optical isomer obtained by resolution of racemate is included in the peptide derivative (I).

The configuration of the peptide derivative (I) is preferably Formula (II):

(II)

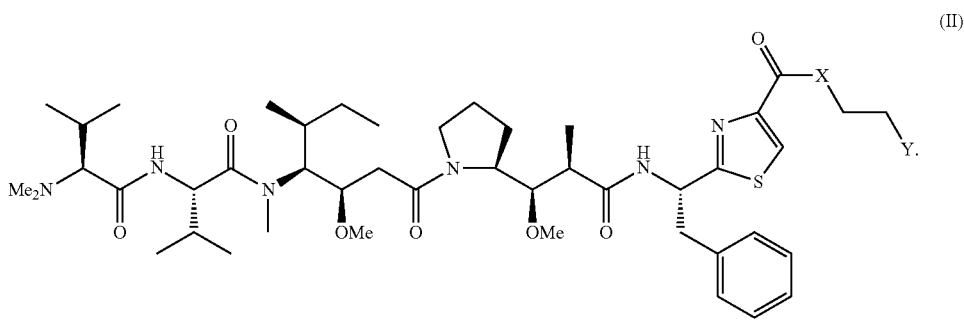

We also provide a prodrug of the peptide derivative (I) or a pharmaceutically acceptable salt thereof. The prodrug of the peptide derivative (I) refers to a compound which is enzymatically or chemically converted in vivo to the peptide derivative (I). The activity of a prodrug of the peptide derivative (I) is attributable to the peptide derivative (I) but the prodrug of the peptide derivative (I) itself may have some activity.

Examples of the prodrug of the peptide derivative (I) include compounds in which the hydroxy group of the peptide derivative (I) is esterified, carbonated, carbamated, alkylated, phosphorylated, or borated. These compounds can be synthesized from the peptide derivative (I) or a synthetic intermediate thereof according to known methods.

Examples of the prodrug of the peptide derivative (I) include compounds in which the amino group of the peptide derivative (I) is carbamated or amidated. These compounds can be synthesized from the peptide derivative (I) or a synthetic intermediate thereof according to known methods.

Examples of the prodrug of the peptide derivative (I) include compounds in which the sulfhydryl group of the peptide derivative (I) forms the disulfide bond. These compounds can be synthesized from the peptide derivative (I) or a synthetic intermediate thereof according to known methods.

Specific examples of the prodrugs of the peptide derivative (I) above are indicated in Table 2, but this disclosure is not limited thereto.

TABLE 2

| Number | Structural Formula |
|---|---|
| 1 | 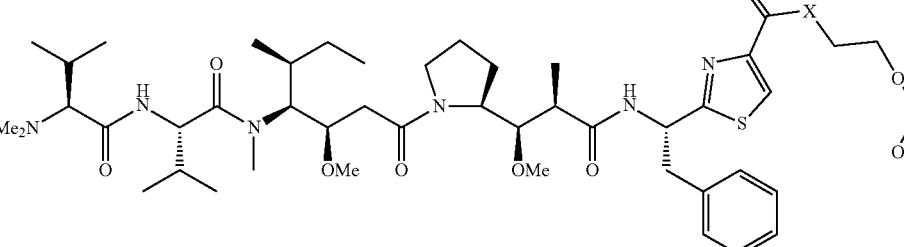 |
| 2 | 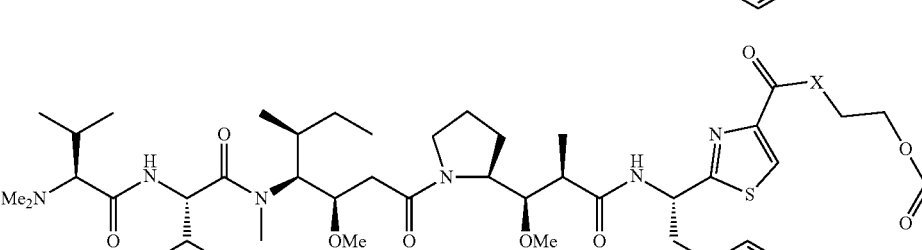 |
| 3 | 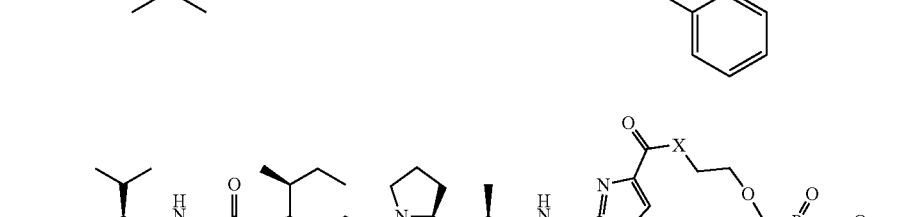 |

TABLE 2-continued

| Number | Structural Formula |
|---|---|
| 4 |  |
| 5 |  |
| 6 |  |
| 7 |  |
| 8 |  |
| 9 |  |

TABLE 2-continued

| Number | Structural Formula |
|---|---|
| 10 | 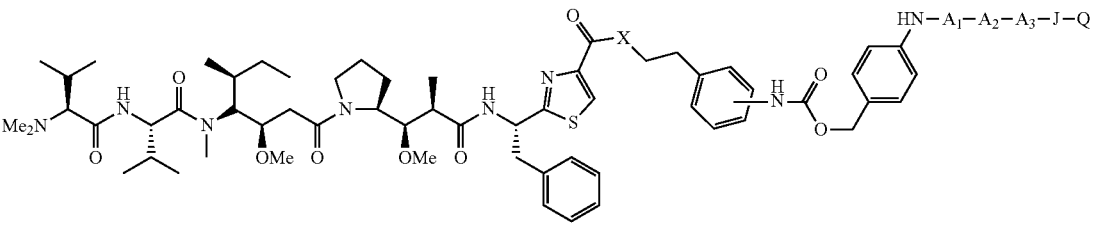 |
| 11 | 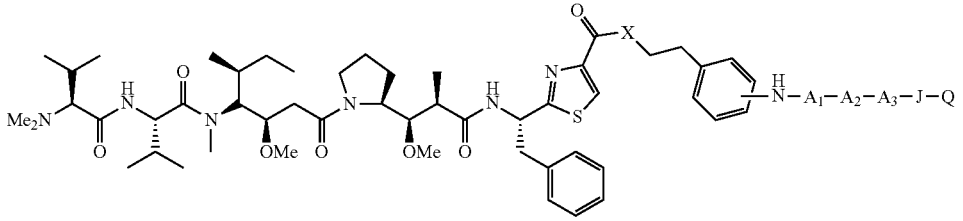 |

The compounds described in Table 2 also include salts thereof.

In Table 2, each Q represents a functional group (e.g., maleimide, carboxyl, activated carboxyl, carbonyl, aminooxy, hydrazide, diazo, alkyne, or hydroxy group) that is capable of conjugation by known methods (e.g., Ellen M. Sletten et al., Angewante Chimie International Edition, (2009), 48: pp. 6974-6998; Greg T. Hermanson, "Bioconjugate Technique," Elsevier; Xi Chem et al., Organic & Biomolecular Chemistry, (2016), 14: pp. 5417-5439) or equivalent methods thereto; J is absent or represents a spacer; $A_1$, $A_2$, and $A_3$ represent amino acids; Z represents a hydrogen atom or methyl group; and other symbols are the same as the definition above.

The term "spacer" means a structure that binds the peptide derivative (I) or the prodrug of the peptide derivative (I) with Q. Examples of the spacer include linear-chain or branched $C_1$-$C_{12}$ alkyl, —C(=O)N(Z)— or —N(Z)C(=O)—, PEGs, disulfide bonds, or structures constituted by any combination of the foregoing, and preferably include the structures constituted by any combination of the foregoing.

Examples of the term "linear-chain or branched $C_1$-$C_{12}$ alkyl" include —$(CH_2)_n$—, —CH(Me)-, —C(Me)$_2$-, —$(CH_2)_o$CH(Me)-, —CH(Me)$(CH_2)_o$—, —$(CH_2)_p$C(Me)$_2$-, or —C(Me)$_2$$(CH_2)_p$—. The n represents an integer of 1 to 12, o represents an integer of 1 to 10, and p represents an integer of 1 to 9.

The term "PEG" means a linear-chain polyethylene glycol that is represented by a repetitive structure of —$(CH_2CH_2O)_m$— and has number-average molecular weight of 200 to 2,000, where m represents an integer of 5 to 45.

When the amino acid and the like are indicated by abbreviations herein, the abbreviations are based on the abbreviations from IUPAC-IUB Commission on Biochemical Nomenclature, or common abbreviations in the art, and examples of the abbreviation will be describe below. Furthermore, when an optical isomer may be present for the amino acid, unless specified to the contrary, if not defined, it is assumed that the amino acid indicates L-form thereof (e.g., "Lys" means Lys in L-form). When indicated by "D-," the amino acid indicates D-form thereof (e.g., "D-Lys" means Lys in D-form). When indicated by "DL-," the amino acid indicates D-form and L-form racemate (e.g., "DL-Lys" means the racemate of Lys in D-form and Lys in L-form).

The "amino acid" is any one selected from DL-Ala, DL-Arg, DL-Asn, DL-Asp, DL-Cit, DL-Cys, DL-Gln, DL-Glu, DL-Gly, DL-His, DL-Ile, DL-Leu, DL-Lys, DL-Met, DL-Phe, DL-Pro, DL-Ser, DL-Thr, DL-Trp, DL-Tyr, or DL-Val. Preferably, $A_1$ is Lys, and $A_2$ and $A_3$ are absent; $A_1$ is Cit or Lys, $A_2$ is Val or Phe, and $A_3$ is absent; or $A_1$ is Asp, and $A_2$ and $A_3$ is Ala.

$A_1$ described in Table 2 is bound to NH in the phenyl group at a carbonyl terminus, and $A_1$, $A_2$, and $A_3$ are bound via amide bonds in the main chain.

In Table 3, preferable structures of the prodrug of the peptide derivative (I) described as Number 6 in Table 2 are illustrated, but this disclosure is not limited thereto.

TABLE 3

Structural Formula

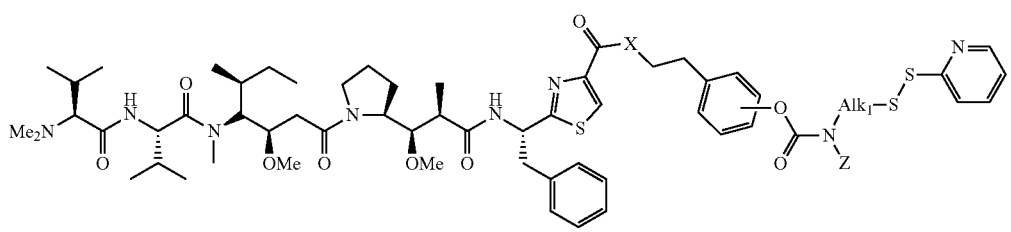

TABLE 3-continued

Structural Formula

[Three chemical structural formulas showing peptide derivatives with thiazole-containing linkers]

The compounds described in Table 3 also include salts thereof.

In Table 3, $Alk_1$ and $Alk_2$ independently represent linear-chain or branched $C_1$-$C_{12}$ alkyl; E is absent or represents —C(=O)N(Z)— or —N(Z)C(=O)—; and other symbols are the same as the definition above.

In the prodrugs of the peptide derivatives (I) described in Table 3, more preferably $Alk_1$ is —$(CH_2)_2$—, and still more preferably X is NR, $Alk_1$ is —$(CH_2)_2$—, E is —N(Z)C(=O)—, PEG is —$(CH_2CH_2O)_{12}$—, and Q is maleimide, but this disclosure is not limited thereto.

In the prodrug of the peptide derivatives (I) described as Number 8 in Table 2, preferably J is -$Alk_1$-E-$Alk_2$- or -$Alk_1$-E-PEG-$(CH_2)_2$-E-$Alk_2$-, and more preferably J is —$(CH_2)_2$—N(Z)C(=O)-$Alk_2$- or —$(CH_2)_2$—N(Z)C(=O)—$(CH_2CH_2O)_{12}$—$(CH_2)_2$—N(Z)C(=O)-$Alk_2$-, and Q is maleimide, but this disclosure is not limited thereto.

In the prodrugs of the peptide derivatives (I) described as Numbers 9 to 11 in Table 2, preferably J is —C(=O)-$Alk_1$-, —C(=O)—PEG-$(CH_2)_2$-E-$Alk_1$-, or —C(=O)-$Alk_1$-E-PEG-$(CH_2)_2$-E-$Alk_1$-, and more preferably J is —C(=O)—$(CH_2)_n$—, —C(=O)—PEG-$(CH_2)_2$-E-$(CH_2)_n$—, or —C(=O)—$(CH_2)_n$-E-PEG-$(CH_2)_2$-E-$(CH_2)_n$—, $A_1$ is Cit or Lys, $A_2$ is Val or Phe, $A_3$ is absent, and Q is maleimide or aminooxy, but this disclosure is not limited thereto.

Moreover, the prodrug of the peptide derivative (I) may be a prodrug converted to the peptide derivative (I) under the physiological conditions described in "Development of Pharmaceutical Product," Hirokawa Shoten Co., (1990), Vol. 7, pp. 163-198; and Progress in Medicine, (1985), Vol. 5, pp. 2157-2161.

The peptide derivative (I) may be labeled with an isotope, and examples of the isotope used for labeling include $^2H$, $^3H$, $^{13}C$, $^{14}C$, $^{15}N$, $^{15}O$, $^{17}O$, $^{18}O$ and/or $^{125}I$.

Examples of "pharmaceutically acceptable salt" of the peptide derivative (I) include inorganic acid salts such as hydrochloride, sulfate, nitrate, hydrobromide, hydroiodide, or phosphate; or organic acid salts such as oxalate, malonate, citrate, fumarate, lactate, malate, succinate, tartrate, acetate, trifluoroacetate, maleate, gluconate, benzoate, ascorbate, glutarate, mandelate, phthalate, methanesulfonate, ethanesulfonate, benzenesulfonate, p-toluenesulfonate, camphorsulfonate, aspartate, glutamate, or cinnamate, and preferably include a hydrochloride, sulfate, hydrobromide, maleate, benzoate, or methanesulfonate.

The peptide derivative (I) or a pharmaceutically acceptable salt thereof may be an anhydrate or may have formed a solvate such as hydrate. The solvate herein is preferably a pharmaceutically acceptable solvate. The pharmaceutically acceptable solvate may be any of a hydrate and non-hydrate, but preferably it is a hydrate. Examples of the solvent constituent in the solvate include alcohol-based solvents such as methanol, ethanol, or n-propanol; N,N-dimethylformamide; dimethyl sulfoxide; or water.

The peptide derivative (I) can be produced by an appropriate method based on its basic structure and features derived from the types of substituents. In addition, the starting materials and reagents used for the production of these compounds are generally commercially available or can be produced by known methods or equivalent methods thereto.

The peptide derivative (I) as well as the intermediates and starting materials for use in the production of the derivative can be isolated and purified by known procedures. Examples of the known procedures for isolation and purification include solvent extraction, recrystallization, or chromatography.

If the peptide derivative (I) includes optical isomers or stereoisomers, each isomer can be obtained as a single compound by known methods. Examples of the known methods include crystallization, enzymatic resolution, or chiral chromatography.

In each reaction of the production method as described below, if any raw material compound has hydroxy group, amino group, sulfhydryl group, or carboxyl group, a protective group may be introduced to each of these groups and a compound of interest can be obtained by removing the protective group as necessary subsequent to the reaction.

Examples of the protective group for the hydroxy group include trityl group, tetrahydropyranyl group, $C_7$-$C_{10}$ aralkyl group (for example, benzyl group), or substituted silyl group (for example, trimethylsilyl group, triethylsilyl group, or tert-butyldimethylsilyl group).

Examples of the protective group for the amino group include $C_2$-$C_6$ alkylcarbonyl group (for example, acetyl group), benzoyl group, $C_2$-$C_8$ alkyloxycarbonyl group (for example, tert-butoxycarbonyl group or benzyloxycarbonyl group), $C_7$-$C_{10}$ aralkyl group (for example, benzyl group), or phthaloyl group.

Examples of the protective group for the sulfhydryl group include trityl group, 2-mercaptopyridyl group, or 2-mercapto-5-nitropyridyl group.

Examples of the protective group for the carboxyl group include $C_1$-$C_6$ alkyl group (for example, methyl group, ethyl group, or tert-butyl group), or $C_7$-$C_{10}$ aralkyl group (for example, benzyl group).

Protective groups are removed in different ways depending on the type of the protective groups, but the deprotection may be performed according to known methods (for example, Greene, T. W., "Greene's Protective Groups in Organic Synthesis," Wiley-Interscience) or equivalent methods thereto.

The peptide derivative (I) can be obtained, for example, by deprotection reaction of a protected peptide derivative (III), as shown in Scheme 1:

Scheme 1

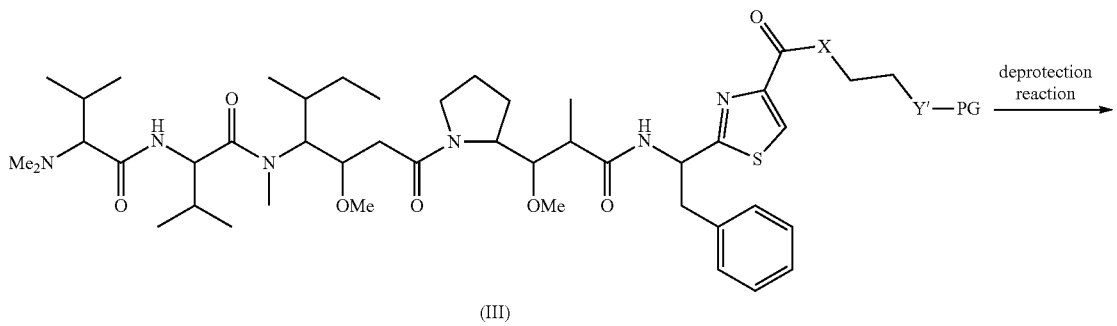

(III)

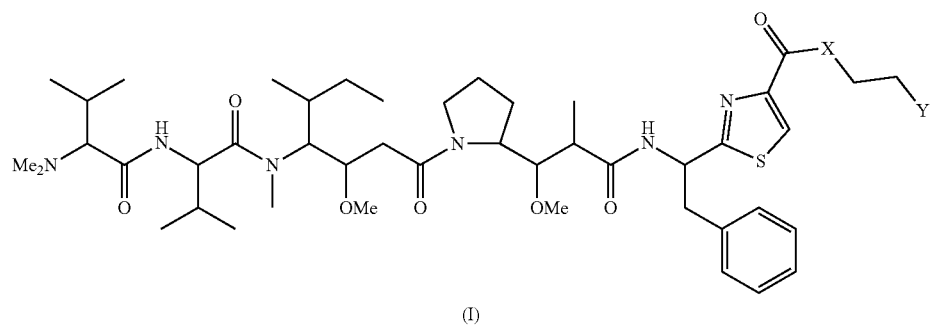

(I)

wherein PG represents the protective group, and when X is NR, Y represents NH$_2$ or SH, and Y' represents NH or S. When X is an oxygen atom, Y represents NH$_2$, SH, OH, or phenyl in which any one of hydrogen atoms is replaced by NH$_2$ or OH, and Y' represents NH, S, O, or phenyl in which any one of hydrogen atoms is replaced by NH or O.

Protective groups are removed in different ways depending on the type of the protective groups, but the deprotection may be performed according to known methods (for example, Greene, T. W., "Greene's Protective Groups in Organic Synthesis," Wiley-Interscience) or equivalent methods thereto.

The protected peptide derivative (III) can be obtained, for example, by the condensation reaction of a carboxylic acid derivative (IV) and a nucleophile (V), as shown in Scheme 2:

A reaction solvent for use in the condensation reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include chlorine-based solvents such as dichloromethane, chloroform, or 1,2-dichloroethane; or aprotic polar solvents such as N,N-dimethylformamide, N,N-dimethylacetamide, N-methyl-2-pyrrolidone, or dimethyl sulfoxide.

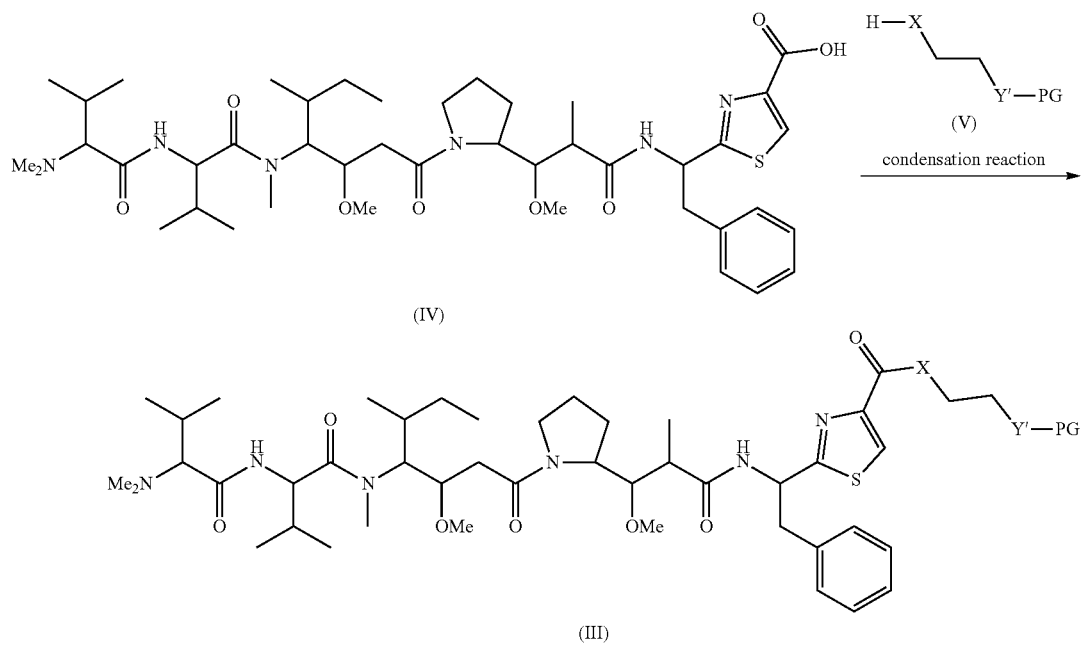

Scheme 2 wherein each symbol is the same as the definition above.

The amount of the nucleophile (V) for use in the condensation reaction is preferably 0.5 to 10 equivalents, more preferably 1 to 3 equivalents, to the carboxylic acid derivative (IV).

Examples of a condensation reagent for use in the condensation reaction include ethyl chloroformate, oxalyl chloride, 1-ethyl-3-(3-dimethylaminopropyl)carbodiimide hydrochloride, 2-(7-aza-1H-benzotriazol-1-yl)-1,1,3,3-tetramethyluronium hexafluorophosphate, O-(benzotriazol-1-yl)-N,N,N',N'-tetramethyluronium hexafluorophosphate, 1H-benzotriazol-1-yloxytripyrrolidinophosphonium hexafluorophosphate, or 2-methyl-6-nitrobenzoic acid anhydride, and preferably include ethyl chloroformate, 2-(7-aza-1H-benzotriazol-1-yl)-1,1,3,3-tetramethyluronium hexafluorophosphate, or 2-methyl-6-nitrobenzoic acid anhydride.

The amount of the condensation reagent for use in the condensation reaction is preferably 0.1 to 100 equivalents, more preferably 0.3 to 30 equivalents, to the carboxylic acid derivative (IV).

The condensation reaction may optionally be performed with a base. Examples of the base to be used include inorganic bases such as sodium hydride, sodium hydrogen carbonate, or potassium carbonate; organic bases such as triethylamine, diisopropylethylamine, 4-dimethylaminopyridine, or pyridine; or mixtures thereof, and preferably include organic bases such as triethylamine, diisopropylethylamine, 4-dimethylaminopyridine, or pyridine; or mixtures thereof.

The amount of the base for use in the condensation reaction is preferably 0.5 to 20 equivalents, more preferably 1 to 5 equivalents, to the carboxylic acid derivative (IV).

The reaction temperature of the condensation reaction is preferably −40° C. to 200° C., more preferably −20° C. to 150° C.

The reaction time of the condensation reaction is appropriately selected depending on the conditions such as reaction temperature, and is preferably 30 minutes to 30 hours.

The concentration of the carboxylic acid derivative (IV) for use in the condensation reaction is preferably 1 mmol/L to 1 mol/L at the start of the reaction.

The nucleophile (V) is commercially available or can be synthesized by known methods or equivalent methods thereto.

Furthermore, the peptide derivative (I) can be obtained, for example, by the condensation reaction of the carboxylic acid derivative (IV) and a nucleophile (VI), as shown in Scheme 3:

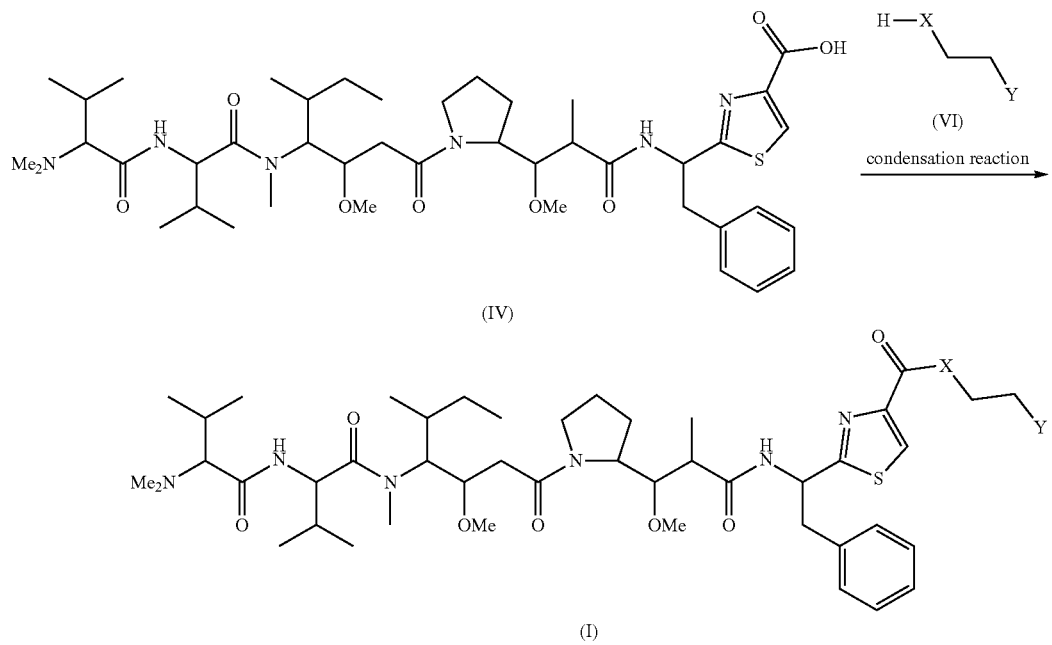

Scheme 3 wherein X represents NR, Y represents OH or phenyl in which any one of hydrogen atoms is replaced by $NH_2$ or OH, and other symbols are the same as the definition above.

The amount of the nucleophile (VI) for use in the condensation reaction is preferably 0.5 to 10 equivalents, more preferably 1 to 3 equivalents, to the carboxylic acid derivative (IV).

Examples of a condensation reagent for use in the condensation reaction include ethyl chloroformate, oxalyl chloride, 1-ethyl-3-(3-dimethylaminopropyl)carbodiimide hydrochloride, 2-(7-aza-1H-benzotriazol-1-yl)-1,1,3,3-tetramethyluronium hexafluorophosphate, 0-(benzotriazol-1-yl)-N,N,N',N'-tetramethyluronium hexafluorophosphate, or 1H-benzotriazol-1-yloxytripyrrolidinophosphonium hexafluorophosphate, and preferably include ethyl chloroformate or 2-(7-aza-1H-benzotriazol-1-yl)-1,1,3,3-tetramethyluronium hexafluorophosphate.

The amount of the condensation reagent for use in the condensation reaction is preferably 0.1 to 100 equivalents, more preferably 0.3 to 30 equivalents, to the carboxylic acid derivative (IV).

A reaction solvent for use in the condensation reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include chlorine-based solvents such as dichloromethane, chloroform, or 1,2-dichloroethane, or aprotic polar solvents such as N,N-dimethylformamide, N,N-dimethylacetamide, N-methyl-2-pyrrolidone, or dimethyl sulfoxide.

The condensation reaction may optionally be performed with a base. Examples of the base to be used include inorganic bases such as sodium hydride, sodium hydrogen carbonate, or potassium carbonate; organic bases such as triethylamine, diisopropylethylamine, 4-dimethylaminopyridine, or pyridine; or mixtures thereof, and preferably include organic bases such as triethylamine, diisopropylethylamine, 4-dimethylaminopyridine, or pyridine; or mixtures thereof.

The amount of the base for use in the condensation reaction is preferably 0.5 to 20 equivalents, more preferably 1 to 5 equivalents, to the carboxylic acid derivative (IV).

The reaction temperature of the condensation reaction is preferably −40° C. to 200° C., more preferably −20° C. to 150° C.

The reaction time of the condensation reaction is appropriately selected depending on the conditions such as reaction temperature, and is preferably 30 minutes to 30 hours.

The concentration of the carboxylic acid derivative (IV) for use in the condensation reaction is preferably 1 mmol/L to 1 mol/L at the start of the reaction.

The nucleophile (VI) is commercially available or can be synthesized by known methods or equivalent methods.

The carboxylic acid derivative (IV) can be obtained, for example, by deprotection of an ester derivative (VII), as shown in Scheme 4:

Scheme 4

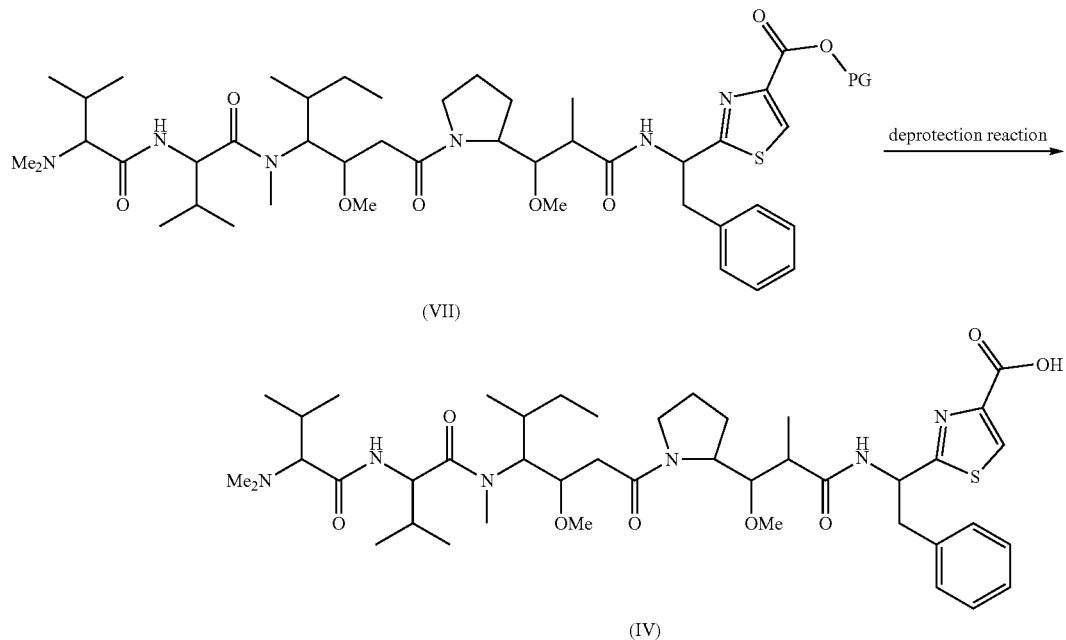

wherein each symbol is the same as the definition above.

Protective groups are removed in different ways depending on the type of the protective groups, but the deprotection may be performed according to known methods (for example, Greene, T. W., "Greene's Protective Groups in Organic Synthesis," Wiley-Interscience) or equivalent methods thereto.

The ester derivative (VII) can also be synthesized by known methods or equivalent methods thereto.

A protected phenoxycarbamate derivative (IX) can be obtained, for example, by condensation reaction of a phenol derivative (I-a) and an electrophile (VIII-a) or (VIII-b), as shown in Scheme 5:

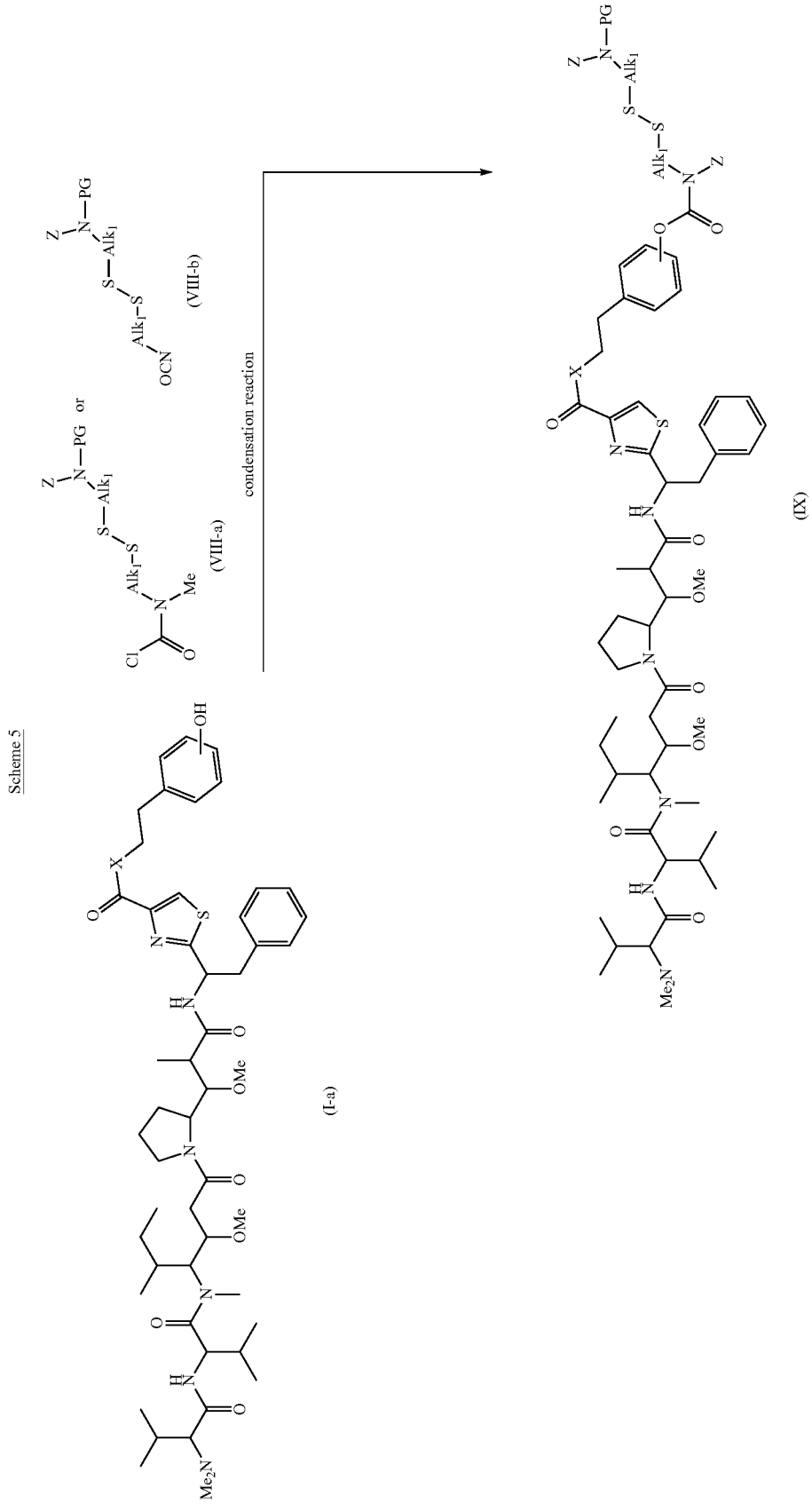
Scheme 5 wherein each symbol is the same as the definition above.

The amount of the electrophile (VIII-a) or (VIII-b) for use in the condensation reaction is preferably 0.5 to 10 equivalents, more preferably 1 to 3 equivalents, to the phenol derivative (I-a).

A reaction solvent for use in the condensation reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, pyridine, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include chlorine-based solvents such as dichloromethane, chloroform, or 1,2-dichloroethane, aprotic polar solvents such as N,N-dimethylformamide, N,N-dimethylacetamide, N-methyl-2-pyrrolidone, pyridine, or dimethyl sulfoxide.

The condensation reaction may optionally be performed with a base. Examples of the base to be used include inorganic bases such as sodium hydride, sodium hydrogen carbonate, or potassium carbonate; organic bases such as triethylamine, diisopropylethylamine, or pyridine; or mixtures thereof, and preferably include organic bases such as triethylamine, diisopropylethylamine, or pyridine.

The amount of the base for use in the condensation reaction is preferably 0.5 to 20 equivalents, more preferably 1 to 5 equivalents, to the phenol derivative (I-a).

The reaction temperature of the condensation reaction is preferably −40° C. to 200° C., more preferably −20° C. to 150° C.

The reaction time of the condensation reaction is appropriately selected depending on the conditions such as reaction temperature, and is preferably 30 minutes to 30 hours.

The concentration of the phenol derivative (I-a) for use in the condensation reaction is preferably 1 mmol/L to 1 mol/L at the start of the reaction.

The electrophile (VIII-a) or (VIII-b) can be synthesized or generated in reaction system from known amine derivatives or carboxylic acid derivatives by known methods or equivalent methods thereto.

A protected polyethylene glycol derivative (XI) can be obtained, for example, by deprotection of the protected phenoxycarbamate derivative (IX) followed by coupling reaction under basic to neutral conditions with a carboxylic acid derivative (X) (when G is succinimidyl or p-nitrophenyl) or by condensation reaction with a carboxylic acid derivative (X) (when G is a hydrogen atom), as shown in Scheme 6:

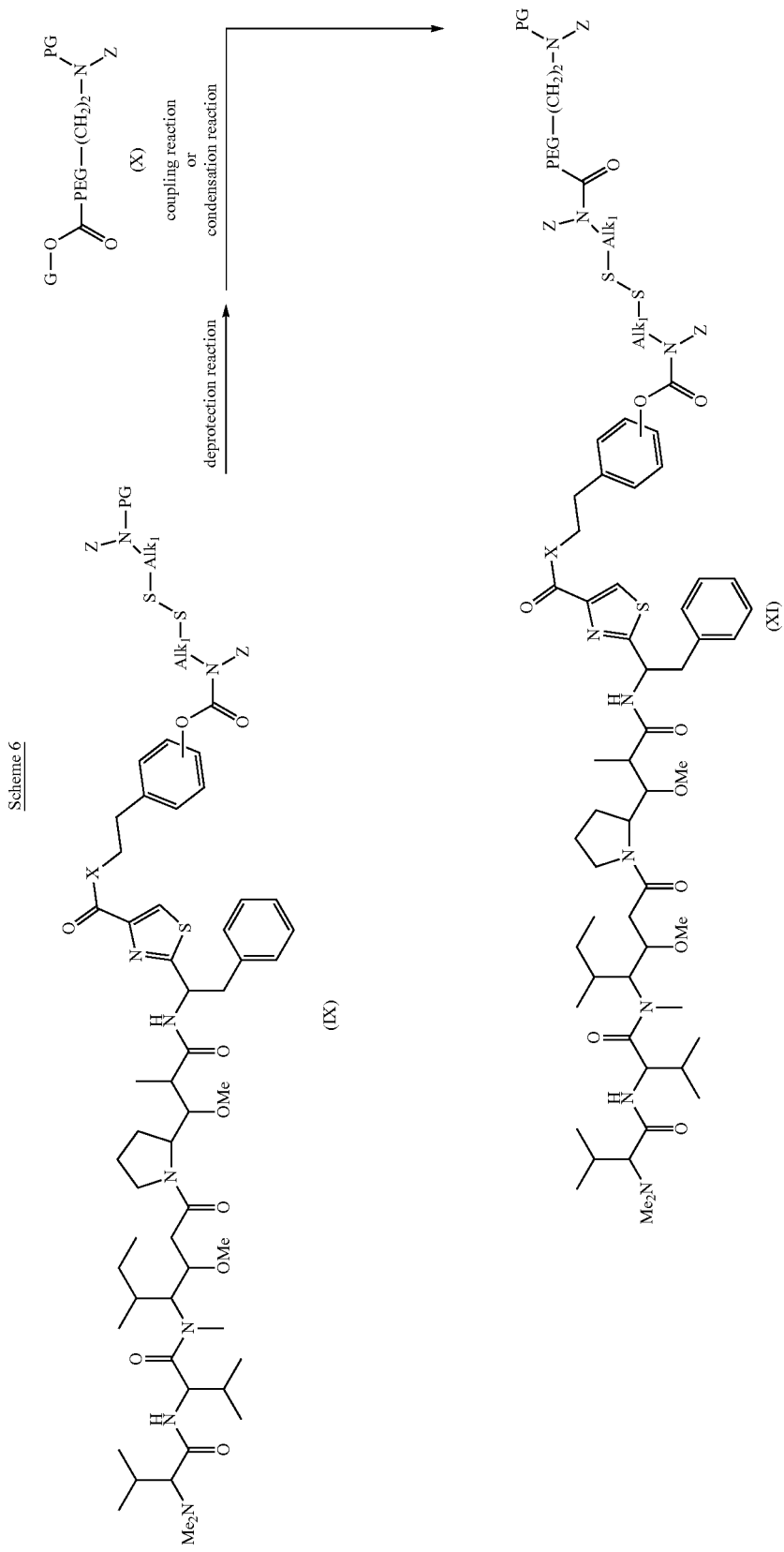

wherein G represents a hydrogen atom, succinimidyl, or p-nitrophenyl, and each of other symbols is the same as the definition above.

Protective groups are removed in different ways depending on the type of the protective groups, but the deprotection may be performed according to known methods (for example, Greene, T. W., "Greene's Protective Groups in Organic Synthesis," Wiley-Interscience) or equivalent methods thereto.

The amount of the carboxylic acid derivative (X) for use in the coupling reaction or condensation reaction is preferably 0.5 to 10 equivalents, more preferably 0.5 to 4 equivalents, to the protected phenoxycarbamate derivative (IX).

Adjustment for pH of the coupling reaction can be made by a base. Examples of the base for use include organic bases such as triethylamine or diisopropylethylamine; inorganic bases such as sodium hydrogen carbonate or potassium carbonate; metal hydride compounds such as sodium hydride, potassium hydride, or calcium hydride; alkyl lithium such as methyl lithium or butyl lithium; lithium amide such as lithium hexamethyldisilazide or lithium diisopropylamide; or mixtures thereof, and preferably include inorganic bases such as sodium hydrogen carbonate or potassium carbonate; or organic bases such as triethylamine or diisopropylethylamine.

The amount of the base for use in the coupling reaction is preferably 0.001 to 10 equivalents, more preferably 0.001 to 4 equivalents, to the protected phenoxycarbamate derivative (IX).

Adjustment for pH of the coupling reaction can also be made by a buffer. Examples of the buffer for use include phosphate buffers, citrate buffers, citric acid-phosphate buffers, boric acid buffers, tartrate buffers, or Tris buffers, and preferably include buffers of pH 7.0 to 8.0.

The concentration of the buffer for use in the coupling reaction is preferably of 10 mmol/L to 1 mol/L.

A reaction solvent for use in the coupling reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; water; or mixed solvents thereof, and preferably include chlorine-based solvents such as dichloromethane, chloroform, or 1,2-dichloroethane; nitrile-based solvents such as acetonitrile or propionitrile; water; or mixed solvents thereof.

The reaction temperature of the coupling reaction is preferably −40° C. to 200° C., more preferably −20° C. to 150° C.

The reaction time of the coupling reaction is appropriately selected depending on the conditions such as reaction temperature, and is preferably 30 minutes to 30 hours.

The concentration of the carboxylic acid derivative (X) for use in the coupling reaction is preferably 1 mmol/L to 1 mol/L at the start of the reaction.

Examples of a condensation reagent for use in the condensation reaction include carbodiimides such as dicyclohexylcarbodiimide, diisopropylcarbodiimide, or 1-ethyl-3-(3-dimethylaminopropyl)carbodiimide hydrochloride; ethyl chloroformate, oxalyl chloride, 2-(7-aza-1H-benzotriazol-1-yl)-1,1,3,3-tetramethyluronium hexafluorophosphate, O-(benzotriazol-1-yl)-N,N,N',N'-tetramethyluronium hexafluorophosphate, 1H-benzotriazol-1-yloxytripyrrolidinophosphonium hexafluorophosphate, or 2-methyl-6-nitrobenzoic acid anhydride, and preferably include carbodiimides such as dicyclohexylcarbodiimide, diisopropylcarbodiimide, or 1-ethyl-3-(3-dimethylaminopropyl)carbodiimide hydrochloride, or 2-(7-aza-1H-benzotriazol-1-yl)-1,1,3,3-tetramethyluronium hexafluorophosphate.

The amount of the condensation reagent for use in the condensation reaction is preferably 0.1 to 100 equivalents, more preferably 0.3 to 30 equivalents, to the carboxylic acid derivative (X).

A reaction solvent for use in the condensation reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include chlorine-based solvents such as dichloromethane, chloroform, or 1,2-dichloroethane, or aprotic polar solvents such as N,N-dimethylformamide, N,N-dimethylacetamide, N-methyl-2-pyrrolidone, or dimethyl sulfoxide.

The condensation reaction may optionally be performed with a base. Examples of the base to be used include inorganic bases such as sodium hydride, sodium hydrogen carbonate, or potassium carbonate; organic bases such as triethylamine, diisopropylethylamine, 4-dimethylaminopyridine, or pyridine; or mixtures thereof, and preferably include organic bases such as triethylamine, diisopropylethylamine, 4-dimethylaminopyridine, or pyridine; or mixtures thereof.

The amount of the base for use in the condensation reaction is preferably 0.5 to 20 equivalents, more preferably 1 to 5 equivalents, to the carboxylic acid derivative (X).

The reaction temperature of the condensation reaction is preferably −40° C. to 200° C., more preferably −20° C. to 150° C.

The reaction time of the condensation reaction is appropriately selected depending on the conditions such as reaction temperature, and is preferably 30 minutes to 30 hours.

The concentration of the carboxylic acid derivative (X) for use in the condensation reaction is preferably 1 mmol/L to 1 mol/L at the start of the reaction.

The carboxylic acid derivative (X) is commercially available or can be synthesized by known methods or equivalent methods.

The prodrug (XIII) of the peptide derivative (I) can be obtained, for example, by deprotection of the protected phenoxycarbamate derivative (IX) followed by coupling reaction under basic to neutral conditions with a carboxylic acid derivative (XII) (when G is succinimidyl or p-nitrophenyl) or by condensation reaction with a carboxylic acid derivative (XII) (when G is a hydrogen atom), as shown in Scheme 7:

Scheme 7
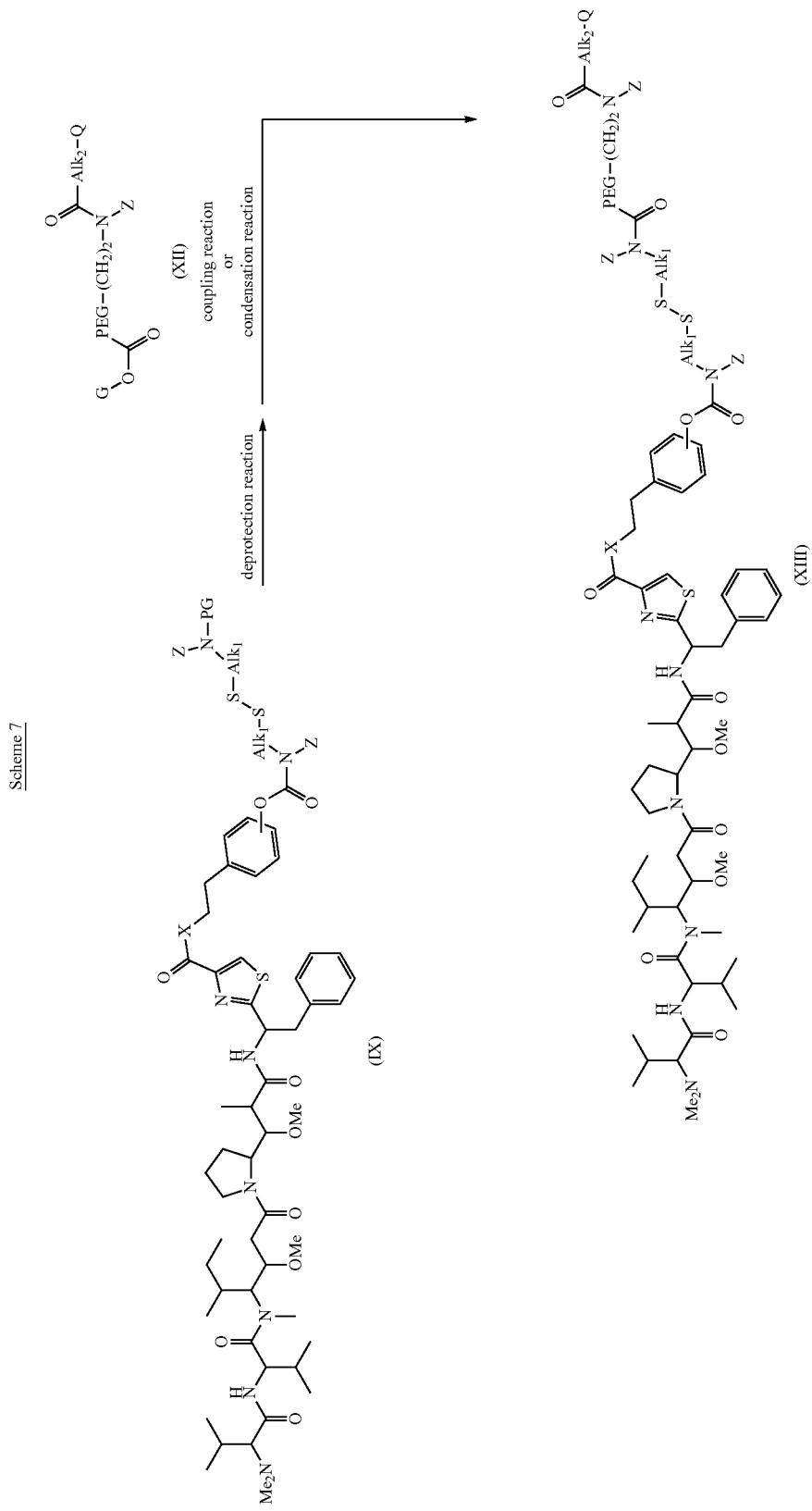

wherein each symbol is the same as the definition above.

Protective groups are removed in different ways depending on the type of the protective groups, but the deprotection may be performed according to known methods (for example, Greene, T. W., "Greene's Protective Groups in Organic Synthesis," Wiley-Interscience) or equivalent methods thereto.

The amount of the carboxylic acid derivative (XII) for use in the coupling reaction or condensation reaction is preferably 0.5 to 10 equivalents, more preferably 0.5 to 4 equivalents, to the protected phenoxycarbamate derivative (IX).

Adjustment for pH of the coupling reaction can be made by a base. Examples of the base for use include organic bases such as triethylamine or diisopropylethylamine; inorganic bases such as sodium hydrogen carbonate or potassium carbonate; metal hydride compounds such as sodium hydride, potassium hydride, or calcium hydride; alkyl lithium such as methyl lithium or butyl lithium; lithium amide such as lithium hexamethyldisilazide or lithium diisopropylamide; or mixtures thereof, and preferably include inorganic bases such as sodium hydrogen carbonate or potassium carbonate; or organic bases such as triethylamine or diisopropylethylamine.

The amount of the base for use in the coupling reaction is preferably 0.001 to 10 equivalents, more preferably 0.001 to 4 equivalents, to the protected phenoxycarbamate derivative (IX).

Adjustment for pH of the coupling reaction can also be made by a buffer. Examples of the buffer for use include phosphate buffers, citrate buffers, citric acid-phosphate buffers, boric acid buffers, tartrate buffers, or Tris buffers, and preferably include buffers of pH 7.0 to 8.0.

The concentration of the buffer for use in the coupling reaction is preferably 10 mmol/L to 1 mol/L.

A reaction solvent for use in the coupling reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; water; or mixed solvents thereof, and preferably include chlorine-based solvents such as dichloromethane, chloroform, or 1,2-dichloroethane; nitrile-based solvents such as acetonitrile or propionitrile; water; or mixed solvents thereof.

The reaction temperature of the coupling reaction is preferably −40° C. to 200° C., more preferably −20° C. to 150° C.

The reaction time of the coupling reaction is appropriately selected depending on the conditions such as reaction temperature, and is preferably 30 minutes to 30 hours.

The concentration of the carboxylic acid derivative (XII) for use in the coupling reaction is preferably 1 mmol/L to 1 mol/L at the start of the reaction.

Examples of a condensation reagent for use in the condensation reaction include carbodiimides such as dicyclohexylcarbodiimide, diisopropylcarbodiimide, or 1-ethyl-3-(3-dimethylaminopropyl)carbodiimide hydrochloride; ethyl chloroformate, oxalyl chloride, 2-(7-aza-1H-benzotriazol-1-yl)-1,1,3,3-tetramethyluronium hexafluorophosphate, O-(benzotriazol-1-yl)-N,N,N',N'-tetramethyluronium hexafluorophosphate, 1H-benzotriazol-1-yloxytripyrrolidinophosphonium hexafluorophosphate, or 2-methyl-6-nitrobenzoic acid anhydride, and preferably include carbodiimides such as dicyclohexylcarbodiimide, diisopropylcarbodiimide, or 1-ethyl-3-(3-dimethylaminopropyl)carbodiimide hydrochloride, or 2-(7-aza-1H-benzotriazol-1-yl)-1,1,3,3-tetramethyluronium hexafluorophosphate.

The amount of the condensation reagent for use in the condensation reaction is preferably 0.1 to 100 equivalents, more preferably 0.3 to 30 equivalents, to the carboxylic acid derivative (XII).

A reaction solvent for use in the condensation reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include chlorine-based solvents such as dichloromethane, chloroform, or 1,2-dichloroethane; or aprotic polar solvents such as N,N-dimethylformamide, N,N-dimethylacetamide, N-methyl-2-pyrrolidone, or dimethyl sulfoxide.

The condensation reaction may optionally be performed with a base. Examples of the base to be used include inorganic bases such as sodium hydride, sodium hydrogen carbonate, or potassium carbonate; organic bases such as triethylamine, diisopropylethylamine, 4-dimethylaminopyridine, or pyridine; or mixtures thereof, and preferably include organic bases such as triethylamine, diisopropylethylamine, 4-dimethylaminopyridine, or pyridine; or mixtures thereof.

The amount of the base for use in the condensation reaction is preferably 0.5 to 20 equivalents, more preferably 1 to 5 equivalents, to the carboxylic acid derivative (XII).

The reaction temperature of the condensation reaction is preferably −40° C. to 200° C., more preferably −20° C. to 150° C.

The reaction time of the condensation reaction is appropriately selected depending on the conditions such as reaction temperature, and is preferably 30 minutes to 30 hours.

The concentration of the carboxylic acid derivative (XII) for use in the condensation reaction is preferably 1 mmol/L to 1 mol/L at the start of the reaction.

The carboxylic acid derivative (XII) is commercially available or can be synthesized by known methods or equivalent methods.

The prodrug (XIII) of the peptide derivative (I) can be obtained, for example, by deprotection of the protected polyethylene glycol derivative (XI) followed by coupling reaction under basic to neutral conditions with the carboxylic acid derivative (XIV) (when G is succinimidyl or p-nitrophenyl) or by condensation reaction with the carboxylic acid derivative (XIV) (when G is a hydrogen atom), as shown in Scheme 8:

Scheme 8
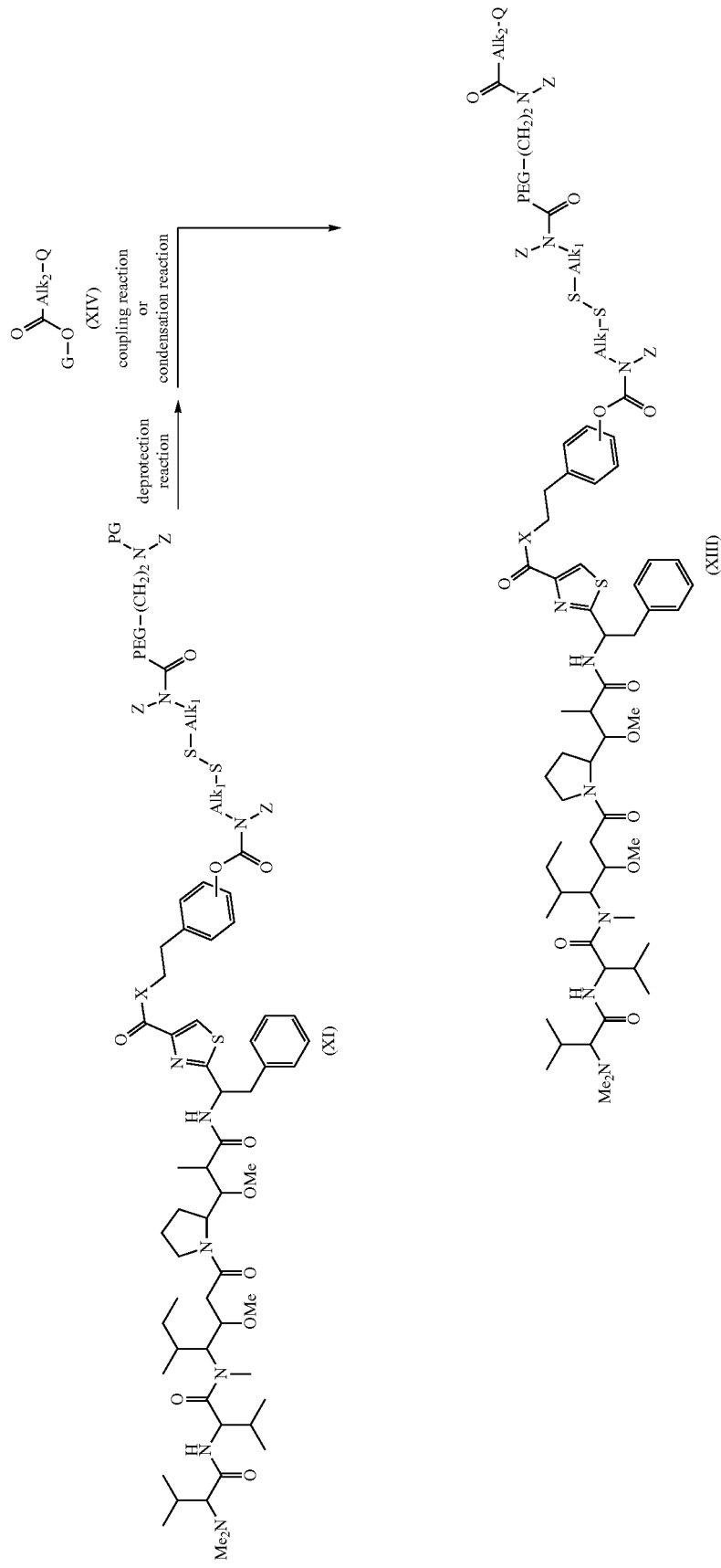

wherein each symbol is the same as the definition above.

Protective groups are removed in different ways depending on the type of the protective groups, but the deprotection may be performed according to known methods (for example, Greene, T. W., "Greene's Protective Groups in Organic Synthesis," Wiley-Interscience) or equivalent methods thereto.

The amount of the carboxylic acid derivative (XIV) for use in the coupling reaction or condensation reaction is preferably 0.5 to 10 equivalents, more preferably 0.5 to 4 equivalents, to the protected polyethylene glycol derivative (XI).

Adjustment for pH of the coupling reaction can be made by a base. Examples of the base for use include organic bases such as triethylamine or diisopropylethylamine; inorganic bases such as sodium hydrogen carbonate or potassium carbonate; metal hydride compounds such as sodium hydride, potassium hydride, or calcium hydride; alkyl lithium such as methyl lithium or butyl lithium; lithium amide such as lithium hexamethyldisilazide or lithium diisopropylamide; or mixtures thereof, and preferably include inorganic bases such as sodium hydrogen carbonate or potassium carbonate; or organic bases such as triethylamine or diisopropylethylamine.

The amount of the base for use in the coupling reaction is preferably 0.001 to 10 equivalents, more preferably 0.001 to 4 equivalents, to the protected polyethylene glycol derivative (XI).

Adjustment for pH of the coupling reaction can also be made by a buffer. Examples of the buffer for use include phosphate buffers, citrate buffers, citric acid-phosphate buffers, boric acid buffers, tartrate buffers, or Tris buffers, and preferably include buffers of pH 7.0 to 8.0.

The concentration of the buffer for use in the coupling reaction is preferably 10 mmol/L to 1 mol/L.

A reaction solvent for use in the coupling reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; water; or mixed solvents thereof, and preferably include chlorine-based solvents such as dichloromethane, chloroform, or 1,2-dichloroethane; nitrile-based solvents such as acetonitrile or propionitrile; water; or mixed solvents thereof.

The reaction temperature of the coupling reaction is preferably −40° C. to 200° C., more preferably −20° C. to 150° C.

The reaction time of the coupling reaction is appropriately selected depending on the conditions such as reaction temperature, and is preferably 30 minutes to 30 hours.

The concentration of the carboxylic acid derivative (XIV) for use in the coupling reaction is preferably 1 mmol/L to 1 mol/L at the start of the reaction.

Examples of a condensation reagent for use in the condensation reaction include carbodiimides such as dicyclohexylcarbodiimide, diisopropylcarbodiimide, or 1-ethyl-3-(3-dimethylaminopropyl)carbodiimide hydrochloride; ethyl chloroformate, oxalyl chloride, 2-(7-aza-1H-benzotriazol-1-yl)-1,1,3,3-tetramethyluronium hexafluorophosphate, O-(benzotriazol-1-yl)-N,N,N',N'-tetramethyluronium hexafluorophosphate, 1H-benzotriazol-1-yloxytripyrrolidinophosphonium hexafluorophosphate, or 2-methyl-6-nitrobenzoic acid anhydride, and preferably include carbodiimides such as dicyclohexylcarbodiimide, diisopropylcarbodiimide, or 1-ethyl-3-(3-dimethylaminopropyl)carbodiimide hydrochloride; or 2-(7-aza-1H-benzotriazol-1-yl)-1,1,3,3-tetramethyluronium hexafluorophosphate.

The amount of the condensation reagent for use in the condensation reaction is preferably 0.1 to 100 equivalents, more preferably 0.3 to 30 equivalents, to the carboxylic acid derivative (XIV).

A reaction solvent for use in the condensation reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include chlorine-based solvents such as dichloromethane, chloroform, or 1,2-dichloroethane; or aprotic polar solvents such as N,N-dimethylformamide, N,N-dimethylacetamide, N-methyl-2-pyrrolidone, or dimethyl sulfoxide.

The condensation reaction may optionally be performed with a base. Examples of the base to be used include inorganic bases such as sodium hydride, sodium hydrogen carbonate, or potassium carbonate; organic bases such as triethylamine, diisopropylethylamine, 4-dimethylaminopyridine, or pyridine; or mixtures thereof, and preferably include organic bases such as triethylamine, diisopropylethylamine, 4-dimethylaminopyridine, or pyridine; or mixtures thereof.

The amount of the base for use in the condensation reaction is preferably 0.5 to 20 equivalents, more preferably 1 to 5 equivalents, to the carboxylic acid derivative (XIV).

The reaction temperature of the condensation reaction is preferably −40° C. to 200° C., more preferably −20° C. to 150° C.

The reaction time of the condensation reaction is appropriately selected depending on the conditions such as reaction temperature, and is preferably 30 minutes to 30 hours.

The concentration of the carboxylic acid derivative (XIV) for use in the condensation reaction is preferably 1 mmol/L to 1 mol/L at the start of the reaction.

The carboxylic acid derivative (XIV) is commercially available or can be synthesized by known methods or equivalent methods.

The prodrug (XV) of the peptide derivative (I) can be obtained, for example, by deprotection of the protected phenoxycarbamate derivative (IX) followed by coupling reaction under basic to neutral conditions with the carboxylic acid derivative (XIV) (when G is succinimidyl or p-nitrophenyl) or by condensation reaction with the carboxylic acid derivative (XIV) (when G is a hydrogen atom), as shown in Scheme 9:

Scheme 9
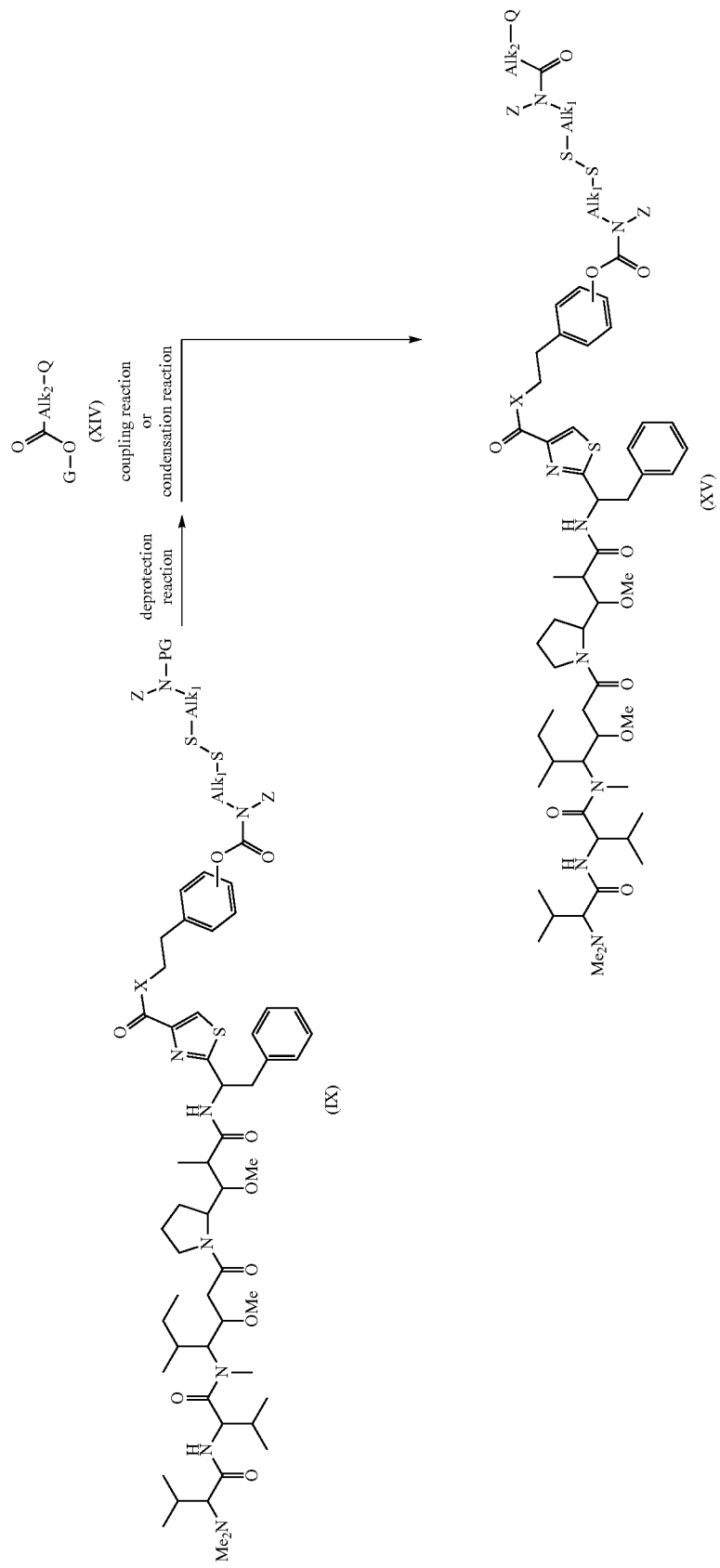

wherein each symbol is the same as the definition above.

Protective groups are removed in different ways depending on the type of the protective groups, but the deprotection may be performed according to known methods (for example, Greene, T. W., "Greene's Protective Groups in Organic Synthesis," Wiley-Interscience) or equivalent methods.

The amount of the carboxylic acid derivative (XIV) for use in the coupling reaction or condensation reaction is preferably 0.5 to 10 equivalents, more preferably 0.5 to 4 equivalents, to the protected phenoxycarbamate derivative (IX).

Adjustment for pH of the coupling reaction can be made by a base. Examples of the base for use include organic bases such as triethylamine or diisopropylethylamine; inorganic bases such as sodium hydrogen carbonate or potassium carbonate; metal hydride compounds such as sodium hydride, potassium hydride, or calcium hydride; alkyl lithium such as methyl lithium or butyl lithium; lithium amide such as lithium hexamethyldisilazide or lithium diisopropylamide; or mixtures thereof, and preferably include inorganic bases such as sodium hydrogen carbonate or potassium carbonate; or organic bases such as triethylamine or diisopropylethylamine.

The amount of the base for use in the coupling reaction is preferably 0.001 to 10 equivalents, more preferably 0.001 to 4 equivalents, to the protected phenoxycarbamate derivative (IX).

Adjustment for pH of the coupling reaction can also be made by a buffer. Examples of the buffer for use include phosphate buffers, citrate buffers, citric acid-phosphate buffers, boric acid buffers, tartrate buffers, or Tris buffers, and preferably include buffers of pH 7.0 to 8.0.

The concentration of the buffer for use in the coupling reaction is preferably of 10 mmol/L to 1 mol/L.

A reaction solvent for use in the coupling reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; water; or mixed solvents thereof, and preferably include chlorine-based solvents such as dichloromethane, chloroform, or 1,2-dichloroethane; nitrile-based solvents such as acetonitrile or propionitrile; water; or mixed solvents thereof.

The reaction temperature of the coupling reaction is preferably −40° C. to 200° C., more preferably −20° C. to 150° C.

The reaction time of the coupling reaction is appropriately selected depending on the conditions such as reaction temperature, and is preferably 30 minutes to 30 hours.

The concentration of the carboxylic acid derivative (XIV) for use in the coupling reaction is preferably 1 mmol/L to 1 mol/L at the start of the reaction.

Examples of a condensation reagent for use in the condensation reaction include carbodiimides such as dicyclohexylcarbodiimide, diisopropylcarbodiimide, or 1-ethyl-3-(3-dimethylaminopropyl)carbodiimide hydrochloride; ethyl chloroformate, oxalyl chloride, 2-(7-aza-1H-benzotriazol-1-yl)-1,1,3,3-tetramethyluronium hexafluorophosphate, O-(benzotriazol-1-yl)-N,N,N',N'-tetramethyluronium hexafluorophosphate, 1H-benzotriazol-1-yloxytripyrrolidinophosphonium hexafluorophosphate, or 2-methyl-6-nitrobenzoic acid anhydride, and preferably include carbodiimides such as dicyclohexylcarbodiimide, diisopropylcarbodiimide, or 1-ethyl-3-(3-dimethylaminopropyl)carbodiimide hydrochloride; or 2-(7-aza-1H-benzotriazol-1-yl)-1,1,3,3-tetramethyluronium hexafluorophosphate.

The amount of the condensation reagent for use in the condensation reaction is preferably 0.1 to 100 equivalents, more preferably 0.3 to 30 equivalents, to the carboxylic acid derivative (XIV).

A reaction solvent for use in the condensation reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include chlorine-based solvents such as dichloromethane, chloroform, or 1,2-dichloroethane; or aprotic polar solvents such as N,N-dimethylformamide, N,N-dimethylacetamide, N-methyl-2-pyrrolidone, or dimethyl sulfoxide.

The condensation reaction may optionally be performed with a base. Examples of the base to be used include inorganic bases such as sodium hydride, sodium hydrogen carbonate, or potassium carbonate; organic bases such as triethylamine, diisopropylethylamine, 4-dimethylaminopyridine, or pyridine; or mixtures thereof, and preferably include organic bases such as triethylamine, diisopropylethylamine, 4-dimethylaminopyridine, or pyridine; or mixtures thereof.

The amount of the base for use in the condensation reaction is preferably 0.5 to 20 equivalents, more preferably 1 to 5 equivalents, to the carboxylic acid derivative (XIV).

The reaction temperature of the condensation reaction is preferably −40° C. to 200° C., more preferably −20° C. to 150° C.

The reaction time of the condensation reaction is appropriately selected depending on the conditions such as reaction temperature, and is preferably 30 minutes to 30 hours.

The concentration of the carboxylic acid derivative (XIV) for use in the condensation reaction is preferably 1 mmol/L to 1 mol/L at the start of the reaction.

The disulfide derivative (XVII) can be obtained, for example, by the condensation reaction of a carboxylic acid derivative (IV) and a nucleophile (XVI), as shown in Scheme 10:

Scheme 10

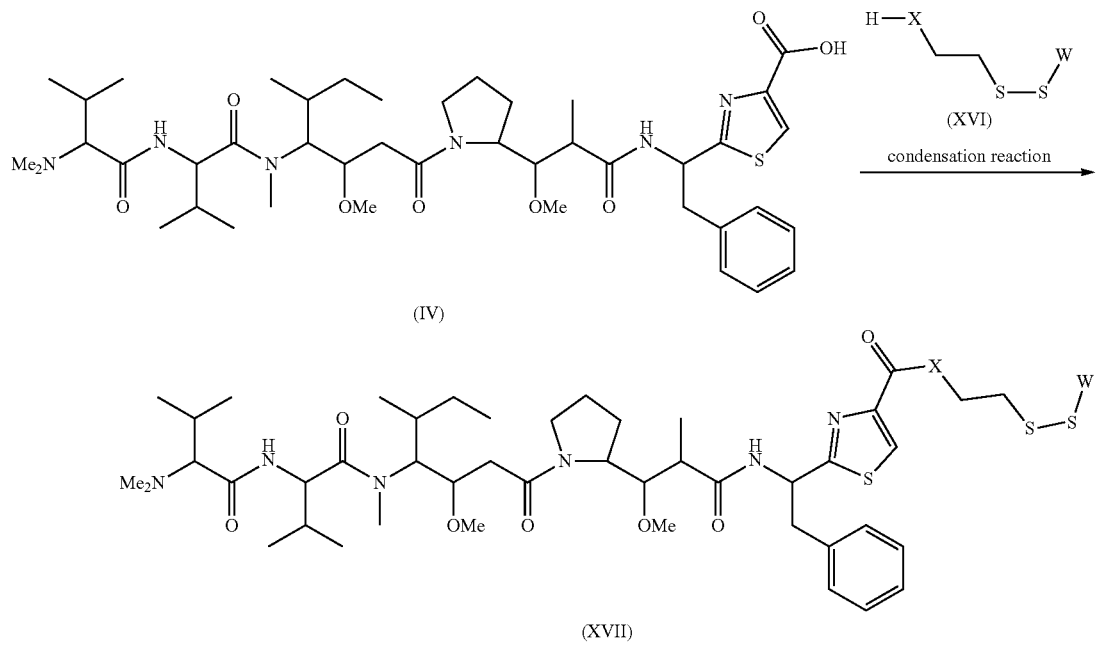

(IV)

(XVII)

wherein W represents 2-mercaptopyridyl, 2-mercapto-5-nitropyridyl, or -Alk$_1$-N(Z) (PG), and the other symbols are the same as the definition above.

The amount of the nucleophile (XVI) for use in the condensation reaction is preferably 0.5 to 10 equivalents, more preferably 1 to 3 equivalents, to the carboxylic acid derivative (IV).

Examples of a condensation reagent for use in the condensation reaction include ethyl chloroformate, oxalyl chloride, 1-ethyl-3-(3-dimethylaminopropyl)carbodiimide hydrochloride, 2-(7-aza-1H-benzotriazol-1-yl)-1,1,3,3-tetramethyluronium hexafluorophosphate, 0-(benzotriazol-1-yl)-N,N,N',N'-tetramethyluronium hexafluorophosphate, 1H-benzotriazol-1-yloxytripyrrolidinophosphonium hexafluorophosphate, or 2-methyl-6-nitrobenzoic acid anhydride, and preferably include ethyl chloroformate or 2-(7-aza-1H-benzotriazol-1-yl)-1,1,3,3-tetramethyluronium hexafluorophosphate, 1H-benzotriazol-1-yloxytripyrrolidinophosphonium hexafluorophosphate, or 2-methyl-6-nitrobenzoic acid anhydride.

The amount of the condensation reagent for use in the condensation reaction is preferably 0.1 to 100 equivalents, more preferably 0.3 to 30 equivalents, to the carboxylic acid derivative (IV).

A reaction solvent for use in the condensation reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include chlorine-based solvents such as dichloromethane, chloroform, or 1,2-dichloroethane; or aprotic polar solvents such as N,N-dimethylformamide, N,N-dimethylacetamide, N-methyl-2-pyrrolidone, or dimethyl sulfoxide.

The condensation reaction may optionally be performed with a base. Examples of the base to be used include inorganic bases such as sodium hydride, sodium hydrogen carbonate, or potassium carbonate; organic bases such as triethylamine, diisopropylethylamine, 4-dimethylaminopyridine, or pyridine; or mixtures thereof, and preferably include organic bases such as triethylamine, diisopropylethylamine, 4-dimethylaminopyridine, or pyridine; or mixtures thereof.

The amount of the base for use in the condensation reaction is preferably 0.5 to 20 equivalents, more preferably 1 to 5 equivalents, to the carboxylic acid derivative (IV).

The reaction temperature of the condensation reaction is preferably −40° C. to 200° C., more preferably −20° C. to 150° C.

The reaction time of the condensation reaction is appropriately selected depending on the conditions such as reaction temperature, and is preferably 30 minutes to 30 hours.

The concentration of the carboxylic acid derivative (IV) for use in the condensation reaction is preferably 1 mmol/L to 1 mol/L at the start of the reaction.

The nucleophile (XVI) is commercially available or can be synthesized by known methods or equivalent methods thereto.

A protected polyethylene glycol derivative (XVIII) can be obtained, for example, by deprotection of the disulfide derivative (XVII-a) followed by coupling reaction under basic to neutral conditions with the carboxylic acid derivative (X) (when G is succinimidyl or p-nitrophenyl) or by condensation reaction with the carboxylic acid derivative (X) (when G is a hydrogen atom), as shown in Scheme 11:

Scheme 11
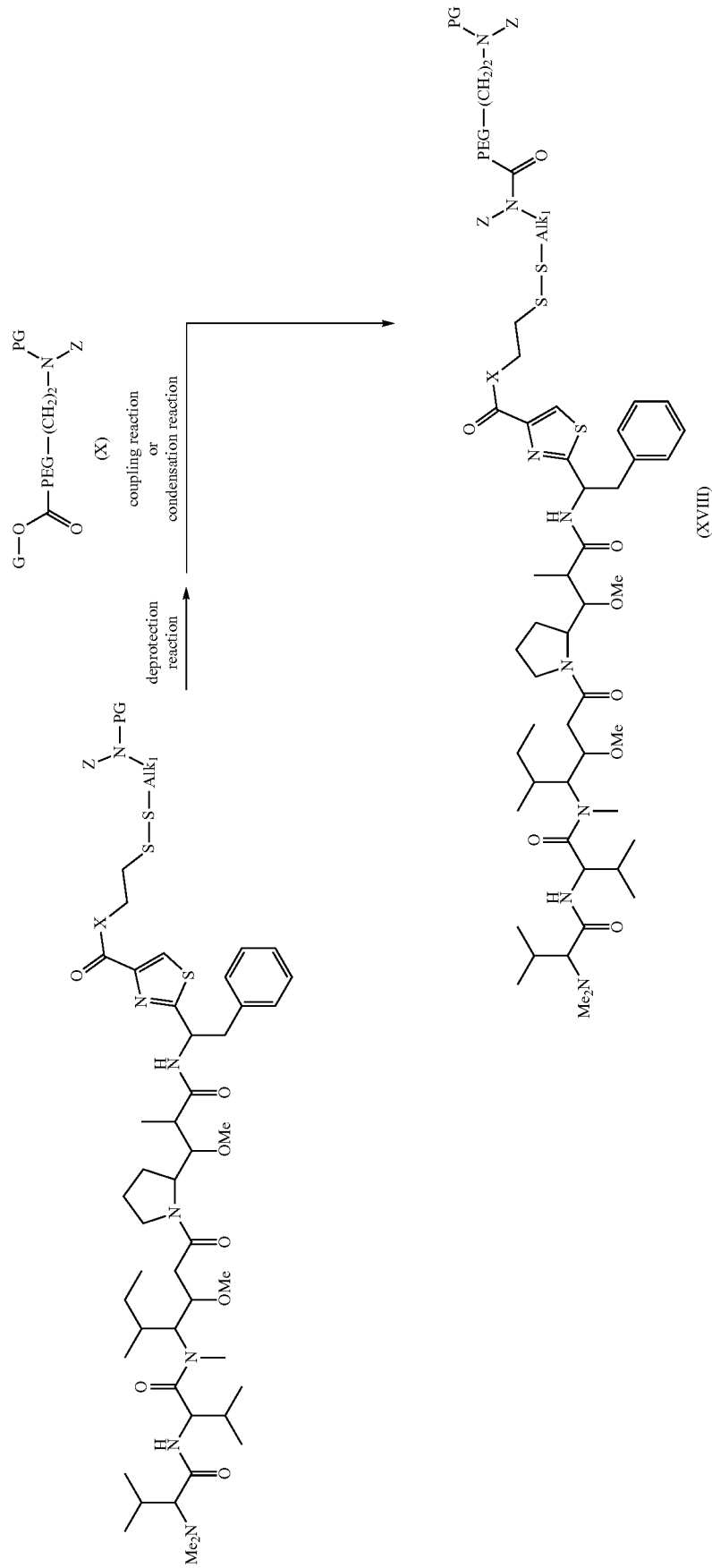

wherein each symbol is the same as the definition above.

Protective groups are removed in different ways depending on the type of the protective groups, but the deprotection may be performed according to known methods (for example, Greene, T. W., "Greene's Protective Groups in Organic Synthesis," Wiley-Interscience) or equivalent methods.

The amount of the carboxylic acid derivative (X) for use in the coupling reaction or condensation reaction is preferably 0.5 to 10 equivalents, more preferably 0.5 to 4 equivalents, to the disulfide derivative (XVII-a).

Adjustment for pH of the coupling reaction can be made by a base. Examples of the base for use include organic bases such as triethylamine or diisopropylethylamine; inorganic bases such as sodium hydrogen carbonate or potassium carbonate; metal hydride compounds such as sodium hydride, potassium hydride, or calcium hydride; alkyl lithium such as methyl lithium or butyl lithium; lithium amide such as lithium hexamethyldisilazide or lithium diisopropylamide; or mixtures thereof, and preferably include inorganic bases such as sodium hydrogen carbonate or potassium carbonate; or organic bases such as triethylamine or diisopropylethylamine.

The amount of the base for use in the coupling reaction is preferably 0.001 to 10 equivalents, more preferably 0.001 to 4 equivalents, to the disulfide derivative (XVII-a).

Adjustment for pH of the coupling reaction can also be made by a buffer. Examples of the buffer for use include phosphate buffers, citrate buffers, citric acid-phosphate buffers, boric acid buffers, tartrate buffers, or Tris buffers, and preferably include buffers of pH 7.0 to 8.0.

The concentration of the buffer for use in the coupling reaction is preferably 10 mmol/L to 1 mol/L.

A reaction solvent for use in the coupling reaction is appropriately selected depending on the type of reagents to be used, but it is not particularly limited as long as the reaction is not inhibited. Examples of the reaction solvent include aprotic polar solvent such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; water; or mixed solvents thereof, and preferably include chlorine-based solvents such as dichloromethane, chloroform, or 1,2-dichloroethane; nitrile-based solvents such as acetonitrile or propionitrile; water; or mixed solvents thereof.

The reaction temperature of the coupling reaction is preferably −40° C. to 200° C., more preferably −20° C. to 150° C.

The reaction time of the coupling reaction is appropriately selected depending on the conditions such as reaction temperature, and is preferably 30 minutes to 30 hours.

The concentration of the carboxylic acid derivative (X) for use in the coupling reaction is preferably 1 mmol/L to 1 mol/L at the start of the reaction.

Examples of a condensation reagent for use in the condensation reaction include carbodiimides such as dicyclohexylcarbodiimide, diisopropylcarbodiimide, or 1-ethyl-3-(3-dimethylaminopropyl)carbodiimide hydrochloride; ethyl chloroformate, oxalyl chloride, 2-(7-aza-1H-benzotriazol-1-yl)-1,1,3,3-tetramethyluronium hexafluorophosphate, O-(benzotriazol-1-yl)-N,N,N',N'-tetramethyluronium hexafluorophosphate, 1H-benzotriazol-1-yloxytripyrrolidinophosphonium hexafluorophosphate, or 2-methyl-6-nitrobenzoic acid anhydride, and preferably include carbodiimides such as dicyclohexylcarbodiimide, diisopropylcarbodiimide, or 1-ethyl-3-(3-dimethylaminopropyl)carbodiimide hydrochloride; or 2-(7-aza-1H-benzotriazol-1-yl)-1,1,3,3-tetramethyluronium hexafluorophosphate.

The amount of the condensation reagent for use in the condensation reaction is preferably 0.1 to 100 equivalents, more preferably 0.3 to 30 equivalents, to the carboxylic acid derivative (X).

A reaction solvent for use in the condensation reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include chlorine-based solvents such as dichloromethane, chloroform, or 1,2-dichloroethane; or aprotic polar solvents such as N,N-dimethylformamide, N,N-dimethylacetamide, N-methyl-2-pyrrolidone, or dimethyl sulfoxide.

The condensation reaction may optionally be performed with a base. Examples of the base to be used include inorganic bases such as sodium hydride, sodium hydrogen carbonate, or potassium carbonate; organic bases such as triethylamine, diisopropylethylamine, 4-dimethylaminopyridine, or pyridine; or mixtures thereof, and preferably include organic bases such as triethylamine, diisopropylethylamine, 4-dimethylaminopyridine, or pyridine; or mixtures thereof.

The amount of the base for use in the condensation reaction is preferably 0.5 to 20 equivalents, more preferably 1 to 5 equivalents, to the carboxylic acid derivative (X).

The reaction temperature of the condensation reaction is preferably −40° C. to 200° C., more preferably −20° C. to 150° C.

The reaction time of the condensation reaction is appropriately selected depending on the conditions such as reaction temperature, and is preferably 30 minutes to 30 hours.

The concentration of the carboxylic acid derivative (X) for use in the condensation reaction is preferably 1 mmol/L to 1 mol/L at the start of the reaction.

The prodrug (XIX) of the peptide derivative (I) can be obtained, for example, by deprotection of the disulfide derivative (XVII-a) followed by coupling reaction under basic to neutral conditions with the carboxylic acid derivative (XII) (when G is succinimidyl or p-nitrophenyl) or by condensation reaction with the carboxylic acid derivative (XII) (when G is a hydrogen atom), as shown in Scheme 12:

Scheme 12
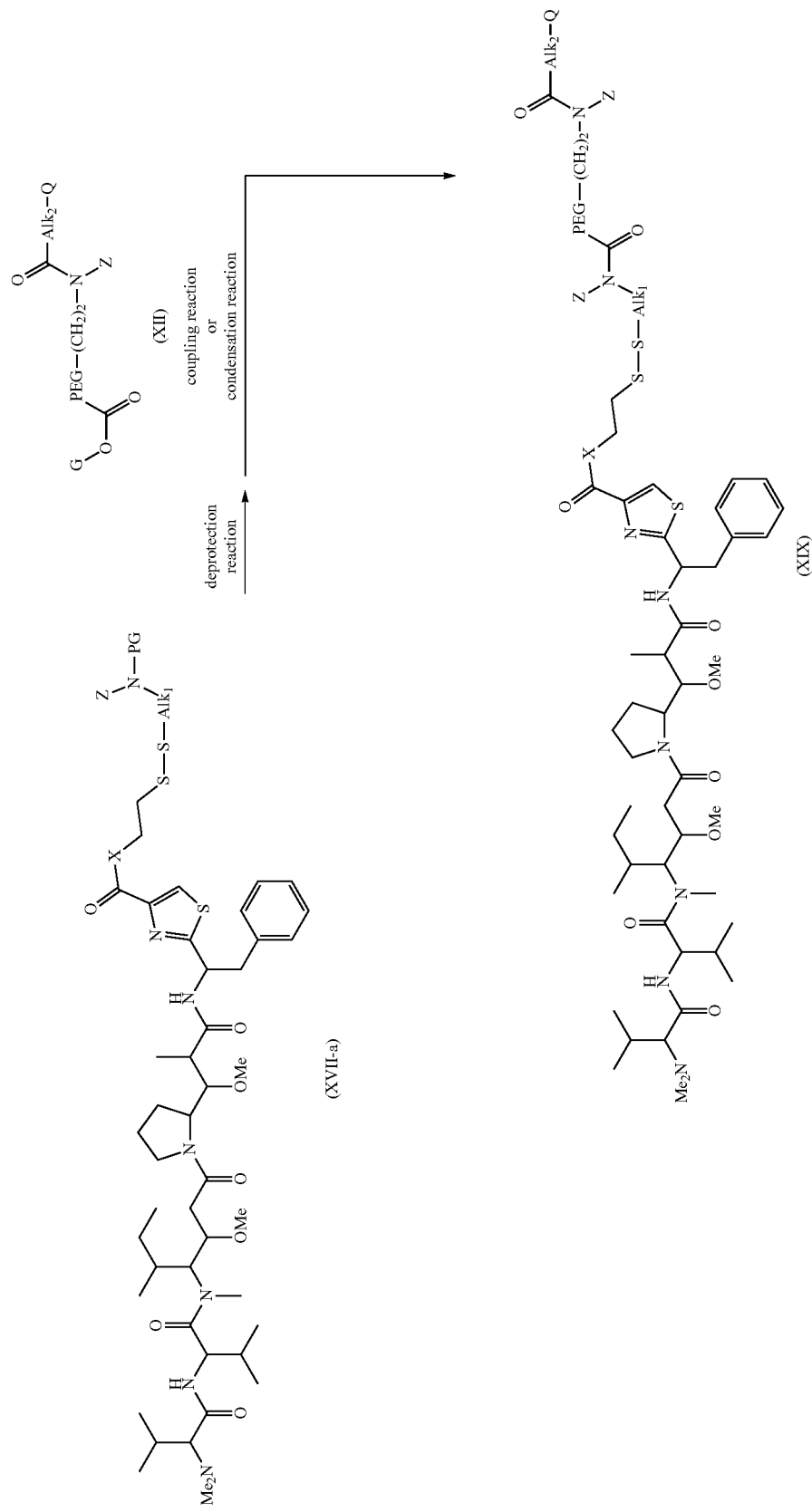

wherein each symbol is the same as the definition above.

Protective groups are removed in different ways depending on the type of the protective groups, but the deprotection may be performed according to known methods (for example, Greene, T. W., "Greene's Protective Groups in Organic Synthesis," Wiley-Interscience) or equivalent methods.

The amount of the carboxylic acid derivative (XII) for use in the coupling reaction or the condensation reaction is preferably 0.5 to 10 equivalents, more preferably 0.5 to 4 equivalents, to the disulfide derivative (XVII-a).

Adjustment for pH of the coupling reaction can be made by a base. Examples of the base for use include organic bases such as triethylamine or diisopropylethylamine; inorganic bases such as sodium hydrogen carbonate or potassium carbonate; metal hydride compounds such as sodium hydride, potassium hydride, or calcium hydride; alkyl lithium such as methyl lithium or butyl lithium; lithium amide such as lithium hexamethyldisilazide or lithium diisopropylamide; or mixtures thereof, and preferably include inorganic bases such as sodium hydrogen carbonate or potassium carbonate, or organic bases such as triethylamine or diisopropylethylamine.

The amount of the base for use in the coupling reaction is preferably 0.001 to 10 equivalents, more preferably 0.001 to 4 equivalents, to the disulfide derivative (XVII-a).

Adjustment for pH of the coupling reaction can also be made by a buffer. Examples of the buffer for use include phosphate buffers, citrate buffers, citric acid-phosphate buffers, boric acid buffers, tartrate buffers, or Tris buffers, and preferably include buffers of pH 7.0 to 8.0.

The concentration of the buffer for use in the coupling reaction is preferably 10 mmol/L to 1 mol/L.

A reaction solvent for use in the coupling reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; water; or mixed solvents thereof, and preferably include chlorine-based solvents such as dichloromethane, chloroform, or 1,2-dichloroethane; nitrile-based solvents such as acetonitrile or propionitrile; water; or mixed solvents thereof.

The reaction temperature of the coupling reaction is preferably −40° C. to 200° C., more preferably −20° C. to 150° C.

The reaction time of the coupling reaction is appropriately selected depending on the conditions such as reaction temperature, and is preferably 30 minutes to 30 hours.

The concentration of the carboxylic acid derivative (XII) for use in the coupling reaction is preferably 1 mmol/L to 1 mol/L at the start of the reaction.

Examples of a condensation reagent for use in the condensation reaction include carbodiimides such as dicyclohexylcarbodiimide, diisopropylcarbodiimide, or 1-ethyl-3-(3-dimethylaminopropyl)carbodiimide hydrochloride; ethyl chloroformate, oxalyl chloride, 2-(7-aza-1H-benzotriazol-1-yl)-1,1,3,3-tetramethyluronium hexafluorophosphate, O-(benzotriazol-1-yl)-N,N,N',N'-tetramethyluronium hexafluorophosphate, 1H-benzotriazol-1-yloxytripyrrolidinophosphonium hexafluorophosphate, or 2-methyl-6-nitrobenzoic acid anhydride, and preferably include carbodiimides such as dicyclohexylcarbodiimide, diisopropylcarbodiimide, or 1-ethyl-3-(3-dimethylaminopropyl)carbodiimide hydrochloride; or 2-(7-aza-1H-benzotriazol-1-yl)-1,1,3,3-tetramethyluronium hexafluorophosphate.

The amount of the condensation reagent for use in the condensation reaction is preferably 0.1 to 100 equivalents, more preferably 0.3 to 30 equivalents, to the carboxylic acid derivative (XII).

A reaction solvent for use in the condensation reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include chlorine-based solvents such as dichloromethane, chloroform, or 1,2-dichloroethane; or aprotic polar solvents such as N,N-dimethylformamide, N,N-dimethylacetamide, N-methyl-2-pyrrolidone, or dimethyl sulfoxide.

The condensation reaction may optionally be performed with a base. Examples of the base to be used include inorganic bases such as sodium hydride, sodium hydrogen carbonate, or potassium carbonate; organic bases such as triethylamine, diisopropylethylamine, 4-dimethylaminopyridine, or pyridine; or mixtures thereof, and preferably include organic bases such as triethylamine, diisopropylethylamine, 4-dimethylaminopyridine, or pyridine; or mixtures thereof.

The amount of the base for use in the condensation reaction is preferably 0.5 to 20 equivalents, more preferably 1 to 5 equivalents, to the carboxylic acid derivative (XII).

The reaction temperature of the condensation reaction is preferably −40° C. to 200° C., more preferably −20° C. to 150° C.

The reaction time of the condensation reaction is appropriately selected depending on the conditions such as reaction temperature, and is preferably 30 minutes to 30 hours.

The concentration of the carboxylic acid derivative (XII) for use in the condensation reaction is preferably 1 mmol/L to 1 mol/L at the start of the reaction.

The prodrug (XIX) of the peptide derivative (I) can be obtained, for example, by deprotection of the protected polyethylene glycol derivative (XVIII) followed by coupling reaction under basic to neutral conditions with the carboxylic acid derivative (XIV) (when G is succinimidyl or p-nitrophenyl) or by condensation reaction with the carboxylic acid derivative (XIV) (when G is a hydrogen atom), as shown in Scheme 13:

Scheme 13
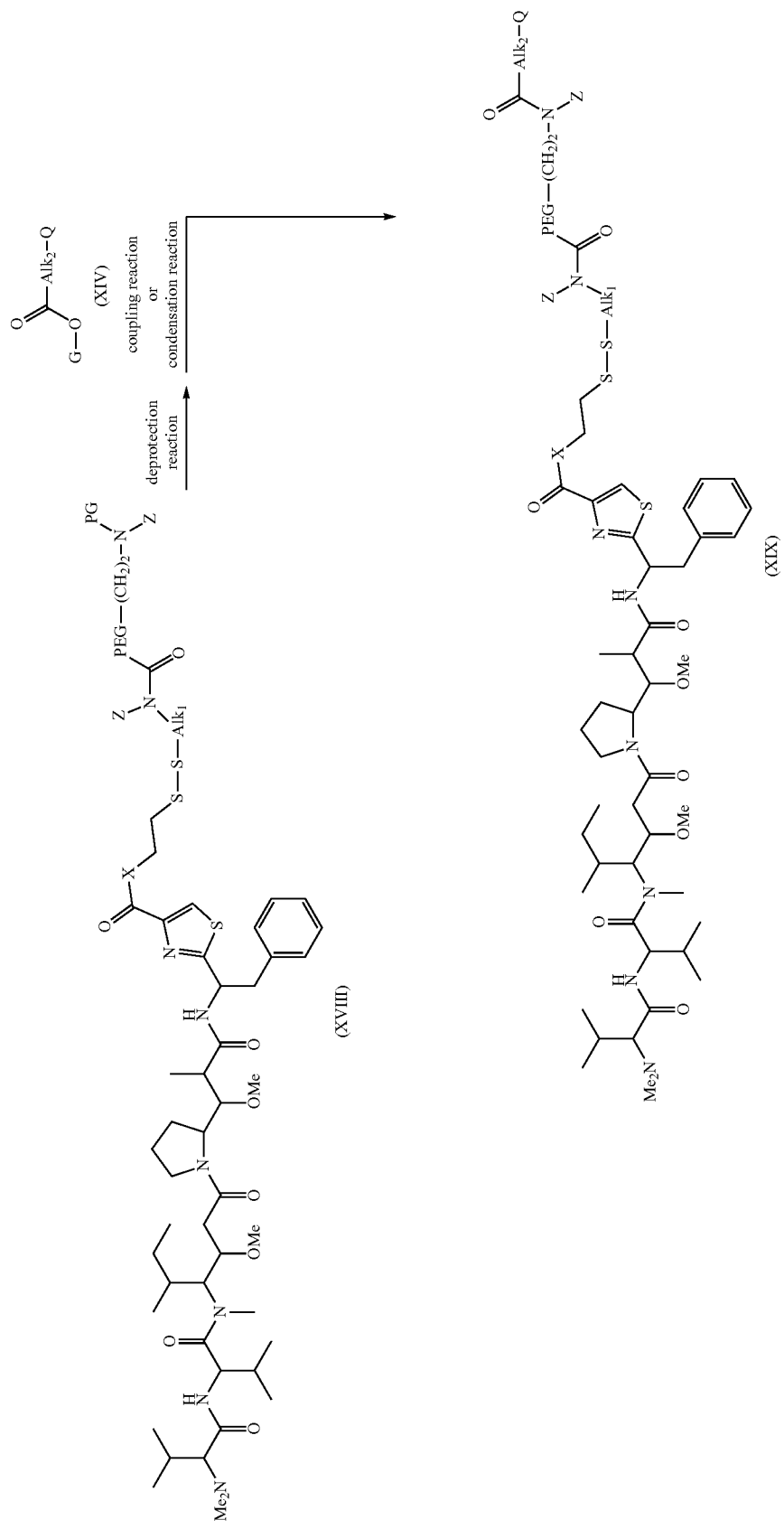

wherein each symbol is the same as the definition above.

Protective groups are removed in different ways depending on the type of the protective groups, but the deprotection may be performed according to known methods (for example, Greene, T. W., "Greene's Protective Groups in Organic Synthesis," Wiley-Interscience) or equivalent methods.

The amount of the carboxylic acid derivative (XIV) for use in the coupling reaction or condensation reaction is preferably 0.5 to 10 equivalents, more preferably 0.5 to 4 equivalents, to the protected polyethylene glycol derivative (XVIII).

Adjustment for pH of the coupling reaction can be made by a base. Examples of the base for use include organic bases such as triethylamine or diisopropylethylamine; inorganic bases such as sodium hydrogen carbonate or potassium carbonate; metal hydride compounds such as sodium hydride, potassium hydride, or calcium hydride; alkyl lithium such as methyl lithium or butyl lithium; lithium amide such as lithium hexamethyldisilazide or lithium diisopropylamide; or mixtures thereof, and preferably include inorganic bases such as sodium hydrogen carbonate or potassium carbonate; or organic bases such as triethylamine or diisopropylethylamine.

The amount of the base for use in the coupling reaction is preferably 0.001 to 10 equivalents, more preferably 0.001 to 4 equivalents, to the protected polyethylene glycol derivative (XVII).

Adjustment for pH of the coupling reaction can also be made by a buffer. Examples of the buffer for use include phosphate buffers, citrate buffers, citric acid-phosphate buffers, boric acid buffers, tartrate buffers, or Tris buffers, and preferably include buffers of pH 7.0 to 8.0.

The concentration of the buffer for use in the coupling reaction is preferably 10 mmol/L to 1 mol/L.

A reaction solvent for use in the coupling reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; water; or mixed solvents thereof, and preferably include chlorine-based solvents such as dichloromethane, chloroform, or 1,2-dichloroethane; nitrile-based solvents such as acetonitrile or propionitrile; water; or mixed solvents thereof.

The reaction temperature of the coupling reaction is preferably −40° C. to 200° C., more preferably −20° C. to 150° C.

The reaction time of the coupling reaction is appropriately selected depending on the conditions such as reaction temperature, and is preferably 30 minutes to 30 hours.

The concentration of the carboxylic acid derivative (XIV) for use in the coupling reaction is preferably 1 mmol/L to 1 mol/L at the start of the reaction.

Examples of a condensation reagent for use in the condensation reaction include carbodiimides such as dicyclohexylcarbodiimide, diisopropylcarbodiimide, or 1-ethyl-3-(3-dimethylaminopropyl)carbodiimide hydrochloride; ethyl chloroformate, oxalyl chloride, 2-(7-aza-1H-benzotriazol-1-yl)-1,1,3,3-tetramethyluronium hexafluorophosphate, O-(benzotriazol-1-yl)-N,N,N',N'-tetramethyluronium hexafluorophosphate, 1H-benzotriazol-1-yloxytripyrrolidinophosphonium hexafluorophosphate, or 2-methyl-6-nitrobenzoic acid anhydride, and preferably include carbodiimides such as dicyclohexylcarbodiimide, diisopropylcarbodiimide, or 1-ethyl-3-(3-dimethylaminopropyl)carbodiimide hydrochloride; or 2-(7-aza-1H-benzotriazol-1-yl)-1,1,3,3-tetramethyluronium hexafluorophosphate.

The amount of the condensation reagent for use in the condensation reaction is preferably 0.1 to 100 equivalents, more preferably 0.3 to 30 equivalents, to the carboxylic acid derivative (XIV).

A reaction solvent for use in the condensation reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include chlorine-based solvents such as dichloromethane, chloroform, or 1,2-dichloroethane; or aprotic polar solvents such as N,N-dimethylformamide, N,N-dimethylacetamide, N-methyl-2-pyrrolidone, or dimethyl sulfoxide.

The condensation reaction may optionally be performed with a base. Examples of the base to be used include inorganic bases such as sodium hydride, sodium hydrogen carbonate, or potassium carbonate; organic bases such as triethylamine, diisopropylethylamine, 4-dimethylaminopyridine, or pyridine; or mixtures thereof, and preferably include organic bases such as triethylamine, diisopropylethylamine, 4-dimethylaminopyridine, or pyridine; or mixtures thereof.

The amount of the base for use in the condensation reaction is preferably 0.5 to 20 equivalents, more preferably 1 to 5 equivalents, to the carboxylic acid derivative (XIV).

The reaction temperature of the condensation reaction is preferably −40° C. to 200° C., more preferably −20° C. to 150° C.

The reaction time of the condensation reaction is appropriately selected depending on the conditions such as reaction temperature, and is preferably 30 minutes to 30 hours.

The concentration of the carboxylic acid derivative (XIV) for use in the condensation reaction is preferably 1 mmol/L to 1 mol/L at the start of the reaction.

The prodrug (XX) of the peptide derivative (I) can be obtained, for example, by deprotection of the disulfide derivative (XVII-a) followed by coupling reaction under basic to neutral conditions with the carboxylic acid derivative (XIV) (when G is succinimidyl or p-nitrophenyl) or by condensation reaction with the carboxylic acid derivative (XIV) (when G is a hydrogen atom), as shown in Scheme 14:

Scheme 14
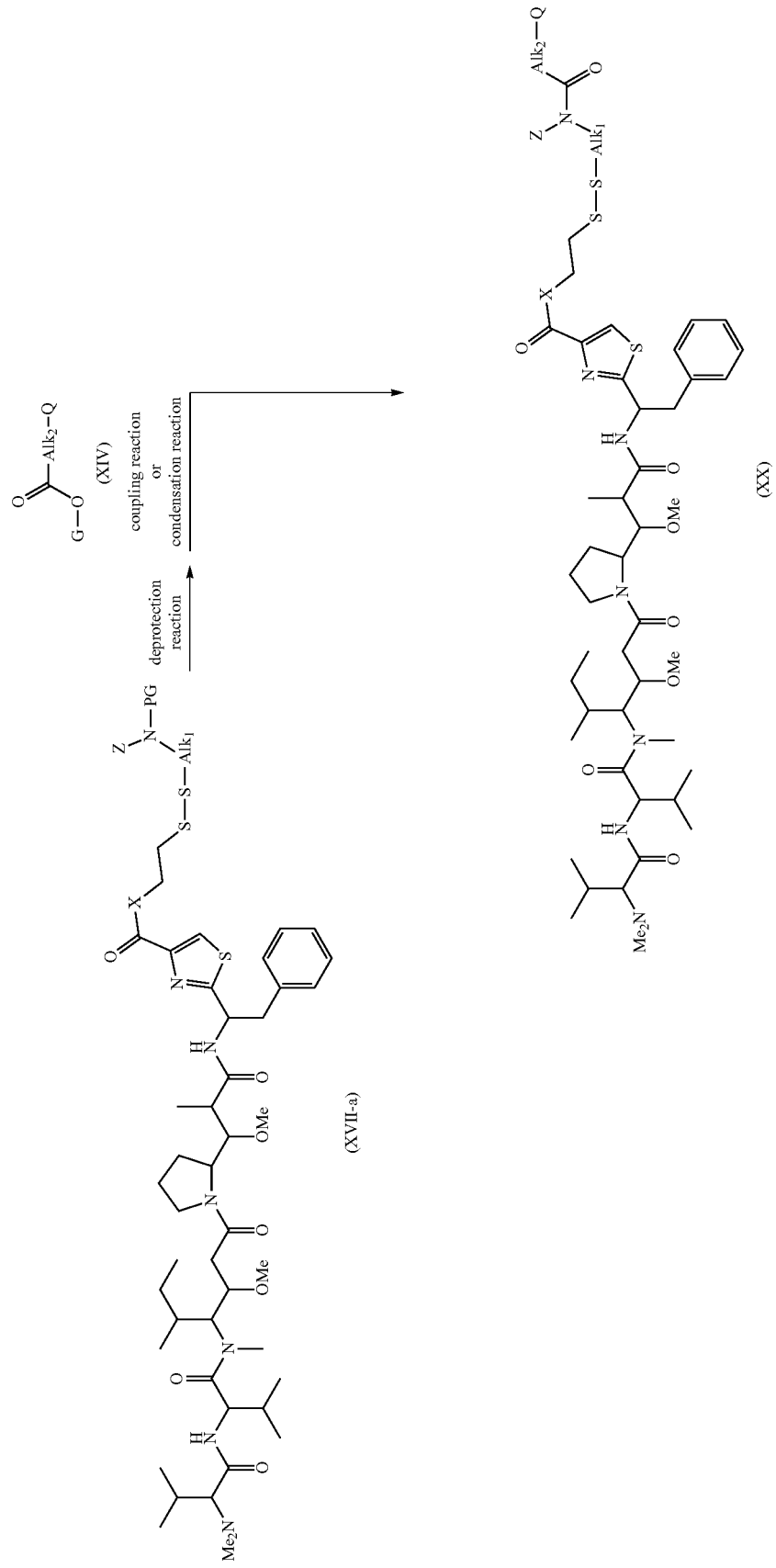

wherein each symbol is the same as the definition above.

Protective groups are removed in different ways depending on the type of the protective groups, but the deprotection may be performed according to known methods (for example, Greene, T. W., "Greene's Protective Groups in Organic Synthesis," Wiley-Interscience) or equivalent methods thereto.

The amount of the carboxylic acid derivative (XIV) for use in the coupling reaction or condensation reaction is preferably 0.5 to 10 equivalents, more preferably 0.5 to 4 equivalents, to the disulfide derivative (XVII-a).

Adjustment for pH of the coupling reaction can be made by a base. Examples of the base for use include organic bases such as triethylamine or diisopropylethylamine; inorganic bases such as sodium hydrogen carbonate or potassium carbonate; metal hydride compounds such as sodium hydride, potassium hydride, or calcium hydride; alkyl lithium such as methyl lithium or butyl lithium; lithium amide such as lithium hexamethyldisilazide or lithium diisopropylamide; or mixtures thereof, and preferably include inorganic bases such as sodium hydrogen carbonate or potassium carbonate; or organic bases such as triethylamine or diisopropylethylamine.

The amount of the base for use in the coupling reaction is preferably 0.001 to 10 equivalents, more preferably 0.001 to 4 equivalents, to the disulfide derivative (XVII-a).

Adjustment for pH of the coupling reaction can also be made by a buffer. Examples of the buffer for use include phosphate buffers, citrate buffers, citric acid-phosphate buffers, boric acid buffers, tartrate buffers, or Tris buffers, and preferably include buffers of pH 7.0 to 8.0.

The concentration of the buffer for use in the coupling reaction is preferably 10 mmol/L to 1 mol/L.

A reaction solvent for use in the coupling reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; water; or mixed solvents thereof, and preferably include chlorine-based solvents such as dichloromethane, chloroform, or 1,2-dichloroethane; nitrile-based solvents such as acetonitrile or propionitrile; water; or mixed solvents thereof.

The reaction temperature of the coupling reaction is preferably −40° C. to 200° C., more preferably −20° C. to 150° C.

The reaction time of the coupling reaction is appropriately selected depending on the conditions such as reaction temperature, and is preferably 30 minutes to 30 hours.

The concentration of the carboxylic acid derivative (XIV) for use in the coupling reaction is preferably 1 mmol/L to 1 mol/L at the start of the reaction.

Examples of a condensation reagent for use in the condensation reaction include carbodiimides such as dicyclohexylcarbodiimide, diisopropylcarbodiimide, or 1-ethyl-3-(3-dimethylaminopropyl)carbodiimide hydrochloride; ethyl chloroformate, oxalyl chloride, 2-(7-aza-1H-benzotriazol-1-yl)-1,1,3,3-tetramethyluronium hexafluorophosphate, O-(benzotriazol-1-yl)-N,N,N',N'-tetramethyluronium hexafluorophosphate, 1H-benzotriazol-1-yloxytripyrrolidinophosphonium hexafluorophosphate, or 2-methyl-6-nitrobenzoic acid anhydride, and preferably include carbodiimides such as dicyclohexylcarbodiimide, diisopropylcarbodiimide, or 1-ethyl-3-(3-dimethylaminopropyl)carbodiimide hydrochloride; or 2-(7-aza-1H-benzotriazol-1-yl)-1,1,3,3-tetramethyluronium hexafluorophosphate.

The amount of the condensation reagent for use in the condensation reaction is preferably 0.1 to 100 equivalents, more preferably 0.3 to 30 equivalents, to the carboxylic acid derivative (XIV).

A reaction solvent for use in the condensation reaction is appropriately selected depending on the type of reagents to be used, but it is not particularly limited as long as the reaction is not inhibited. Examples of the reaction solvent include aprotic polar solvents such as N,N-dimethylformamide, N,N-dimethylacetamide, N-methyl-2-pyrrolidone, or dimethyl sulfoxide; ether-based solvents such as diethyl ether, tetrahydrofuran, dimethoxyethane, or 1,4-dioxane; ester-based solvents such as ethyl acetate or propyl acetate; chlorine-based solvents such as dichloromethane, chloroform, or 1,2-dichloroethane; nitrile-based solvents such as acetonitrile or propionitrile; or mixed solvents thereof, and preferably include chlorine-based solvents such as dichloromethane, chloroform, or 1,2-dichloroethane; or aprotic polar solvents such as N,N-dimethylformamide, N,N-dimethylacetamide, N-methyl-2-pyrrolidone, or dimethyl sulfoxide.

The condensation reaction may optionally be performed with a base. Examples of the base to be used include inorganic bases such as sodium hydride, sodium hydrogen carbonate, or potassium carbonate; organic bases such as triethylamine, diisopropylethylamine, 4-dimethylaminopyridine, or pyridine; or mixtures thereof, and preferably include organic bases such as triethylamine, diisopropylethylamine, 4-dimethylaminopyridine, or pyridine; or mixtures thereof.

The amount of the base for use in the condensation reaction is preferably 0.5 to 20 equivalents, more preferably 1 to 5 equivalents, to the carboxylic acid derivative (XIV).

The reaction temperature of the condensation reaction is preferably −40° C. to 200° C., more preferably −20° C. to 150° C.

The reaction time of the condensation reaction is appropriately selected depending on the conditions such as reaction temperature, and is preferably 30 minutes to 30 hours.

The concentration of the carboxylic acid derivative (XIV) for use in the condensation reaction is preferably 1 mmol/L to 1 mol/L at the start of the reaction.

Furthermore, the conjugate characteristically includes the peptide derivative (I), and a targeting ligand or a polymer.

The term "targeting ligand" means a substance to transport a physiologically active compound containing the peptide derivative (I) to a specified cell. Examples of the targeting ligand include antigen-binding proteins, cytokines, or small molecular ligands.

The term "antigen-binding protein" means a protein with a binding property to a specified protein present on the cell surface. Examples of the antigen-binding protein include, but are not limited to, immunoglobulin molecules, single chain antibodies, scFvs, Fab fragments, F(ab') fragments, Diabodies, Tribodies, Affibodies, Affilins, Anticalins, Atrimers, Avimers, Bicyclic peptides, Cys-knots, DARPins, FN3s, Fynomers, Kunitz domains, or OBodies.

The term "cytokine" means interleukin, chemokine, interferon, a cell growth factor, a cytotoxic factor, a modified protein thereof or the like. Examples of the cytokine include, but are not limited to, Interleukin-2, Interleukin-2 fusion proteins, Interleukin-3, Interleukin-4, Interleukin-6, Interleukin-8, Interleukin-12, Interleukin-17, CCL1 to CCL28, CXCL1 to CXCL17, XCL1, XCL2, CX3CL1, Interferon-α, Interferon-β, Interferon-γ, Interferon-ω, Interferon-τ, consensus interferons, granulocyte-colony stimulating factors (GCSFs), granulocyte-macrophage colony-stimulating factors (GMCSFs), CD-40 ligands, luteinizing hormone-releasing hormones (LHRHs), insulin-like growth factors (IGFs), macrophage colony-stimulating factors (M-CSF), nerve growth factors (NGFs), platelet-derived growth factors, tissue growth factors, transforming growth factor-1s, vascular endothelial cell growth factors, leukemia inhibitory factors, keratinocyte growth factors (KGFs), glial growth factors (GGFs), tumor necrosis factors (TNFs), monocyte chemoattractant protein-1, or endothelial cell growth factors.

The term "small molecular ligand" means an organic compound or peptide derivative with a binding property to the specified protein that is present on the cell surface and that has a molecular weight of less than 1000. Examples of the small molecular ligand include, but are not limited to, biotins, folic acids, integrin inhibitors, cRGD, RGD, PSMA inhibitors, or VEGF inhibitors.

The term "polymer" means a high molecular organic compound constituted of a certain repetitive structure and has number average molecular weight of 1000 to 1000000. Examples of the polymer include polyethylene glycols, polyglutamic acids, polyamino acids, or polysaccharides, and preferably include polyethylene glycols or polyglutamic acids, and more preferably include polyethylene glycols with number average molecular weight of 20000 to 100000 or polyglutamic acids with number average molecular weight of 20000 to 100000.

The antigen-binding protein, the cytokine, and the peptide derivative above also include, for example, chemically synthesized compounds thereof, recombinants thereof, natural products thereof, glycosylated or nonglycosylated forms thereof, forms in which unnatural amino acids are introduced thereto, forms in which functional groups (e.g., aldehyde group or sulfhydryl group) are introduced thereto by chemical reactions such as oxidization or reduction or by enzymatic reactions, and bioactive fragments thereof.

The term "unnatural amino acid" means an amino acid present in the natural and is not included in amino acids constituting proteins (natural amino acids), which the unnatural mino acid means an amino acid present in the natural or produced by chemical synthesis, i.e., an amino acid present in the natural and is an amino acid not constituting proteins; an amino acid in which a natural amino acid is chemically modified; an amino acid not included in natural amino acids, which is produced by chemical synthesis; or the like. Specific examples of the unnatural amino acid include, but are not limited to, D-amino acids, citrulline, ornithine, (S)-2-amino-3-(3-methyl-3H-diazirin-3-yl)propanoic acid (also referred to as Photo-L-Leucine), (S)-2-amino-4-(3-methyl-3H-diazirin-3-yl)butanoic acid (also referred to as Photo-L-Methionine), (S)-3-(4-acetylphenyl)-2-aminopropanoic acid (also referred to as 4-acetyl-L-phenylalanine), or (S)-2-amino-3-(4-azidophenyl)propanoic acid (also referred to as 4-azido-L-phenylalanine).

The small molecular ligand above includes, as appropriate, analogues thereof, derivatives thereof, agonists thereof, antagonists thereof, inhibitors thereof, isomers thereof or the like.

The term "conjugate" means a substance that contains the peptide derivative (I) or a prodrug thereof, and the targeting ligand; a substance that contains the peptide derivative (I) or a prodrug thereof, and the polymer; or a substance that contains the peptide derivative (I) or a prodrug thereof, and the targeting ligand and the polymer (hereinafter, collectively referred to as the conjugate including peptide derivative (I)), each of which is directly bound one another, or indirectly bound via other substances (hereinafter, linkers).

Examples of the conjugate including peptide derivative (I) include antibody-drug conjugates in which the peptide derivative (I) or a prodrug thereof, and the immunoglobulin molecule are directly bound, or indirectly bound via the linker.

Furthermore, examples of the conjugate including peptide derivative (I) include small molecule-drug conjugates in which the peptide derivative (I) or a prodrug thereof, and the small molecular ligand are directly bound or indirectly bound via the linker.

Furthermore, examples of the conjugate including peptide derivative (I) include polymer-drug conjugates in which the peptide derivative (I) or a prodrug thereof, and the polymer are directly bound or indirectly bound via the linker.

Furthermore, examples of the conjugate including peptide derivative (I) include substances in which the polymer and the targeting ligand are, independently of each other, directly bound or indirectly bound via the linker to the peptide derivative (I) or a prodrug thereof.

Furthermore, examples of the conjugate including peptide derivative (I) include substances in which the peptide derivative (I) or a prodrug thereof and the targeting ligand are, independently of each other, directly bound or indirectly bound via the linker to the polymer.

Furthermore, examples of the conjugate including peptide derivative (I) include substances in which the peptide derivative (I) or a prodrug thereof and the polymer are, independently of each other, directly bound or indirectly bound via the linker to the targeting ligand.

The term "including peptide derivative (I)" means that the peptide derivative (I) or a prodrug thereof is directly bound by covalent bonds or indirectly bound via the linker to the targeting ligand and/or the polymer, according to known methods (e.g., Ellen M. Sletten et al., Angewante Chimie International Edition, (2009); 48: pp. 6974-6998; Greg T. Hermanson, "Bioconjugate Technique," Elsevier; Xi Chem et al., Organic & Biomolecular Chemistry, (2016); 14: pp. 5417-5439) or equivalent methods thereto. Specific examples of such covalent bonds include, but are not limited to, bonds by addition of a sulfhydryl group to a maleimide group; disulfide bonds; bonds by condensation of an amino group or a hydroxy group, and a carboxyl group; bonds by click reaction of an alkyne group and an azide group; bonds by condensation of an aminooxy group and a carbonyl group; or bonds by ene-type reaction of a diazo group and a phenol group, and preferably include bonds by addition of a sulfhydryl group to a maleimide group; disulfide bonds; bonds by condensation of an amino group or a hydroxy group, and a carboxyl group; or bonds by condensation of an aminooxy group and a carbonyl group.

The term "linker" means a structure that is obtained by reactions among the peptide derivative (I) or a prodrug thereof, the targeting ligand and the polymer, and a compound that has a functional group(s) (e.g., maleimide, carboxyl, activated carboxyl, carbonyl, aminooxy, hydrazide, diazo, alkyne, or hydroxy). Examples of such a compound that has the functional group(s) include, but are not limited to, N-Succinimidyl 4-(Maleimidomethyl)cyclohexanecarboxylate (SMCC), Sulfosuccinimidyl-4-(N-Maleimidomethyl)-cyclohexane-1-carboxylate (Sulfo-SMCC), N-Succinimidyl-4-(N-Maleimidomethyl)-cyclohexane-1-carboxy-(6-amidocaproate) (LC-SMCC), κ-Maleimidoundecanoic acid N-Succinimidyl ester (KMUA), γ-Maleimidobutyric acid N-Succinimidyl ester (GMBS), ε-Maleimidocaproic acid N-hydroxysuccinimide ester (EMCS), m-Maleimidobenzoyl-N-hydroxysuccinimide ester (MBS), N-(α-Maleimidoacetoxy)-succinimide ester (AMAS), Succinimidyl-6-(β-Maleimidopropionamido)hexanoate (SMPH), N-Succinimidyl 4-(p-Maleimidophenyl)-butyrate (SMPB), and N-(p-Maleimidophenyl)isocyanate (PMPI), N-Succinimidyl 4(2-pyridylthio)pentanoate (SPP), N-Succinimidyl (4-iodo-acetyl)aminobenzoate (SIAB), 6-Maleimidocaproyl (MC), Maleimidopropanoyl (MP), p-aminobenzyloxycarbonyl (PAB), and N-Succinimidyl 4(2-pyridylthio)butanoate (SPDB). Furthermore, the linkers indicated above may be appropriately used in combination.

The term "specified protein present on the cell surface" means a protein that increases expression on the cell surface in cancers, autoimmune diseases, or infectious diseases. Examples of the specified protein present on the cell surface include, but are not limited to, CD19, CD22, CD30, CD33, CD37, CD56, CD66e, CD70, CD74, CD79b, DLL-3, PSMA, GPNMB, Her2, CA6, CA9, Mesothelin, Nectin-4, SLC44A4, Cripto, folate receptors, STEAP-1, MUC16, NaPi2b, GCC, EGFRviii, 5T4, TROP-2, LIV-1, SLITRK6, Tissue Factors, Guanylyl Cyclase C, CEACAM5, integrin receptors, interleukin receptors, PSMA, chemokine receptors, interferon receptors, cell growth factor receptors, or cytotoxic factor receptors.

Examples of the pharmaceutically acceptable salt of the conjugate including peptide derivative (I) include the same salts as the pharmaceutically acceptable salts of the peptide derivative (I).

The conjugate including the peptide derivative (I) or a pharmaceutically acceptable salt thereof may be an anhydrate or may have formed a solvate such as hydrate. The solvate herein is preferably a pharmaceutically acceptable solvate. The pharmaceutically acceptable solvate may be any of a hydrate and non-hydrate, but preferably it is a hydrate. Examples of the solvent constituting the solvate include alcohol-based solvents such as methanol, ethanol, or n-propanol; N,N-dimethylformamide; dimethyl sulfoxide; or water.

Specific examples of the conjugate including the peptide derivative (I) are indicated in Table 4, but this disclosure is not limited thereto.

TABLE 4

| Number | Structural Formula |
|--------|-------------------|
| 1 | |
| 2 | |
| 3 | |

TABLE 4-continued

| Number | Structural Formula |
|---|---|
| 4 | (structure) |
| 5 | (structure) |
| 6 | (structure) |
| 7 | (structure) |
| 8 | (structure) |
| 9 | (structure) |

TABLE 4-continued

| Number | Structural Formula |
|---|---|
| 10 | 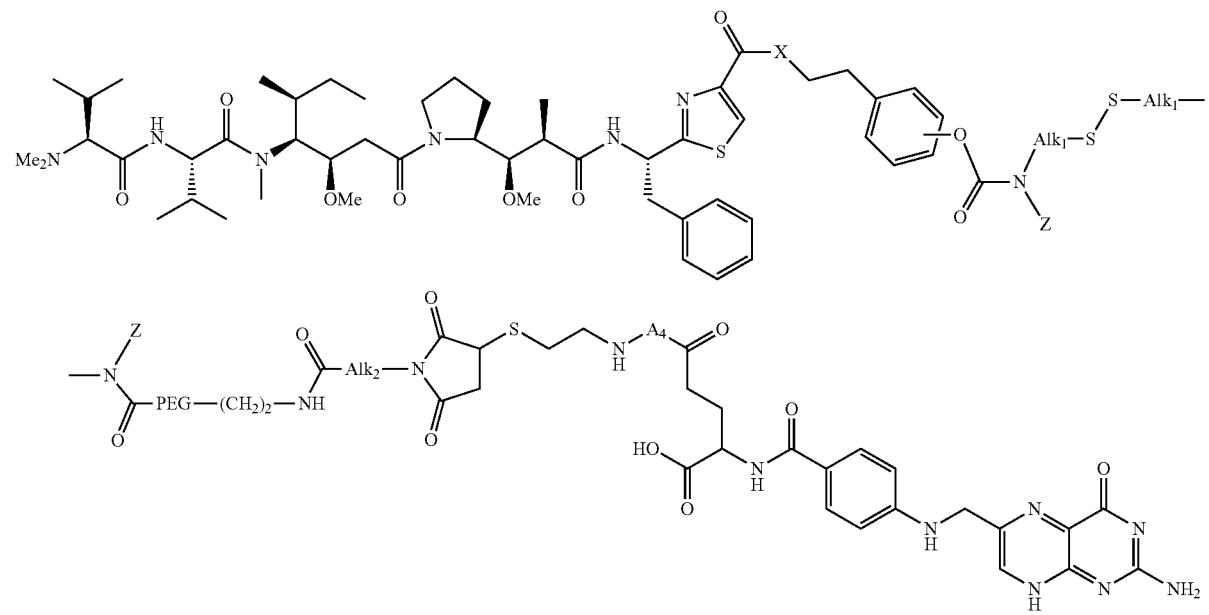 |
| 11 | |
| 12 | |

The compounds described in Table 4 also include pharmaceutically acceptable salts thereof.

In Table 4, r represents an integer of 1 to 50, L represents a targeting ligand, a polymer, or a polymer and targeting ligand, and the other symbols are the same as the definition above.

A preferred example of the conjugate described as Number 6 in Table 4 is represented by Formula (XXI), but this disclosure is not limited thereto:

(XXI)

wherein A$_4$ represents an amino acid, and the other symbols are the same as the definition above.

The left side of A$_4$ (one side to be bound to an amino group) is a carbonyl terminus, and the right side of A$_4$ (the other side to be bound to a carbonyl group) is an amino terminus. Furthermore, when A$_4$ is Lys, Glu, and Asp, A$_4$ may be bound by the amino or carboxyl group of the side chain thereof to the conjugate.

In the conjugate represented by Formula (XXI), more preferred are those in which X is NR, Alk$_1$ is —(CH$_2$)$_2$—, PEG is —(CH$_2$CH$_2$O)$_{12}$—, and A$_4$ is Glu that is bound by using the main chain thereof, and still more preferred are those in which X is NR, R and Z are methyl, Alk$_1$ and Alk$_2$ are —(CH$_2$)$_2$—, PEG is —(CH$_2$CH$_2$O)$_{12}$—, and A$_4$ is Glu that is bound by using the main chain thereof.

A preferred example of the conjugate described as Number 8 in Table 4 is represented by Formula (XXII), but this disclosure is not limited thereto:

(XXII)

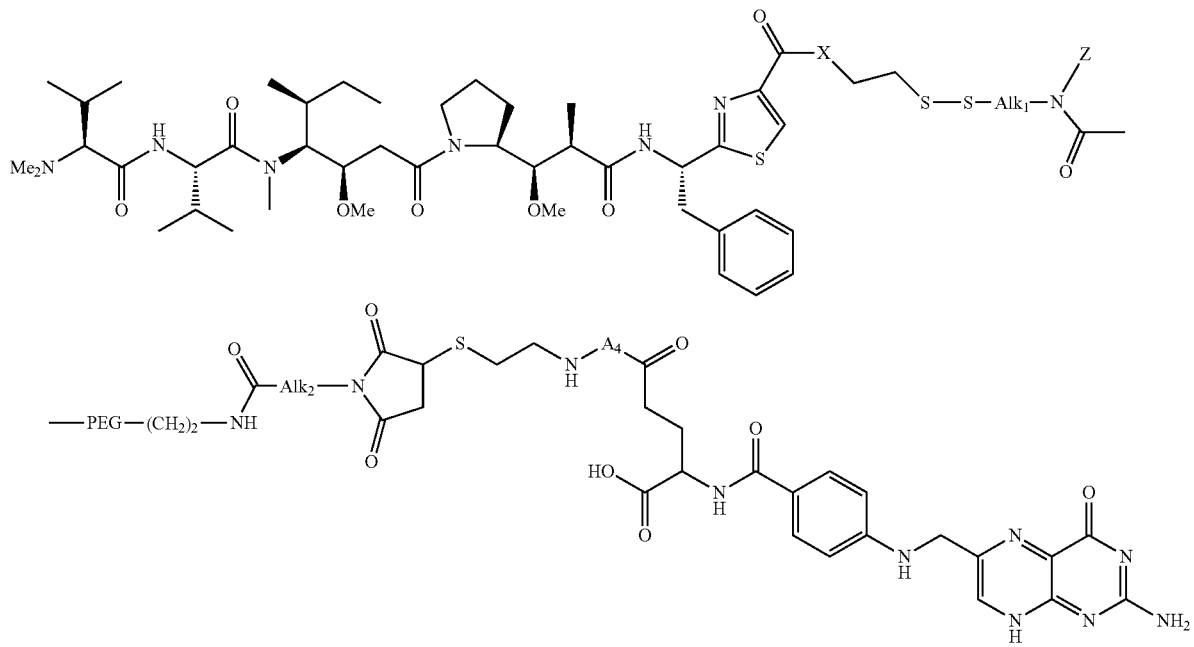

wherein each symbol is the same as the definition above.

In the conjugate represented by Formula (XXII), more preferred are those in which X is N(Me), Alk$_1$ is —(CH$_2$)$_2$—, PEG is —(CH$_2$CH$_2$O)$_{12}$—, and A$_4$ is Glu that is bound by using the main chain thereof, and still more preferred are those in which X is N(Me), Z is methyl, Alk$_1$ and Alk$_2$ are —(CH$_2$)$_2$—, PEG is —(CH$_2$CH$_2$O)$_{12}$—, and A$_4$ is Glu that is bound by using the main chain thereof.

The conjugate including the peptide derivative (I) can be produced by an appropriate method based on its basic skeleton and features derived from the types of substituents. In addition, the starting materials and reagents used for the production of these compounds are generally commercially available or can be produced by known methods or equivalent methods thereto.

The conjugate including the peptide derivative (I) as well as the intermediates and starting materials for use in the production of the derivative can be isolated and purified by known procedures. Examples of the known procedures for isolation and purification include solvent extraction, recrystallization, or chromatography.

If the conjugate including the peptide derivative (I) includes optical isomers or stereoisomers, each isomer can be obtained as a single compound by known methods. Examples of the known methods include crystallization, enzymatic resolution, or chiral chromatography.

The configuration of the conjugate represented by Formula (XXI) is preferably Formula (XXIII):

(XXIII)

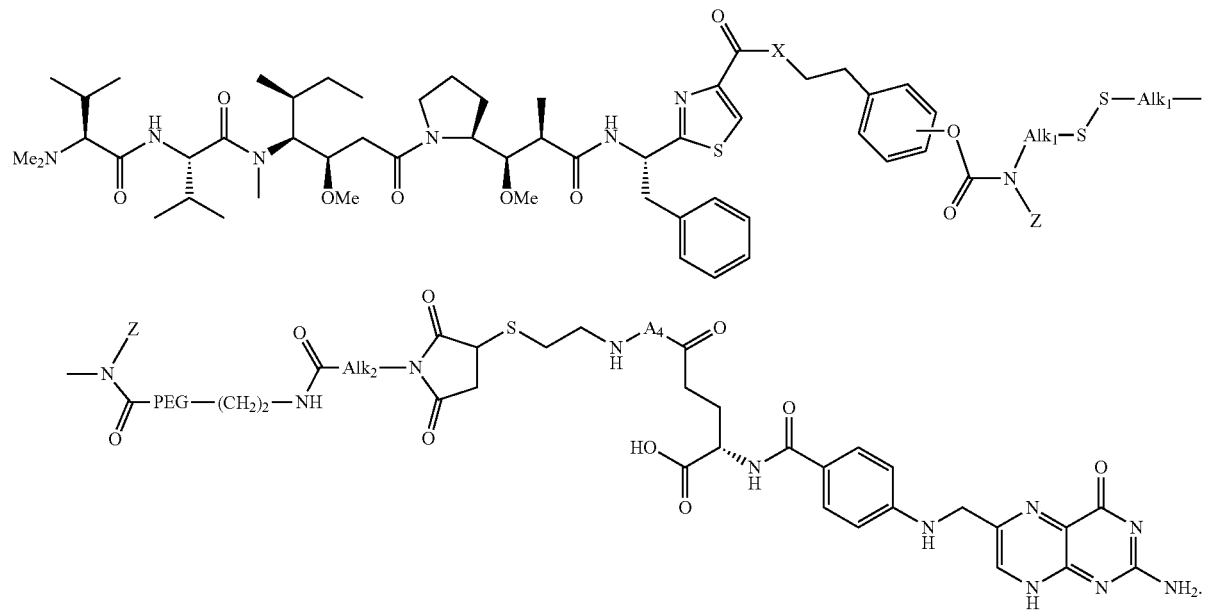

The configuration of the conjugate represented by Formula (XXII) is preferably Formula (XXIV):

(XXIV)

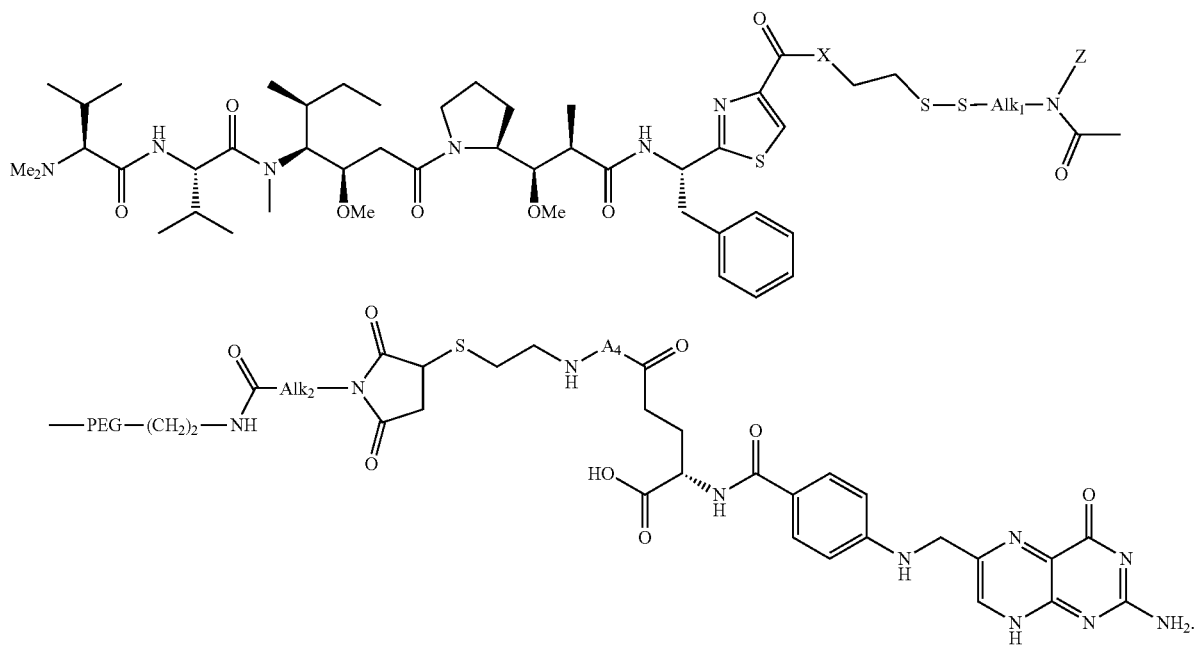

In the production method as described below, if any raw material compound has hydroxyl group, amino group, sulfhydryl group, or carboxyl group, a protective group may be introduced to each of these groups, and a desired compound can be obtained by removing the protective group as necessary subsequent to the reaction.

Examples of the protective group for the hydroxy group include trityl group, tetrahydropyranyl group, $C_7$-$C_{10}$ aralkyl group (for example, benzyl group), or substituted silyl group (for example, trimethylsilyl group, triethylsilyl group, or tert-butyldimethylsilyl group).

Examples of the protective group for the amino group include alkylcarbonyl group having $C_2$-$C_6$ alkylcarbonyl group (for example, acetyl), benzoyl group, $C_2$-$C_8$ alkyloxycarbonyl group (for example, tert-butoxycarbonyl group or benzyloxycarbonyl group), $C_7$-$C_{10}$ aralkyl group (for example, benzyl group), or phthaloyl group.

Examples of the protective group for the sulfhydryl group include trityl group, 2-mercaptopyridyl group, or 2-mercapto-5-nitropyridyl group.

Examples of the protective group for the carboxyl group include $C_1$-$C_6$ alkyl group (for example, methyl group, ethyl group, or tert-butyl group), or $C_7$-$C_{10}$ aralkyl group (for example, benzyl group).

Protective groups are removed in different ways depending on the type of the protective groups, but the deprotection may be performed according to known methods (for example, Greene, T. W., "Greene's Protective Groups in Organic Synthesis," Wiley-Interscience) or equivalent methods thereto.

The conjugate including the peptide derivative (I) can be obtained by conjugation, directly or indirectly via the linker, of the peptide derivative (I) or a prodrug thereof, or salts thereof, and the targeting ligand and/or the polymer above or salts thereof according to known methods (e.g., Ellen M. Sletten et al., Angewante Chimie International Edition, (2009); 48: pp. 6974-6998; Greg T. Hermanson., "Bioconjugate Technique," Elsevier; Xi Chem et al., Organic & Biomolecular Chemistry, (2016); 14: pp. 5417-5439) or equivalent methods thereto.

The conjugate including the peptide derivative (I) may be labeled with an isotope, and examples of the isotope used for labeling include $^2$H, $^3$H, $^{13}$C, $^{14}$C, $^{15}$N, $^{15}$O, $^{17}$O, $^{18}$O and/or $^{125}$I.

Examples of the salts of the peptide derivative (I) or a prodrug thereof, or the targeting ligand or the polymer used for the conjugation include inorganic acid salts such as hydrochloride, sulfate, nitrate, hydrobromide, hydroiodide, or phosphate; organic acid salts such as oxalate, malonate, citrate, fumarate, lactate, malate, succinate, tartrate, acetate, trifluoroacetate, maleate, gluconate, benzoate, ascorbate, glutarate, mandelate, phthalate, methanesulfonate, ethanesulfonate, benzenesulfonate, p-toluenesulfonate, camphorsulfonate, aspartate, glutamate, or cinnamate; salts with organic bases such as triethylamine salt, diisopropylethylamine salt, ethanolamine salt, morpholine salt, piperidine salt, or dicyclohexylamine salt; salts with basic amino acids such as arginine or lysine; or salts with inorganic bases such as lithium salt, calcium salt, potassium salt, sodium salt, ammonium salt, aluminum salt, or zinc salt.

The salts of the peptide derivative (I) or a prodrug thereof, or the targeting ligand or polymer may be an anhydrate or may have formed a solvate such as hydrate. Examples of the solvent constituting the solvate include alcohol-based solvents such as methanol, ethanol, or n-propanol; N,N-dimethylformamide, dimethyl sulfoxide, or water.

Furthermore, the cytotoxic agent characteristically includes, as an active ingredient, the peptide derivative (I) or a pharmaceutically acceptable salt thereof, or the conjugate including the peptide derivative (I) or a pharmaceutically acceptable salt thereof.

The term "cytotoxic agent" means a compound that causes cell death by impairing cell function or by inhibiting cell growth, or a composition that contains, as an active ingredient, a pharmaceutically acceptable salt thereof.

In addition, the term "cytotoxic agent" also includes a composition that contains, as an active ingredient, a conjugate including a compound that causes cell death by impairing cell function or by inhibiting cell growth, or a prodrug thereof, and the targeting ligand or polymer above, or a pharmaceutically acceptable salt thereof.

When administered to mammals (e.g., mice, rats, hamsters, rabbits, cats, dogs, monkeys, bovines, sheep, or humans), particularly to humans, the peptide derivative (I) or a pharmaceutically acceptable salt thereof, or the conjugate including the peptide derivative (I) or a pharmaceutically acceptable salt thereof can be used as a useful cytotoxic agent.

The peptide derivative (I) or a pharmaceutically acceptable salt thereof, or the conjugate including the peptide derivative (I) or a pharmaceutically acceptable salt thereof can be used alone or in combination with a pharmaceutically acceptable vehicle and be administered orally or parenterally to the mammals above as a cytotoxic agent.

Examples of "parenteral administration" include injections, transnasal, pulmonary, dermal, sublingual, or rectal administrations, and preferably include injections.

The term "injection" means that the cytotoxic agent is administered systemically or locally by injection or drip infusion. Examples of administration sites include intravenous sites, intramuscular sites, intraperitoneal sites, and subcutaneous sites.

The cytotoxic agent in which the peptide derivative (I) or a pharmaceutically acceptable salt thereof, or the conjugate including the peptide derivative (I) or a pharmaceutically acceptable salt thereof is an active ingredient can be produced by known methods in the art of pharmaceutical manufacturing (e.g., Remington's Pharmaceutical Science, latest edition, Mark Publishing Company, Easton, U.S.A). Furthermore, the cytotoxic agent can contain, as appropriate, additives in moderate amounts such as fillers, binders, disintegrants, lubricants, sweetening agents, surfactants, suspending agents, emulsifying agents, colorants, preservatives, flavoring agents, correctives, stabilizers, thickening agents, buffering agents, isotonic agents, glidants used in the art of pharmaceutical manufacturing. Examples of the pharmaceutically acceptable vehicle include these additives.

The cytotoxic agent in which the peptide derivative (I) or a pharmaceutically acceptable salt thereof, or the conjugate including the peptide derivative (I) or a pharmaceutically acceptable salt thereof is an active ingredient can be utilized as a therapeutic agent against diseases, for example, cancer, autoimmune diseases, or infectious diseases with which improvement of the clinical state or amelioration of symptoms of the diseases is expected based on the corresponding mechanism of action.

The term "cancer" means the disease caused by populations of cells that uncontrollably and abnormally proliferate. Examples of cancer include pharynx cancer, larynx cancer, tongue cancer, non-small cell lung cancer, breast cancer, esophagus cancer, gastric cancer, colorectal cancer, uterine cancer, endometrial cancer, ovarian cancer, liver cancer, pancreatic cancer, gallbladder cancer, bile duct cancer, kidney cancer, renal pelvis and ureter cancer, bladder cancer, prostate cancer, malignant melanoma, thyroid cancer, neurogenic or osteogenic sarcoma, chondrosarcoma, rhabdomyosarcoma, angiosarcoma, fibrosarcoma, glioma, leukemia or malignant lymphoma, neuroblastoma, myeloma, or brain tumor.

The term "autoimmune disease" means a disease that is caused by abnormal immune response to substances in living organisms or cells. Examples of autoimmune disease include active chronic hepatitis, Addison's disease, ankylosing spondylitis, antiphospholipid syndrome, arthritis, atopic allergy, Behcet's disease, cardiomyopathy, celiac disease, Cogan's syndrome, cold agglutinin disease, Crohn's disease, Cushing's syndrome, dermatomyositis, discoid lupus erythematosus, erythema, fibromyalgia, glomerulonephritis, Goodpasture's syndrome, graft-versus-host disease, Graves' disease, Guillain-Barre syndrome, Hashimoto's disease, idiopathic adrenal atrophy, idiopathic fibroid lung, IgA nephropathy, inflammatory bowel disease, insulin-dependent diabetes mellitus, juvenile arthritis, Lambert-Eaton myasthenic syndrome, lichen planus, lupoid hepatitis, lupus, lymphopenia, Meniere's disease, mixed connective-tissue disease, multiple sclerosis, myasthenia gravis, pernicious anemia, polyendocrine deficiency syndrome, primary biliary cirrhosis, psoriasis, psoriatic arthritis, Raynaud's phenomenon, Reiter's syndrome, articular rheumatism, Schmidt's syndrome, hidebound disease, Sjogren's syndrome, stiff-person syndrome, sympathetic ophthalmia, systemic lupus erythematosus, Takayasu arteritis, temporal arteritis, hyperthyroidism, type B insulin resistance, type I diabetes mellitus, ulcerative colitis, uveitis, leukoderma, or Wegener granulomatosis.

The term "infectious disease" means a disease caused by infection with bacteria, fungi, protozoan pathogens, yeasts, viruses or the like. Examples of causes of infectious disease include Staphylococci, Streptococcus, Enterococcus, Corynebacterium, Bacillus, Listeria, Peptococcus, Peptostreptococcus, Clostridium, Eubacterium, Propionibacterium, Lactobacillus, Neisseria, Branhamella, Haemophilus, Bordetella, Escherichia coli, Citrobacter, Salmonella, Shigella, Klebsiella, Enterobacter, Serratia, Hafnia, Proteus, Morganella, Providencia, Yersinia, campylobacter, Vibrio, Aeromonas, Pseudomonas, Xanthomonas, Acinetobacter, Flavobacterium, Brucella, Legionella, Veillonella, Bacteroides, Fusobacterium, Mycoplasma, Rickettsia, Chlamydia, Aspergillus, Cryptococcus, Candida, Mucor, Sporotrichum, dermatophyte, Plasmodium, Entamoeba histolytica, Trichomonas vaginalis, Pneumocystis carinii, Echinococcus, Diplococcus pneumoniae, Haemophilus influenzae, Mycobacterium tuberculosis, Clostridium tetani, adenoviruses, herpesviruses, papillomaviruses, AIDS viruses, filoviruses, Japanese encephalitis viruses, rabies viruses, polioviruses, rhinoviruses, influenza viruses, hepatitis B viruses, or hepatitis C viruses.

The cytotoxicity of the peptide derivative (I) or a pharmaceutically acceptable salt thereof, or the conjugate including the peptide derivative (I) or a pharmaceutically acceptable salt thereof can be evaluated with an in vitro study. Examples of the in vitro studies include the trypan blue dye exclusion method, the lactate dehydrogenase (LDH) activity assay, [³H]thymidine incorporation method, or propidium iodide nuclear stain that each measures the number of dead cells or surviving cells post treated with the compound; a method using dyes such as MTT, MTS, and WST (Current Protocol in Toxicology, (2000), 2.6.1-2.6.27); or a method in which the amount of ATP is measured using CellTiter-Glow (Promega Corporation) and the like, and preferably include the method in which the number of surviving cells post treated with the compound is measured by using the MTS method to determine values of the cytotoxicity at that time from 50% effect-concentration ($EC_{50}$). Furthermore, in the evaluation of the cytotoxicity of the conjugate including the peptide derivative (I) or a pharmaceutically acceptable salt thereof, preferred method is the one that for a certain time, cells are treated with a medium containing the compound, the cells are then transferred to a medium not containing the compound, and the number of surviving cells are measured after cultivation for additional certain time (Bioconjugate Chemistry., 2014; 25: pp. 560-568). For the in vitro studies, human ovarian cancer cell SKOV-3 cells, human alveolar basement epithelial gland cancer cell A549 cells, mouse lymphocytic leukocyte L1210 cells and the like are used.

The cell membrane permeability of the peptide derivative (I) or a pharmaceutically acceptable salt thereof can be measured with an in vitro evaluation method for cell membrane permeability. Examples of the in vitro evaluation method for cell membrane permeability include methods using a monolayer cell membrane system such as Caco-2 or Madin-Darby canine kidney (MDCK), or Parallel Artificial Membrane Permeation Assay (PAMPA) using an artificial lipid membrane in which lipid and the like are held on a filter (JP2007-118003A). More specifically, examples of the evaluation method for cell membrane permeability of the peptide derivative (I) or a pharmaceutically acceptable salt thereof include methods in which the amount of permeated compounds from a Donor side to an Acceptor side in Pre-coated PAMPA PlateSystem (Corning) is quantitated, and determined by calculation. The amount of permeated compounds can be quantitated by, for example, a liquid chromatograph mass spectrometer (hereinafter, LC/MS), absorbances, or fluorescent labels.

EXAMPLES

Our derivatives, uses and methods will be described in more details below by way of Examples and Reference Examples. However, this disclosure is not limited thereto.

For any compounds whose synthetic methods are not described in the context of the synthesis of the compounds of Examples, compounds commercially available or synthesized by known methods or equivalent methods thereto were used. The names of solvents indicated in the NMR data represent the solvents used for the measurements. The measurement of 400 MHz NMR spectrum was performed by using the JNM-AL400 nuclear magnetic resonance spectrometer (JEOL Ltd.) or the JNM-ECS400 nuclear magnetic resonance spectrometer (JEOL Ltd.). Chemical shifts were referenced to tetramethylsilane and expressed in 6 (unit: ppm), while the multiplicity of each signal was expressed as s (singlet), d (doublet), t (triplet), q (quartet), m (multiplet), br (broad), dd (double-doublet), dt (double-triplet), ddd (double-double-doublet), dq (double-quartet), or tt (triple-triplet). In $^1$H NMR spectra, signals that cannot be confirmed because of their broad peaks such as a proton of OH or NH were not described in data. Molecular weights were measured by electro-spray ionization (hereinafter, ESI) method using Agilent Technologies 1200 Series, 6130A (Agilent Technologies) (hereinafter, LC/MS-1), or Agilent Technologies 1260 Infinity II Series, 6130B (Agilent Technologies) (hereinafter, LC/MS-2). High-resolution mass spectrometry (HRMS) was performed by ESI using NexeraX2, LCMS-IT-TOF Mass Spectrometer (SHIMADZU CORPORATION). A retention time (hereinafter, $t_R$) was measured by high performance liquid chromatography (hereinafter, HPLC). All the used solvents were commercially available. For purification, YFLC W-prep2XY (YAMAZEN CORPORATION) was used; for silica gel column chromatography, Hi-Flash column silica gel (YAMAZEN CORPORATION) was used; for amine silica gel column chromatography, Hi-Flash column amino (YAMAZEN CORPORATION) was used; and for ODS column, Hi-Flash column Octadecyl $C_{18}$ standard (YAMAZEN CORPORATION) was used. Analytical conditions for LC/MS-1, LC/MS-2, and HPLC, and purification conditions for ODS column will be described in a later part. In the description of Examples and Reference Examples, the following abbreviations are used:

Trt: triphenylmethyl group; Boc: tert-butoxycarbonyl group; THP: tetrahydropyranyl group.

Reference Example 1: Synthesis of 2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)thiazole-4-carboxylic acid

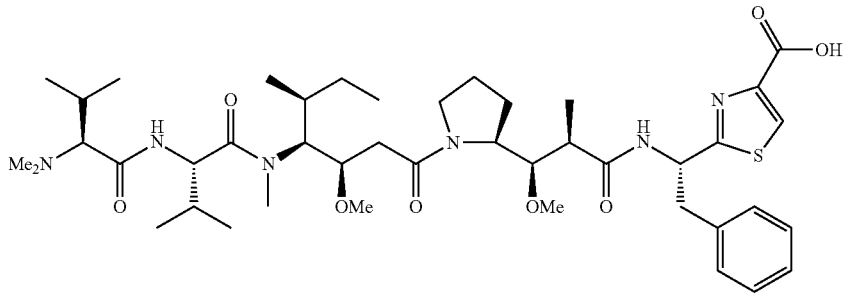 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)O)cs1)OC)N(C)C(=O)[C@@H](NC(=O)[C@H](C(C)C)N(C)C)C(C)C]

To a solution of ethyl 2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)thiazole-4-carboxylate (15 mg, 0.017 mmol) in ethanol (1.0 mL), 1.0 N sodium hydroxide (19 μL, 0.019 mmol) was added, and the resultant stirred at room temperature for three hours. To the obtained reaction solution, 1.0 N hydrochloric acid (19 μL) was added, the mixture then diluted with water, and the obtained solution was extracted three times with chloroform. The organic layers were dried over anhydrous sodium sulfate and then concentrated under vacuum to obtain the captioned compound (14 mg, 99% yield) (hereinafter referred to as the compound of Reference Example 1) as a white solid.

$^1$H-NMR (400 MHz, CDCl$_3$) δ: 7.97 (1H, s), 7.70-7.42 (1H, m), 7.30-7.15 (5H, m), 7.13-7.09 (1H, m), 5.62-5.55 (1H, m), 4.87-4.67 (2H, m), 4.11-3.10 (7H, m), 3.32 (3H×2, s), 3.04 (3H, s), 2.70-2.28 (4H, m), 2.53 (6H, s), 2.19-2.06 (2H, m), 1.98-1.55 (4H, m), 1.40-1.20 (1H, m), 1.18-0.69 (23H, m).

MS m/z (ESI) [M+H]$^+$: 829. (LC/MS-1)

Reference Example 2: Synthesis of 2-((S)-1-(((2S,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-(2-(tritylthio)ethyl)thiazole-4-carboxamide To a solution of the compound of Reference Example 1 (25 mg, 0.030 mmol) in N,N-dimethylformamide (hereinafter, DMF) (0.5 mL), a solution of 2-(7-aza-1H-benzotriazol-1-yl)-1,1,3,3-tetramethyluronium hexafluorophosphate (hereinafter, HATU) (17 mg, 0.045 mmol) and 2-(tritylthio)ethaneamine (15 mg, 0.045 mmol) in DMF (0.50 mL), and diisopropylethylamine (13 μL, 0.075 mmol) were added, and the mixture stirred at room temperature for one hour. To the obtained reaction solution, water was added, and the mixture extracted with ethyl acetate, washed with saturated brine, dried over anhydrous sodium sulfate, and then concentrated under vacuum. The residue was purified by silica gel column chromatography (methanol/chloroform=0/1→1/19) to obtain the captioned compound (23 mg, 88% yield) (hereinafter referred to as the compound of Reference Example 2) as a white solid.

$^1$H-NMR (400 MHz, CDCl$_3$) δ: 7.92 (1H, s), 7.45-7.13 (20H, m), 6.89 (1H, d, J=9.1 Hz), 5.54-5.47 (1H, m), 4.87-4.73 (2H, m), 4.16-4.09 (1H, m), 4.08-4.03 (1H, m), 3.87 (1H, d, J=8.6 Hz), 3.46-3.18 (6H, m), 3.33 (3H, s), 3.31 (3H, s), 3.03 (3H, s), 2.51 (2H, t, J=6.6 Hz), 2.45-2.30 (4H, m), 2.25 (6H, s), 2.10-1.90 (2H, m), 1.81-1.55 (4H, m), 1.27-1.19 (1H, m), 1.10 (3H, d, J=6.8 Hz), 1.07-0.89 (17H, m), 0.81 (3H, t, J=7.5 Hz).

MS m/z (ESI) [M+H]$^+$: 1130. (LC/MS-1)

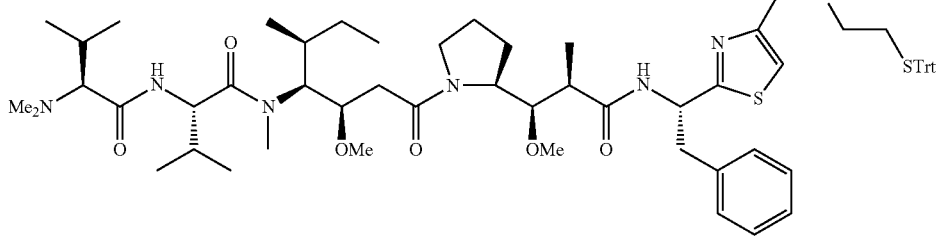

Example 1: Synthesis of 2-((S)-1-(((2S,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-(2-(mercaptoethyl)thiazole-4-carboxamide

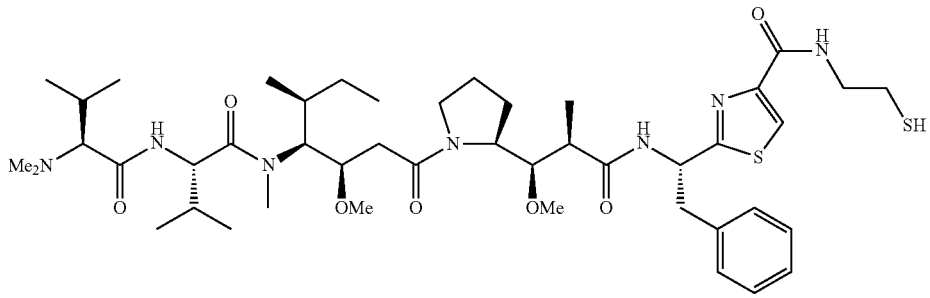

To the compound of Reference Example 2 (25 mg, 0.022 mmol), a solution of trifluoroacetic acid (hereinafter, TFA)/dichloromethane (volume ratio 1:1) (4.5 mL) containing 0.02 M triethylsilane was added, and the mixture stirred at room temperature for one hour. The solvent of the obtained reaction solution was evaporated under vacuum, a saturated aqueous solution of sodium carbonate added thereto, and the mixture extracted with ethyl acetate. The organic layer was washed with saturated brine, dehydrated over anhydrous sodium sulfate, and then concentrated under vacuum. The residue was purified by silica gel column chromatography (methanol/chloroform=0/1→1/9) to obtain the captioned compound (18 mg, 92% yield) (hereinafter referred to as the compound of Example 1) as a white solid.

$^1$H-NMR (400 MHz, CDCl$_3$) δ: 7.97 (1H, s), 7.70 (1H, t, J=6.1 Hz), 7.49 (1H, brs), 7.29-7.12 (5H, m), 6.90 (1H, d, J=8.2 Hz), 5.54-5.48 (1H, m), 4.82-4.74 (2H, m), 4.14-4.03 (2H, m), 3.86 (1H, d, J=7.7 Hz), 3.63 (2H, q, J=6.5 Hz), 3.51-3.16 (4H, m), 3.33 (3H, s), 3.32 (3H, s), 3.04 (3H, s), 2.81-2.74 (2H, m), 2.48-2.33 (4H, m), 2.25 (6H, s), 2.11-1.92 (2H, m), 1.85-1.60 (4H, m), 1.46 (1H, t, J=8.6 Hz), 1.40-1.22 (1H, m), 1.10 (3H, d, J=7.2 Hz), 1.05-0.90 (17H, m), 0.81 (3H, t, J=7.5 Hz).

MS m/z (ESI) [M+H]$^+$: 888. (LC/MS-1)

Reference Example 3: Synthesis of 2-(tritylthio)ethyl 2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)thiazole-4-carboxylate To a solution of the compound of Reference Example 1 (39 mg, 0.047 mmol) in dichloromethane (1.0 mL), 4-dimethylaminopyridine (hereinafter, DMAP) (1.2 mg, 9.4 μmol), triethylamine (14 μL, 0.10 mmol), and 2-methyl-6-nitrobenzoic acid anhydride (19 mg, 0.056 mmol) were added, and the mixture stirred at room temperature for 10 minutes, 2-(tritylthio)ethanol (18 mg, 0,056 mmol) was then added thereto, and the mixture stirred at room temperature for 20 hours. To the obtained reaction solution, water was added, and the mixture extracted three times with chloroform. The organic layers were dehydrated over anhydrous sodium sulfate and then concentrated under vacuum. The residue was purified by silica gel column chromatography (methanol/chloroform=0/1→2/25) to obtain the captioned compound (49 mg, 92% yield) (hereinafter referred to as the compound of Reference Example 3) as a white solid.

$^1$H-NMR (400 MHz, CDCl$_3$) δ: 8.00 (1H, s), 7.44-7.40 (6H, m), 7.37 (1H, d, J=7.8 Hz), 7.30-7.10 (14H, m), 6.90 (1H, d, J=9.6 Hz), 5.55-5.46 (1H, m), 4.79 (2H, t, J=48.0 Hz), 4.15-4.07 (1H, m), 4.11 (2H, t, J=6.9 Hz), 4.05-4.00 (1H, m), 3.87 (1H, d, J=7.8 Hz), 3.80-3.15 (4H, m), 3.32 (3H, s), 3.31 (3H, s), 3.02 (3H, s), 2.61 (2H, t, J=6.9 Hz), 2.45-2.28 (4H, m), 2.24 (6H, s), 2.12-1.96 (2H, m), 1.90-1.50 (4H, m), 1.40-1.30 (1H, m), 1.09 (3H, d, J=6.9 Hz), 1.03-0.89 (17H, m), 0.81 (3H, t, J=7.3 Hz).

MS m/z (ESI) [M+H]$^+$: 1131. (LC/MS-1)

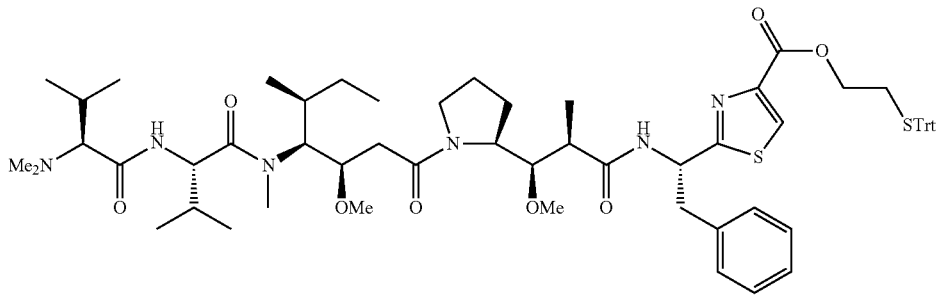

Example 2: Synthesis of 2-mercaptoethyl 2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)thiazole-4-carboxylate

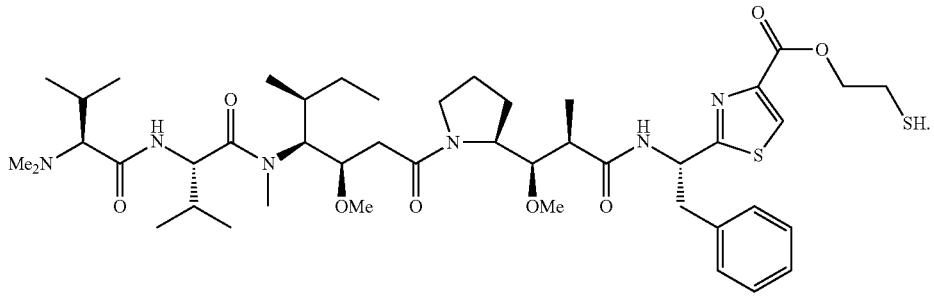 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)OCCS)cs1)OC)N(C)C(=O)[C@@H](NC(=O)[C@H](C(C)C)N(C)C)C(C)C]

The synthesis was performed by the same method as in Example 1 except that the compound of Reference Example 3 was used in place of the compound of Reference Example 2, to obtain the captioned compound (32 mg, 83% yield) (hereinafter, referred to as the compound of Example 2) as a white solid.

$^1$H-NMR (400 MHz, CDCl$_3$) δ: 8.07 (1H, s), 7.41 (1H, brs), 7.30-7.11 (5H, m), 6.90 (1H, d, J=9.1 Hz), 5.55-5.49 (1H, m), 4.83-4.74 (2H, m), 4.47 (2H, t, J=6.9 Hz), 4.13-3.11 (7H, m), 3.32 (6H, s), 3.03 (3H, s), 2.88 (2H, t, J=6.9 Hz), 2.47-2.28 (4H, m), 2.24 (6H, s), 2.11-1.98 (2H, m), 1.98-1.55 (4H, m), 1.41-1.30 (1H, m), 1.10 (3H, d, J=6.9 Hz), 1.05-0.91 (17H, m), 0.81 (3H, t, J=7.3 Hz).

MS m/z (ESI) [M+H]$^+$: 889. (LC/MS-1)

Reference Example 4: Synthesis of tert-butyl methyl(2-(tritylthio)ethyl)carbamate

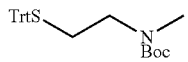

A solution of tert-butyl (2-(tritylthio)ethyl) carbamate (550 mg, 1.3 mmol) in DMF (10 ml) was cooled on ice, and sodium hydride (55 wt. % dispersion in mineral oil) (63 mg, 1.4 mmol) was added thereto in several parts. After stirring for 15 minutes, methyl iodide (0.087 ml, 1.4 mmol) was added, and the mixture stirred overnight while being allowed to room temperature. After adding an excess amount of ethyl acetate, the mixture was washed with a saturated aqueous solution of ammonium chloride and saturated brine, the resultant solution was dehydrated over anhydrous sodium sulfate, and then concentrated under vacuum. The obtained residue was purified by silica gel column chromatography (n-hexane/ethyl acetate=1/0→4/1) to obtain the captioned compound (420 mg, 96% yield) (hereinafter referred to as the compound of Reference Example 4) as a white solid.

$^1$H-NMR (400 MHz, CDCl$_3$) δ: 7.42 (d, J=8.2 Hz, 6H), 7.29 (t, J=7.5 Hz, 6H), 7.21 (t, J=7.3 Hz, 3H), 3.03 (t, J=7.5 Hz, 2H), 2.60 (brs, 3H), 2.33 (brs, 2H), 1.40 (s, 9H).

MS m/z (ESI) [M+Na]$^+$: 456. (LC/MS-1)

Reference Example 5: Synthesis of N-methyl-2-(tritylthio)ethan-1-amine

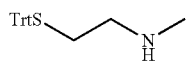

To a solution of Reference Example 4 (150 mg, 0.35 mmol) in dichloromethane (4.0 ml), 4 N hydrogen chloride-dioxane (3.0 ml) was added, and the mixture stirred at room temperature for four hours. To the reaction solution, an excess amount of dichloromethane containing 5% by volume of methanol was added, a saturated aqueous solution of sodium hydrogen carbonate added thereto, and the resultant solution dehydrated over anhydrous sodium sulfate, and then concentrated under vacuum. The captioned compound (15 mg, 40% yield) (hereinafter referred to as the compound of Reference Example 5) was obtained as an oily substance. The obtained oily substance was used for the next reaction without purification.

$^1$H-NMR (400 MHz, CDCl$_3$) δ: 7.44 (dd, J=10.7, 4.8 Hz, 6H), 7.32-7.26 (m, 6H), 7.24-7.19 (m, 3H), 3.71 (t, J=1.8 Hz, 1H), 3.07 (t, J=2.3 Hz, 1H), 2.51 (t, J=6.6 Hz, 1H), 2.36 (dd, J=11.2, 4.8 Hz, 1H), 2.29 (t, J=1.8 Hz, 3H), 1.50 (s, 2H).

MS m/z (ESI) [Trt]$^+$: 243. (LC/MS-1)

Reference Example 6: Synthesis of 2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-methyl-N-(2-(tritylthio)ethyl)thiazole-4-carboxamide

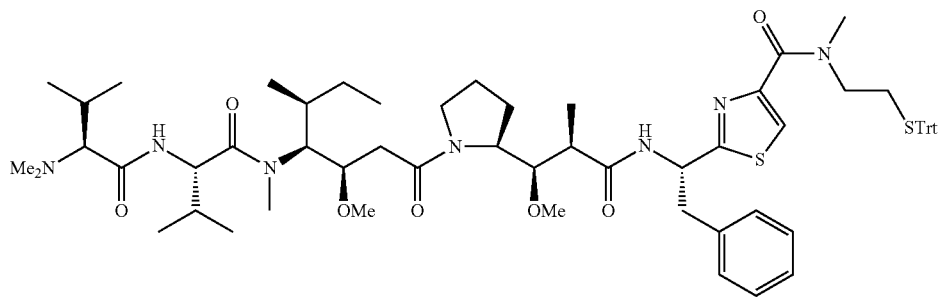

The synthesis was performed by the same method as in Reference Example 2 except that the compound of Reference Example 5 was used in place of 2-(tritylthio)ethanamine, to obtain the captioned compound (45 mg, 85% yield) (hereinafter, referred to as the compound of Reference Example 6) as a white amorphous.

$^1$H-NMR (400 MHz, CDCl$_3$) δ: 7.84 (1H, s), 7.82-7.76 (1H, m), 7.30-7.00 (5H, m), 6.92 (1H, d, J=9.1 Hz), 5.56-5.48 (1H, m), 5.07 (1H, brs), 4.87-4.70 (2H, m), 4.18-3.20 (17H, m), 3.10 (3H, s), 3.02 (3H, s), 2.45-2.20 (4H, m), 2.23 (6H, s), 2.11-1.89 (2H, m), 1.87-1.47 (4H, m), 1.40-1.30 (1H, m), 1.09 (3H, d, J=6.9 Hz), 1.05-0.86 (17H, m), 0.80 (3H, t, J=7.3 Hz).

MS m/z (ESI) [M+H]$^+$: 1144. (LC/MS-1)

Example 3: Synthesis of 2-((S)-1-(((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-(2-(mercaptoethyl)-N-methylthiazole-4-carboxamide

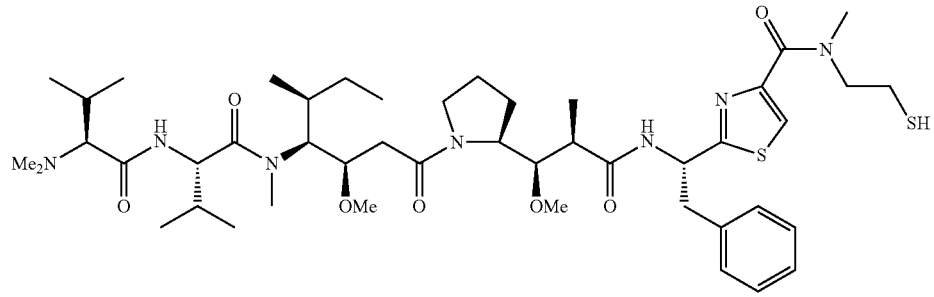

The synthesis was performed by the same method as in Example 1 except that the compound of Reference Example 6 was used in place of the compound of Reference Example 2, to obtain the captioned compound (27 mg, 77% yield) (hereinafter, referred to as the compound of Example 3) as a white amorphous.

$^1$H-NMR (400 MHz, CDCl$_3$) δ: 7.90 (1H, s), 7.60-7.45 (1H, m), 7.28-7.02 (5H, m), 6.90 (1H, d, J=9.1 Hz), 5.58-5.51 (1H, m), 4.82-4.74 (2H, m), 4.20-3.20 (9H, m), 3.33 (3H, s), 3.32 (3H, s), 3.11 (3H, s), 3.03 (3H, s), 2.91-2.77 (2H, m), 2.45-2.31 (4H, m), 2.24 (6H, s), 2.10-1.89 (2H, m), 1.86-1.60 (4H, m), 1.43-1.20 (1H, m), 1.11 (3H, d, J=6.9 Hz), 1.05-0.90 (17H, m), 0.81 (3H, t, J=7.3 Hz).

MS m/z (ESI) [M+H]$^+$: 902. (LC/MS-1)

Reference Example 7: Synthesis of 2-((tert-butoxycarbonyl)amino)ethyl 2-((S)-1-(((2S,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)thiazole-4-carboxylate

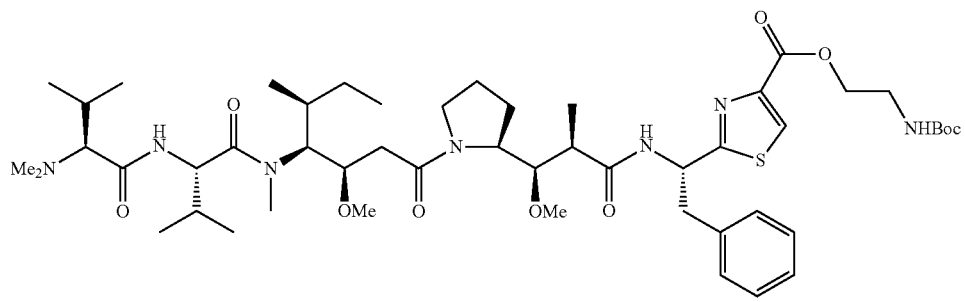 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)OCCNC(=O)OC(C)(C)C)cs1)OC)N(C)C(=O)[C@@H](NC(=O)[C@H](C(C)C)N(C)C)C(C)C]

To a solution of the compound of Reference Example 1 (38 mg, 0.046 mmol) in DMF (0.50 mL), HATU (21 mg, 0.055 mmol), a solution of tert-butyl (2-hydroxyethyl)carbamate (8.9 mg, 0.055 mmol) in DMF (0.50 mL), and diisopropylethylamine (7.5 μL, 0.069 mmol) were added at room temperature, and the mixture stirred at same temperature for 26 hours. To the obtained reaction solution, water added, and the mixture extracted with ethyl acetate. The organic layer was washed with saturated brine, dehydrated over anhydrous sodium sulfate, and then concentrated under vacuum. The residue was purified by silica gel column chromatography (methanol/chloroform=0/1→7/93) to obtain the captioned compound (14 mg, 32% yield) (hereinafter referred to as the compound of Reference Example 7) as a white solid.

$^1$H-NMR (400 MHz, CDCl$_3$) δ: 8.07 (1H, s), 7.44 (1H, brs), 7.30-7.12 (5H, m), 6.90 (1H, d, J=9.1 Hz), 5.55-5.49 (1H, m), 5.02 (1H, brs), 4.82-4.70 (2H, m), 4.41 (2H, t, J=4.6 Hz), 4.18-4.08 (1H, m), 4.05-4.00 (1H, m), 3.87 (1H, d, J=7.3 Hz), 3.70-3.14 (6H, m), 3.32 (3H, s), 3.31 (3H, s), 3.03 (3H, s), 2.48-2.33 (4H, m), 2.24 (6H, s), 2.13-1.87 (2H, m), 1.80-1.60 (4H, m), 1.43 (9H, s), 1.35-1.16 (1H, m), 1.10 (3H, d, J=7.3 Hz), 1.05-0.87 (17H, m), 0.81 (3H, t, J=7.3 Hz).

MS m/z (ESI) [M+H]$^+$: 972. (LC/MS-1)

Example 4: Synthesis of 2-aminoethyl 2-((S)-1-(((2S,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)thiazole-4-carboxylate

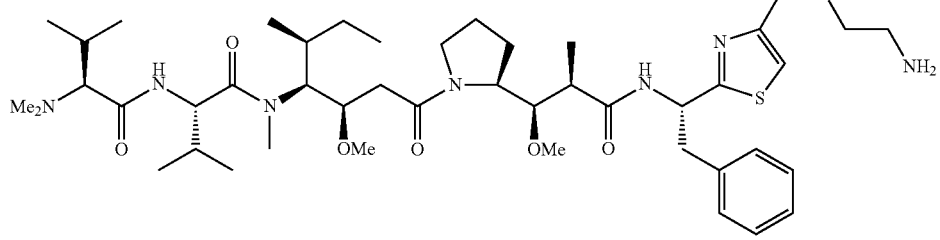

To a solution of the compound of Reference Example 7 (14 mg, 0.014 mmol) in methanol (1.0 mL), a 4 N solution of hydrogen chloride-dioxane (54 μL, 0.22 mmol) was added, and the mixture stirred at room temperature for 24 hours. The solvent of the obtained reaction solution was evaporated under vacuum, ethyl acetate added to the resultant, and the mixture washed with a saturated aqueous solution of sodium hydrogen carbonate, saturated brine. The organic layer was dehydrated over anhydrous sodium sulfate and then concentrated under vacuum. The residue was purified by amine silica gel column chromatography (methanol/chloroform=0/1-+1/19) to obtain the captioned compound (6.8 mg, 50% yield) (hereinafter referred to as the compound of Example 4) as a white solid.

$^1$H-NMR (400 MHz, CDCl$_3$) δ: 7.98 (1H, s), 7.78 (2H, brs), 7.54 (1H, brs), 7.32-7.00 (5H, m), 6.90 (1H, d, J=9.1 Hz), 5.51-5.45 (1H, m), 4.80-4.70 (2H, m), 4.18-4.00 (2H, m), 3.82 (2H, t, J=4.8 Hz), 3.80-3.10 (7H, m), 3.33 (3H, s), 3.32 (3H, s), 3.05 (3H, s), 2.52-2.30 (4H, m), 2.24 (6H, s), 2.14-1.92 (2H, m), 1.86-1.60 (4H, m), 1.40-1.19 (1H, m), 1.15-0.91 (20H, m), 0.82 (3H, t, J=6.4 Hz).

MS m/z (ESI) [M+H]$^+$: 872. (LC/MS-1)

Reference Example 8: Synthesis of tert-butyl (2-(2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-methylthiazole-4-carboxamido)ethyl)carbamate

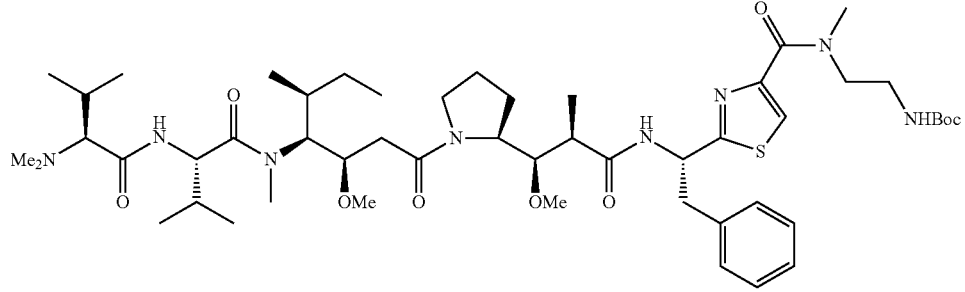 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)N(C)CCNC(=O)OC(C)(C)C)cs1)OC)N(C)C(=O)[C@@H](NC(=O)[C@H](C(C)C)N(C)C)C(C)C]

The synthesis was performed by the same method as in Reference Example 2 except that tert-butyl (2-(methylamino)ethyl)carbamate was used in place of 2-(tritylthio)ethanamine, to obtain the captioned compound (33 mg, 96% yield) (hereinafter, referred to as the compound of Reference Example 8) as a white solid.

¹H-NMR (400 MHz, CDCl₃) δ: 7.88-7.75 (1H, m), 7.70-7.60 (1H, m), 7.34-7.00 (5H, m), 6.90 (1H, d, J=8.7 Hz), 6.42-6.35 (1H, m), 5.63-5.48 (1H, m), 4.86-4.70 (2H, m), 4.18-4.00 (2H, m), 3.90-3.17 (9H, m), 3.32 (3H, s), 3.31 (3H, s), 3.09 (3H, s), 3.02 (3H, s), 2.45-2.30 (4H, m), 2.23 (6H, s), 2.17-1.85 (2H, m), 1.80-1.60 (4H, m), 1.35 (9H, s), 1.30-1.15 (1H, m), 1.10-0.86 (20H, m), 0.80 (3H, t, J=7.5 Hz).

MS m/z (ESI) [M+H]⁺: 985. (LC/MS-1)

Example 5: Synthesis of N-(2-aminoethyl)-2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-methylthiazole-4-carboxamide dihydro chloride

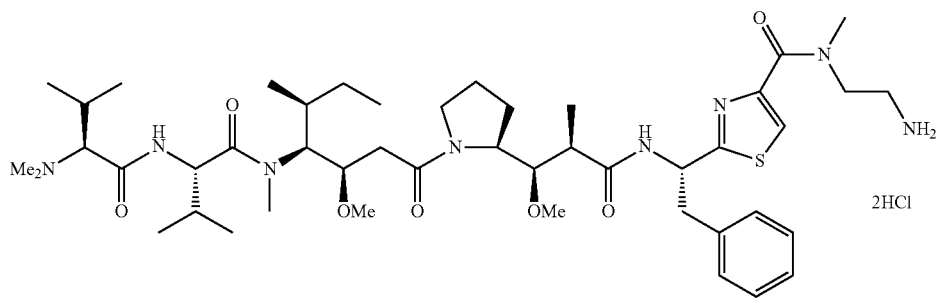 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)N(C)CCN)cs1)OC)N(C)C(=O)[C@@H](NC(=O)[C@H](C(C)C)N(C)C)C(C)C]

To a solution of the compound of Reference Example 8 (33 mg, 0.033 mmol) in methanol (1.0 mL), a 4 N solution of hydrogen chloride in dioxane (126 μL, 0.50 mmol) was added, and the mixture stirred at room temperature for 15 hours. The solvent of the obtained reaction solution was evaporated under vacuum to obtain the captioned compound (29 mg, 90% yield) (hereinafter, referred to as the compound of Example 5) as a white solid.

¹H-NMR (400 MHz, CD₃OD) δ: 8.98-8.60 (1H, m), 8.14-7.92 (1H, m), 7.37-7.18 (5H, m), 5.66-5.57 (1H, m), 4.85-4.63 (2H, m), 4.20-3.07 (20H, m), 3.16 (3H, s), 2.92 (3H, s), 2.91 (3H, s), 2.48-1.39 (10H, m), 1.30-0.98 (21H, m), 0.87 (3H, t, J=7.1 Hz).

MS m/z (ESI) [M+Na]⁺: 907. (LC/MS-1)

Reference Example 9: Synthesis of tert-butyl (2-(2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-methylthiazole-4-carboxamido)ethyl)(methyl)carbamate

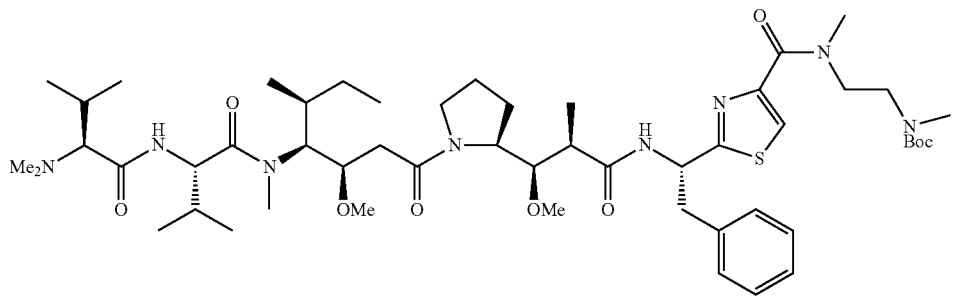 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)N(C)CCN(C)C(=O)OC(C)(C)C)cs1)OC)N(C)C(=O)[C@@H](NC(=O)[C@H](C(C)C)N(C)C)C(C)C]

The synthesis was performed by the same method as in Reference Example 2 except that tert-butyl methyl(2-(methylamino)ethyl)carbamate was used in place of 2-(tritylthio)ethanamine, to obtain the captioned compound (38 mg, 90% yield) (hereinafter, referred to as the compound of Reference Example 9) as a white amorphous.

¹H-NMR (400 MHz, CDCl₃) δ: 7.78 (1H, s), 7.70-7.40 (1H, brm), 7.30-7.11 (5H, m), 6.90 (1H, d, J=8.7 Hz), 5.57-5.48 (1H, m), 4.85-4.73 (2H, m), 4.18-4.00 (2H, m), 3.90-2.62 (12H, m), 3.33 (3H, s), 3.32 (3H, s), 3.13 (3H, s), 3.03 (3H, s), 2.45-2.30 (4H, m), 2.24 (6H, s), 2.13-1.90 (2H, m), 1.80-1.60 (4H, m), 1.45 (9H, s), 1.38-1.30 (1H, m), 1.16-0.91 (20H, m), 0.81 (3H, t, J=7.3 Hz).

MS m/z (ESI) [M+H]⁺: 999. (LC/MS-1)

Example 6: Synthesis of 2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-methyl-N-(2-(methylamine)ethyl)thiazole-4-carboxamide dihydrochloride

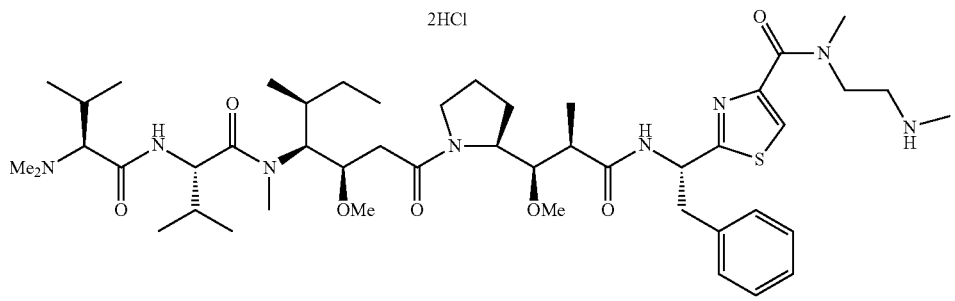 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)N(C)CCNC)cs1)OC)N(C)C(=O)[C@@H](NC(=O)[C@H](C(C)C)N(C)C)C(C)C]

The synthesis was performed by the same method as in Example 5 except that the compound of Reference Example 9 was used in place of the compound of Reference Example 8, to obtain the captioned compound (34 mg, 92% yield) (hereinafter, referred to as the compound of Example 6) as a white solid.

¹H-NMR (400 MHz, CD₃OD) δ: 8.15-8.02 (1H, m), 7.37-7.18 (5H, m), 5.66-5.57 (1H, m), 4.85-4.63 (2H, m), 4.20-3.07 (20H, m), 3.27 (3H, s), 3.15 (3H, s), 2.91 (3H, s), 2.89 (3H, s), 2.51-1.39 (10H, m), 1.30-0.87 (21H, m), 0.86 (3H, t, J=7.3 Hz).

MS m/z (ESI) [M+H]⁺: 899. (LC/MS-1)

Example 7: Synthesis of 2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-(2-(hydroxyethyl)thiazole-4-carboxamide

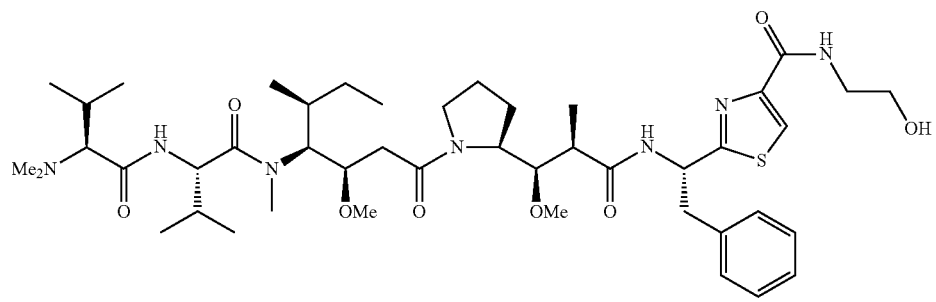 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)NCCO)cs1)OC)N(C)C(=O)[C@@H](NC(=O)[C@H](C(C)C)N(C)C)C(C)C]

The synthesis was performed by the same method as in Reference Example 2 except that 2-aminoethanol was used in place of 2-(tritylthio)ethanamine, to obtain the captioned compound (26 mg, quantitative yield) (hereinafter, referred to as the compound of Example 7) as a white solid.

$^1$H-NMR (400 MHz, CDCl$_3$) δ: 7.96 (1H, s), 7.85-7.75 (1H, m), 7.60 (1H, brs), 7.30-7.07 (5H, m), 6.91 (1H, d, J=8.7 Hz), 5.50-5.43 (1H, m), 4.83-4.72 (2H, m), 4.16-4.09 (1H, m), 4.05-4.01 (1H, m), 3.84-3.78 (3H, m), 3.65-3.20 (6H, m), 3.32 (3H, s), 3.31 (3H, s), 3.04 (3H, s), 2.48-2.32 (4H, m), 2.23 (6H, s), 2.16-1.63 (6H, m), 1.40-1.25 (1H, m), 1.08 (3H, d, J=6.9 Hz), 1.04-0.88 (17H, m), 0.80 (3H, t, J=6.4 Hz).

MS m/z (ESI) [M+H]$^+$: 872. (LC/MS-1)

Reference Example 10: Synthesis of 2-((tetrahydro-2H-pyran-2-yl)oxy)ethyl 2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)thiazole-4-carboxylate

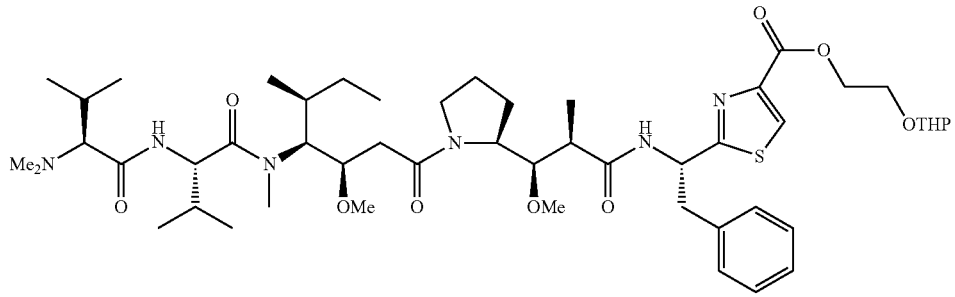

The synthesis was performed by the same method as in Reference Example 3 except that 2-(tetrahydro-2H-pyran-2-yl)oxy)ethanol was used in place of 2-(tritylthio)ethanol, to obtain the captioned compound (36 mg, 73% yield) (hereinafter, referred to as the compound of Reference Example 10) as a white solid.

$^1$H-NMR (400 MHz, CDCl$_3$) δ: 8.05 (1H, s), 7.36 (1H, d, J=6.9 Hz), 7.30-7.11 (5H, m), 6.89 (1H, d, J=9.6 Hz), 5.55-5.48 (1H, m), 4.83-4.75 (2H, m), 4.69 (1H, t, J=3.4 Hz), 4.60-4.46 (2H, m), 4.18-4.08 (1H, m), 4.07-4.00 (2H, m), 3.91-3.84 (2H, m), 3.82-3.75 (1H, m), 3.55-3.25 (5H, m), 3.33 (3H, s), 3.32 (3H, s), 3.02 (3H, s), 2.46-2.30 (4H, m), 2.24 (6H, s), 2.13-1.97 (2H, m), 1.93-1.51 (10H, m), 1.42-1.30 (1H, m), 1.10 (3H, d, J=6.9 Hz), 1.05-0.87 (17H, m), 0.81 (3H, t, J=7.5 Hz).

MS m/z (ESI) [M+H]$^+$: 957. (LC/MS-1)

Example 8: Synthesis of 2-hydroxyethyl 2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)thiazole-4-carboxylate

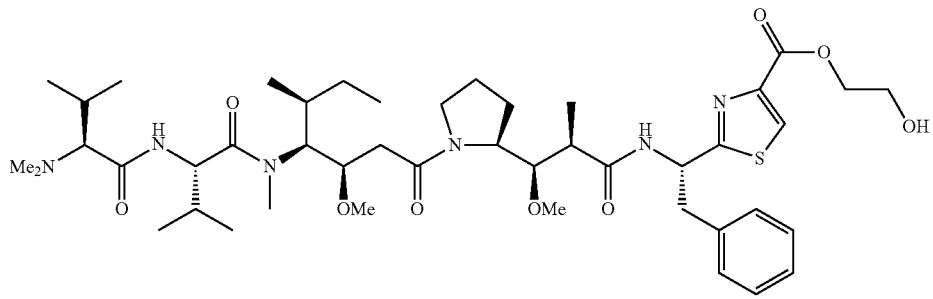 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)OCCO)cs1)OC)N(C)C(=O)[C@@H](NC(=O)[C@H](C(C)C)N(C)C)C(C)C]

To a solution of the compound of Reference Example 10 (36 mg, 0.038 mmol) in ethanol (1.0 mL), p-toluenesulfonic acid monohydrate (7.2 mg) was added, and the mixture stirred at room temperature for 18 hours. The solvent of the obtained reaction solution was evaporated under vacuum, the resultant diluted with dichloromethane, a saturated aqueous solution of potassium carbonate was added thereto, and the mixture extracted three times with chloroform. The organic layers were dehydrated over anhydrous sodium sulfate and then concentrated under vacuum. The residue was purified by silica gel column chromatography (methanol/chloroform=0/1→1/9) to obtain the captioned compound (31 mg, 95% yield) (hereinafter referred to as the compound of Example 8) as a white solid.

$^1$H-NMR (400 MHz, CDCl$_3$) δ: 8.10 (1H, s), 7.49-7.44 (1H, m), 7.30-7.13 (5H, m), 6.90 (1H, d, J=9.1 Hz), 5.55-5.48 (1H, m), 4.82-4.74 (2H, m), 4.50 (2H, t, J=4.6 Hz), 4.20-3.26 (9H, m), 3.33 (3H, s), 3.32 (3H, s), 3.02 (3H, s), 2.46-2.34 (4H, m), 2.24 (6H, s), 2.11-1.90 (2H, m), 1.84-1.60 (4H, m), 1.43-1.30 (1H, m), 1.09 (3H, d, J=7.3 Hz), 1.03-0.89 (17H, m), 0.81 (3H, t, J=7.5 Hz).

MS m/z (ESI) [M+H]$^+$: 873. (LC/MS-1)

Example 9: Synthesis of 2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-(2-(hydroxyethyl)-N-methylthiazole-4-carboxamide

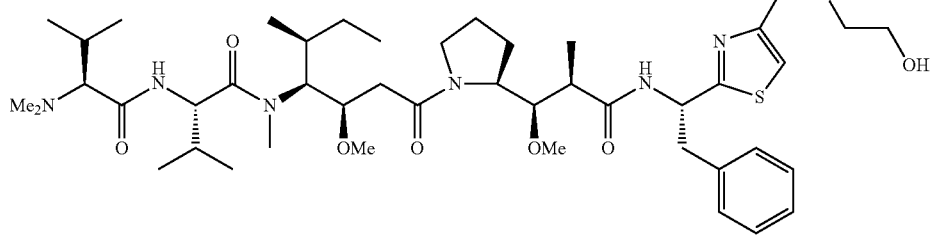

The synthesis was performed by the same method as in Reference Example 2 except that 2-(methylamino)ethan-1-ol was used in place of 2-(tritylthio)ethanamine, to obtain the captioned compound (31 mg, 85% yield) (hereinafter, referred to as the compound of Example 9) as a white amorphous.

$^1$H-NMR (400 MHz, CDCl$_3$) δ: 7.84 (1H, s), 7.82-7.76 (1H, m), 7.30-7.00 (5H, m), 6.92 (1H, d, J=9.1 Hz), 5.56-5.48 (1H, m), 5.07 (1H, brs), 4.87-4.70 (2H, m), 4.18-3.20 (17H, m), 3.10 (3H, s), 3.02 (3H, s), 2.45-2.20 (4H, m), 2.23 (6H, s), 2.11-1.89 (2H, m), 1.87-1.47 (4H, m), 1.40-1.30 (1H, m), 1.09 (3H, d, J=6.9 Hz), 1.05-0.86 (17H, m), 0.80 (3H, t, J=7.3 Hz).

MS m/z (ESI) [M+H]$^+$: 886. (LC/MS-1)

Example 10: Synthesis of N-(4-aminophenethyl)-2-((S)-1-(((2S,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)thiazole-4-carboxamide

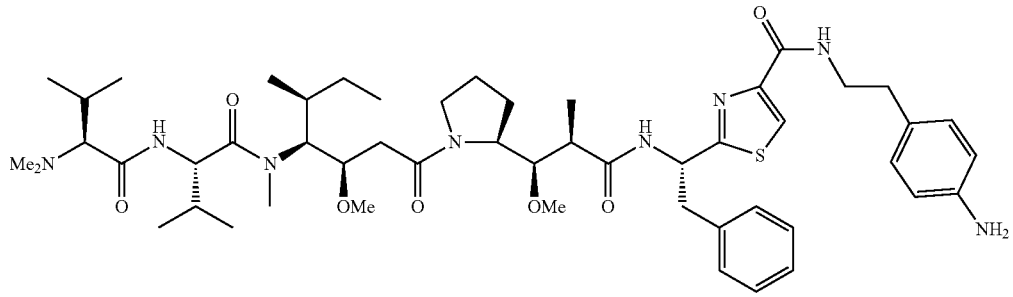 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)NCCc2ccc(N)cc2)cs1)OC)N(C)C(=O)[C@@H](NC(=O)[C@H](C(C)C)N(C)C)C(C)C]

The synthesis was performed by the same method as in Reference Example 2 except that 4-(2-aminoethyl)aniline was used in place of 2-(tritylthio)ethanamine, to obtain the captioned compound (37 mg, 74% yield) (hereinafter, referred to as the compound of Example 10) as a white solid.

$^1$H-NMR (400 MHz, CDCl$_3$) δ: 7.95 (1H, s), 7.43-7.36 (2H, m), 7.30-7.17 (5H, m), 7.04 (2H, d, J=8.2 Hz), 6.89 (1H, d, J=9.1 Hz), 6.65 (2H, d, J=8.2 Hz), 5.53-5.46 (1H, m), 4.83-4.72 (2H, m), 4.15-4.09 (1H, m), 4.08-4.03 (1H, m), 3.87 (1H, d, J=8.2 Hz), 3.70-3.18 (6H, m), 3.33 (3H, s), 3.31 (3H, s), 3.03 (3H, s), 2.82 (2H, t, J=7.1 Hz), 2.45-2.35 (4H, m), 2.24 (6H, s), 2.18-1.89 (2H, m), 1.84-1.64 (4H, m), 1.40-1.20 (1H, m), 1.10 (3H, d, J=7.3 Hz), 1.03-0.90 (17H, m), 0.81 (3H, t, J=7.3 Hz).

MS m/z (ESI) [M+H]$^+$: 947. (LC/MS-1)

Example 11: Synthesis of 2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-(4-hydroxyphenethyl)thiazole-4-carboxamide

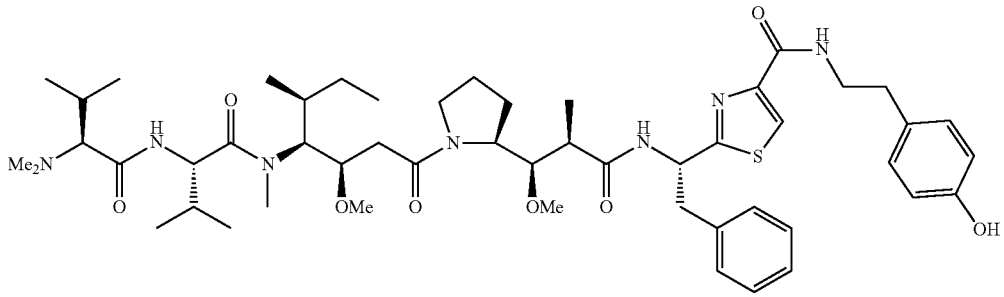 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)NCCc2ccc(O)cc2)cs1)OC)N(C)C(=O)[C@@H](NC(=O)[C@H](C(C)C)N(C)C)C(C)C]

The synthesis was performed by the same method as Reference Example 2 except that 4-(2-aminoethyl)phenol was used in place of 2-(tritylthio)ethanamine, to obtain the captioned compound (33 mg, quantitative yield) (hereinafter, referred to as the compound of Example 11) as a white solid.

$^1$H-NMR (400 MHz, CDCl$_3$) δ: 7.93 (1H, s), 7.41-7.30 (2H, m), 7.27-7.10 (5H, m), 7.04 (2H, d, J=8.2 Hz), 6.95-6.85 (1H, m), 6.82 (2H, d, J=8.2 Hz), 5.49-5.44 (1H, m), 4.85-4.72 (2H, m), 4.14-3.15 (9H, m), 3.33 (3H, s), 3.26 (3H, s), 3.03 (3H, s), 2.82 (2H, t, J=6.9 Hz), 2.51-2.30 (4H, m), 2.23 (6H, s), 2.17-1.94 (2H, m), 1.90-1.60 (4H, m), 1.40-1.20 (1H, m), 1.15-0.88 (20H, m), 0.80 (3H, t, J=7.3 Hz).

MS m/z (ESI) [M+H]$^+$: 949. (LC/MS-1)

Reference Example 11: Synthesis of tert-butyl(2-(2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)thiazole-4-carboxamido)ethyl)carbamate

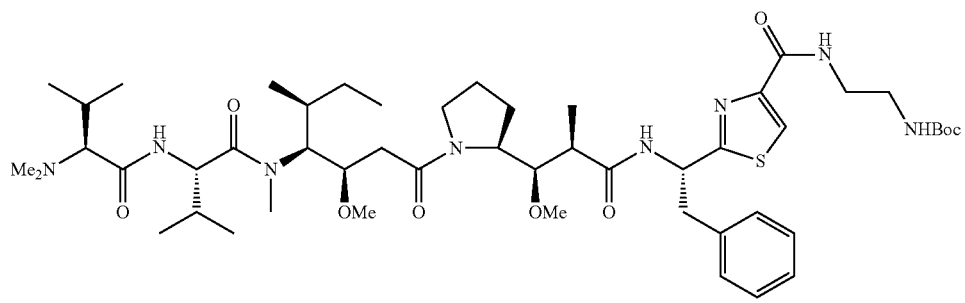 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)NCCNC(=O)OC(C)(C)C)cs1)OC)N(C)C(=O)[C@@H](NC(=O)[C@H](C(C)C)N(C)C)C(C)C]

The synthesis was performed by the same method as in Reference Example 2 except that tert-butyl(2-aminoethyl)carbamate was used in place of 2-(tritylthio)ethanamine, to obtain the captioned compound (55 mg, 98% yield) (hereinafter, referred to as the compound of Reference Example 11) as a white solid.

$^1$H-NMR (400 MHz, CDCl$_3$) δ (ppm): 7.96 (1H, s), 7.69 (1H, brs), 7.50 (1H, brs), 7.34-7.09 (5H, m), 6.90 (1H, d, J=9.1 Hz), 5.55-5.44 (1H, m), 5.03 (1H, brs), 4.89-4.67 (2H, m), 4.20-3.20 (11H, m), 3.33 (3H, s), 3.32 (3H, s), 3.04 (3H, s), 2.50-2.33 (4H, m), 2.25 (6H, s), 2.10-1.92 (2H, m), 1.85-1.66 (4H, m), 1.42 (9H, s), 1.40-1.20 (1H, m), 1.15-0.79 (23H, m).

MS m/z (ESI) [M+H]$^+$: 971. (LC/MS-1)

Reference Example 12: Synthesis of N-(2-aminoethyl)-2-((S)-1-(((2S,3R)-3-((S)-1-((3R,4S,5S)-4-((S)-2-((S)-2-(dimethylamino)-3-methylbutanamido)-N, 3-dimethylbutanamido)-3-methoxy-5-methylheptanoyl)pyrrolidin-2-yl)-3-methoxy-2-methylpropanamido)-2-phenylethyl)thiazole-4-carboxamide dihydrochloride

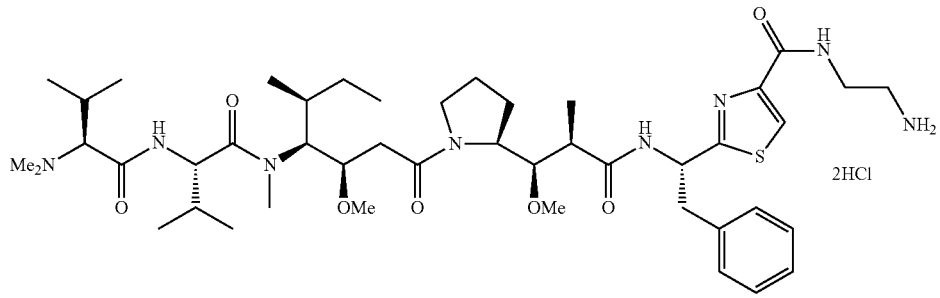 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)NCCN)cs1)OC)N(C)C(=O)[C@@H](NC(=O)[C@H](C(C)C)N(C)C)C(C)C]

The synthesis was performed by the same method as in Example 5 except that the compound of Reference Example 11 was used in place of the compound of Reference Example 8, to obtain the captioned compound (41 mg, 96% yield) (hereinafter, referred to as the compound of Reference Example 12) as a white solid.

$^1$H-NMR (400 MHz, CD$_3$OD) δ: 8.65 (1H, brs), [8.19 (0.5H, s), 8.16 (0.5H, s)], 7.32-7.16 (5H, m), 5.69-5.56 (1H, m), 4.80-4.63 (2H, m), 4.15-3.05 (14H, m), 3.33 (6H, s), 2.91 (6H, s), 2.51-1.38 (10H, m), 1.30-0.91 (21H, m), 0.85 (3H, t, J=7.1 Hz).

MS m/z (ESI) [M+H]$^+$: 871. (LC/MS-1)

Reference Example 13: Synthesis of tert-butyl (2-(2-((S)-1-(((2S,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)thiazole-4-carboxamido)ethyl)(methyl)carbamate

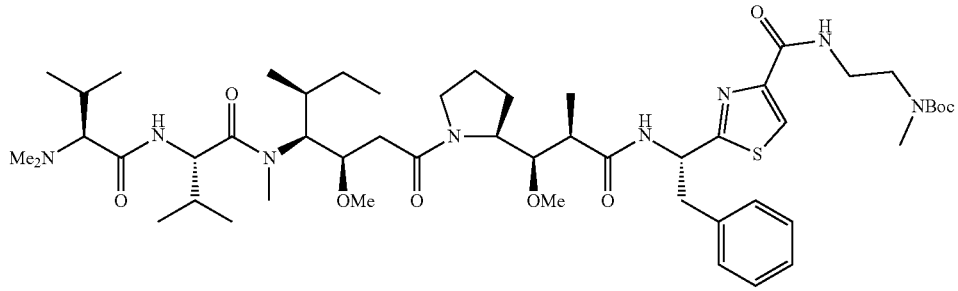 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)NCCN(C)C(=O)OC(C)(C)C)cs1)OC)N(C)C(=O)[C@@H](NC(=O)[C@H](C(C)C)N(C)C)C(C)C]

The synthesis was performed by the same method as in Reference Example 2 except that (2-aminoethyl)(methyl)carbamic acid tert-butyl ester was used in place of 2-(tritylthio)ethanamine, to obtain the captioned compound (32 mg, 40% yield) (hereinafter, referred to as the compound of Reference Example 13) as a white solid.

$^1$H-NMR (400 MHz, CDCl$_3$) δ: 7.94 (1H, s), 7.79 (1H, brs), 7.47 (1H, brs), 7.26-7.09 (5H, m), 6.89 (1H, d, J=9.1 Hz), 5.53-5.46 (1H, m), 4.82-4.74 (2H, m), 4.15-3.11 (11H, m), 3.33 (3H, s), 3.31 (3H, s), 3.03 (3H, s), 2.92 (3H, s), 2.47-2.34 (4H, m), 2.24 (6H, s), 2.12-1.94 (2H, m), 1.77-1.65 (4H, m), 1.43 (9H, s), 1.40-1.20 (1H, m), 1.12-0.78 (23H, m).

MS m/z (ESI) [M+H]$^+$: 985. (LC/MS-1)

Reference Example 14: Synthesis of 2-((S)-1-(((2S,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-(2-(methylamino)ethyl)thiazole-4-carboxamide dihydrochloride

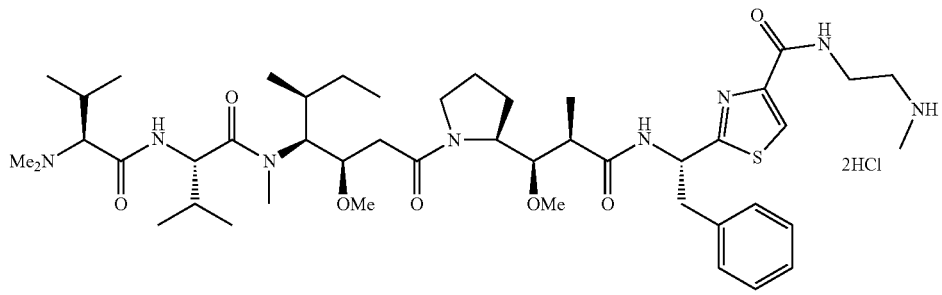 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)NCCNC)cs1)OC)N(C)C(=O)[C@@H](NC(=O)[C@H](C(C)C)N(C)C)C(C)C]

The synthesis was performed by the same method as in Example 5 except that the compound of Reference Example 13 was used in place of the compound of Reference Example 8, to obtain the captioned compound (25 mg, 88% yield) (hereinafter, referred to as the compound of Reference Example 14) as a white solid.

$^1$H-NMR (400 MHz, CD$_3$OD) δ: 8.63 (1H, brs), 8.22-8.14 (1H, m), 7.35-7.15 (5H, m), 5.70-5.52 (1H, m), 4.83-4.63 (2H, m), 4.17-3.04 (20H, m), 2.91 (3H, s), 2.90 (3H, s), 2.74 (3H, s), 2.51-1.98 (6H, m), 1.91-1.50 (4H, m), 1.42-0.80 (24H, m).

MS m/z (ESI) [M+H]$^+$: 885. (LC/MS-1)

Reference Example 15: Synthesis of 2-((S)-1-(((2S,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-(2-(3-(tritylthio)propanamido)ethyl)thiazole-4-carboxamide

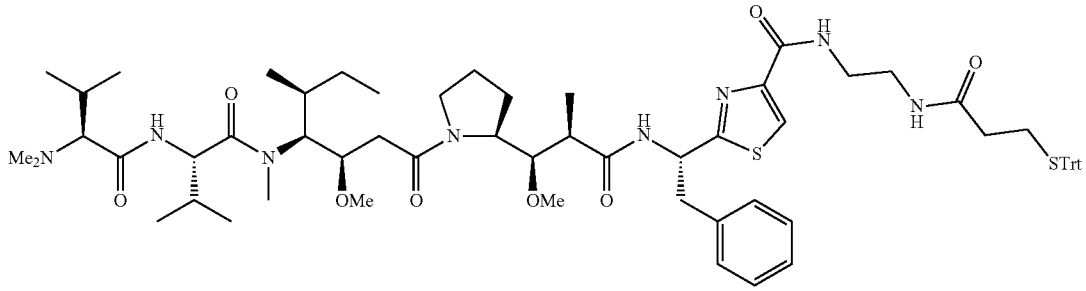

To a solution of 3-(tritylthio)propanoic acid (12 mg, 0.032 mmol) in DMF (0.50 mL), HATU (12 mg, 0.032 mmol), a solution of the compound of Reference Example 12 (20 mg, 0.021 mmol) in DMF (0.50 mL), and diisopropylethylamine (13 μL, 0.074 mmol) were added, and the mixture stirred at room temperature for one hour. To the obtained reaction solution, water was added, and the mixture extracted with ethyl acetate. The organic layer was washed with water and saturated brine, dried over anhydrous sodium sulfate, and then concentrated under vacuum. The residue was purified by silica gel column chromatography (methanol/chloroform=0/1→1/9) to obtain the captioned compound (20 mg, 77% yield) (hereinafter, referred to as the compound of Reference Example 15) as a white solid.

$^1$H-NMR (400 MHz, CDCl$_3$) δ: 7.91 (1H, s), 7.69 (1H, t, J=6.1 Hz), 7.46 (1H, brs), 7.42-7.10 (20H, m), 6.92 (1H, d, J=9.5 Hz), 6.16 (1H, brs), 5.51-5.45 (1H, m), 4.88-4.74 (2H, m), 4.13-4.09 (1H, m), 4.07-4.02 (1H, m), 3.87 (1H, d, J=7.7 Hz), 3.60-3.18 (8H, m), 3.33 (3H, s), 3.32 (3H, s), 3.04 (3H, s), 2.50-2.32 (6H, m), 2.25 (6H, s), 2.09-1.96 (4H, m), 1.90-1.63 (4H, m), 1.40-1.20 (1H, m), 1.10 (3H, d, J=7.2 Hz), 1.05-0.88 (17H, m), 0.81 (3H, t, J=7.2 Hz).

MS m/z (ESI) [M+H]$^+$: 1201. (LC/MS-1)

Reference Example 16: Synthesis of 2-((S)-1-(((2S, 3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-(2-(3-mercaptopropanamido)ethyl)thiazole-4-carboxamide

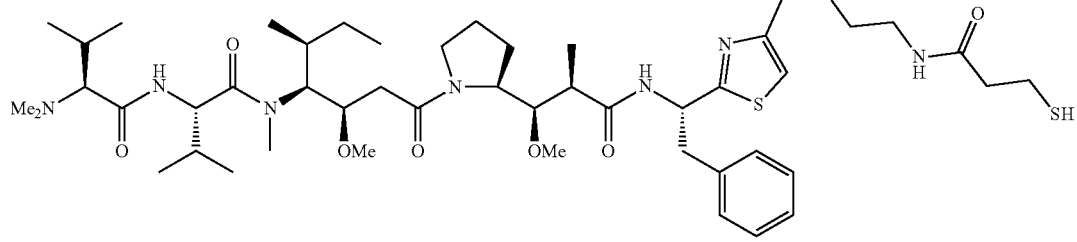

The synthesis was performed by the same method as in Example 1 except that the compound of Reference Example 15 was used in place of the compound of Reference Example 2, to obtain the captioned compound (7.3 mg, 89% yield) (hereinafter, referred to as the compound of Reference Example 16) as a white solid.

$^1$H-NMR (400 MHz, CDCl$_3$) δ: 7.97 (1H, s), 7.78 (1H, brs), 7.51 (1H, brs), 7.32-7.10 (5H, m), 7.00-6.85 (1H, m), 6.58 (1H, brs), 5.53-5.45 (1H, m), 4.82-4.74 (2H, m), 4.15-4.08 (1H, m), 4.06-4.00 (1H, m), 3.86 (1H, d, J=7.7 Hz), 3.64-3.18 (8H, m), 3.33 (3H, s), 3.32 (3H, s), 3.04 (3H, s), 2.82-2.75 (2H, m), 2.50 (2H, t, J=6.8 Hz), 2.48-2.37 (4H, m), 2.26 (6H, s), 2.12-1.92 (2H, m), 1.83-1.57 (4H, m), 1.27-1.19 (1H, m), 1.11-0.86 (20H, m), 0.81 (3H, t, J=7.2 Hz).

MS m/z (ESI) [M+H]$^+$: 959. (LC/MS-1)

Reference Example 17: Synthesis of tert-butyl N2-(((9H-fluorene-9-yl)methoxy)carbonyl)-N5-((S)-5-(tert-butoxy)-1,5-dioxo-1-((2-(tritylthio)ethyl)amino)pentan-2-yl)-L-glutaminate

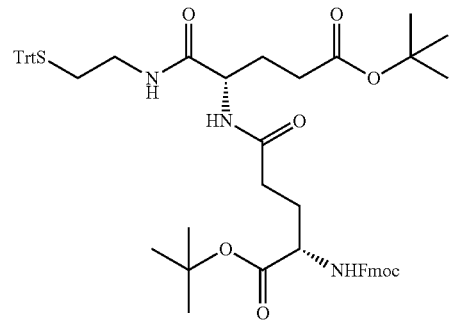

Tert-butyl (S)-4-((((9H-fluoren-9-yl)methoxy)carbonyl)amino)-5-oxo-5-((2-(tritylthio)ethyl)amino)pentanoate (1.5 g, 2.1 mmol) was dissolved in a solution of 20% by volume of diethylamine in tetrahydrofuran (hereinafter, THF) (20 ml), the mixture stirred overnight at room temperature, and then the reaction mixture concentrated under vacuum. To a solution of the obtained residue, HATU (942 mg, 2.5 mmol), and N-α-(9-fluorenylmethoxycarbonyl)-L-glutaminic acid a-t-butyl ester (878 mg, 2.1 mmol) in DMF (30 ml), diisopropylethylamine (320 mg, 2.5 mmol) was added, and the mixture stirred overnight at room temperature. After adding an excess amount of ethyl acetate, the mixture was washed with a saturated aqueous solution of ammonium chloride and saturated brine, the organic layer dehydrated over anhydrous sodium sulfate, and then concentrated under vacuum. The obtained residue was purified by silica gel column chromatography (n-hexane/ethyl acetate=10/1-+2/1) to obtain the captioned compound (1.81 g, 96% yield) (hereinafter referred to as the compound of Reference Example 17) as a white amorphous.

$^1$H-NMR (400 MHz, CDCl$_3$) δ: 7.76 (d, J=7.3 Hz, 2H), 7.61 (d, J=7.8 Hz, 2H), 7.40 (td, J=4.9, 2.9 Hz, 7H), 7.30 (ddt, J=19.7, 8.5, 3.3 Hz, 9H), 7.22-7.18 (m, 2H), 6.65 (d, J=6.4 Hz, 1H), 6.41 (s, 1H), 5.59 (d, J=8.2 Hz, 1H), 4.36 (dt, J=16.6, 6.1 Hz, 2H), 4.21 (t, J=6.9 Hz, 2H), 3.04 (dd, J=9.8, 6.2 Hz, 2H), 2.39 (dt, J=18.8, 6.6 Hz, 3H), 2.25 (dt, J=23.0, 6.6 Hz, 3H), 2.01 (t, J=6.9 Hz, 1H), 1.87 (t, J=6.6 Hz, 1H), 1.46 (s, 9H), 1.42 (s, 9H), 1.13 (dt, J=13.3, 5.7 Hz, 2H).

MS m/z (ESI) [M+Na]$^+$: 934. (LC/MS-2)

Reference Example 18: Synthesis of tert-butyl N5-((S)-5-(tert-butoxy)-1,5-dioxo-1-((2-(tritylthio)ethyl)amino)pentan-2-yl)-L-glutaminate

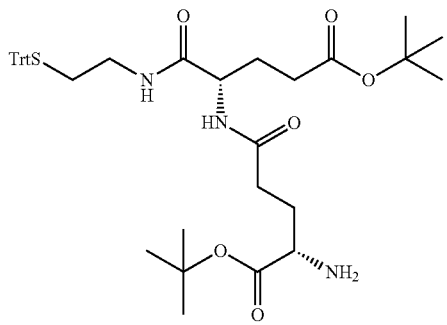

Reference Example 17 (480 mg, 0.53 mmol) was dissolved in a solution of 20% by volume of diethylamine in THF (5.0 ml), the mixture stirred overnight at room temperature, and then the reaction solution concentrated under vacuum. The obtained residue was purified by silica gel column chromatography (methanol/chloroform=0/1-,1/9) to obtain the captioned compound (284 mg, 78% yield) (hereinafter referred to as the compound of Reference Example 18) as a white amorphous.

$^1$H-NMR (400 MHz, CDCl$_3$) δ: 7.41 (t, J=4.5 Hz, 6H), 7.29 (dd, J=10.4, 5.0 Hz, 7H), 7.21 (dd, J=8.4, 6.1 Hz, 3H), 6.91 (s, 1H), 6.85 (d, J=7.2 Hz, 1H), 4.36-4.31 (m, 1H), 3.31-3.26 (m, 1H), 3.12-3.06 (m, 1H), 2.95 (dd, J=13.6, 6.3 Hz, 1H), 2.45-2.22 (m, 7H), 2.10-2.01 (m, 3H), 1.95-1.87 (m, 7H), 1.46 (s, 9H), 1.43 (d, J=3.6 Hz, 12H), 1.30-1.24 (m, 2H), 1.16 (t, J=7.0 Hz, 1H), 1.11 (t, J=7.2 Hz, 1H).

MS m/z (ESI) [M+H]$^+$: 690. (LC/MS-1)

Reference Example 19: Synthesis of tert-butyl N2-(4-(N-((2-amino-4-oxo-4,8-dihydropteridin-6-yl)methyl)-2,2,2-trifluoroacetamido)benzoyl)-N5-((S)-5-(tert-butoxy)-1,5-dioxo-1-((2-(tritylthio)ethyl)amino)pentan-2-yl)-L-glutaminate

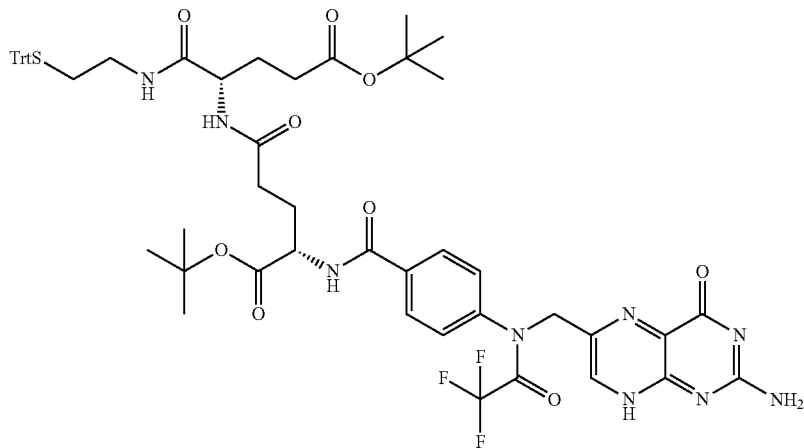

To a solution of 4-(N-((2-amino-4-oxo-4,8-dihydropteridin-6-yl)methyl)-2,2,2-trifluoroacetamido)benzoic acid (177 mg, 0.43 mmol) and HATU (188 mg, 0.50 mmol) in DMF/dimethyl sulfoxide (hereinafter, DMSO) (10 ml/1.0 ml), diisopropylethylamine (75 mg, 0.58 mmol) was added, and the mixture stirred at room temperature for five minutes. To the obtained reaction solution, a solution of Reference Example 18 (285 mg, 0.41 mmol) in DMF (5.0 ml) was added, and the mixture stirred overnight at room temperature. After adding an excess amount of 1% by volume of methanol in chloroform, the mixture was washed twice with a saturated aqueous solution of ammonium chloride and saturated brine, and the organic layer dehydrated over anhydrous sodium sulfate and then concentrated under vacuum. The obtained residue was purified by silica gel column chromatography (methanol/chloroform=0/1→1/5) to obtain the captioned compound (270 mg, 61% yield) (hereinafter, referred to as the compound of Reference Example 19) as a yellow solid.

$^1$H-NMR (400 MHz, CD$_3$OD) δ: 8.67 (s, 1H), 7.89 (d, J=8.6 Hz, 3H), 7.55 (d, J=8.6 Hz, 2H), 7.35 (dd, J=5.2, 3.4 Hz, 6H), 7.27-7.23 (m, 6H), 7.18 (td, J=5.7, 2.9 Hz, 3H), 4.40 (dd, J=9.5, 4.5 Hz, 1H), 4.28 (dd, J=8.4, 5.7 Hz, 1H), 3.08 (dd, J=13.4, 6.6 Hz, 1H), 2.99 (q, J=6.9 Hz, 1H), 2.40 (dd, J=10.9, 4.5 Hz, 2H), 2.28 (dt, J=17.2, 5.0 Hz, 4H), 2.05-1.98 (m, 2H), 1.82 (dd, J=13.8, 8.4 Hz, 1H), 1.46 (s, 9H), 1.39 (s, 9H), 1.28 (s, 1H).

MS m/z (ESI) [M−H]$^-$: 1079. (LC/MS-1)

Reference Example 20: Synthesis of N2-(4-(((2-amino-4-oxo-4,8-dihydropteridin-6-yl)methyl)amino)benzoyl)-N5-((S)-4-(carboxy)-1-((2-(mercaptoethyl)amino)-1-oxobutan-2-yl)-L-glutamine

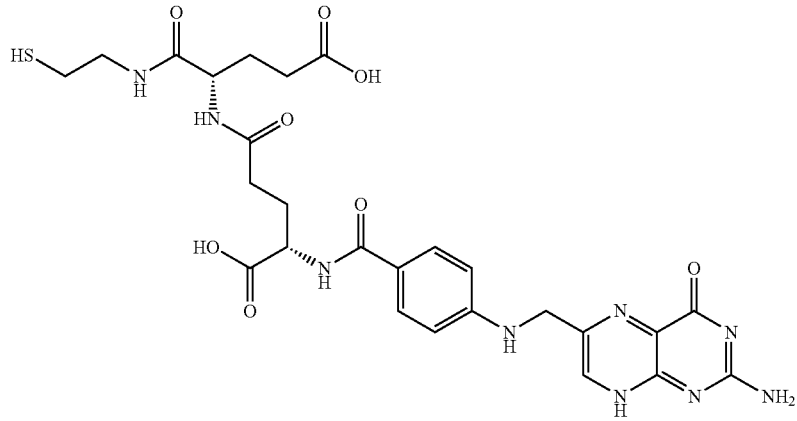 [SMILES: Nc1nc2[nH]cc(CNc3ccc(C(=O)N[C@@H](CCC(=O)N[C@@H](CCC(=O)O)C(=O)NCCS)C(=O)O)cc3)nc-2c(=O)n1]

To a suspension of Reference Example 19 (120 mg, 0.11 mmol) in dichloromethane (5.0 ml), a solution of 7 N ammonia-methanol (5.0 ml) was added to obtain a uniform solution, and the uniform solution stirred overnight at room temperature. To a solid that was obtained by evaporation under vacuum of the solvent of the uniform solution, an excess amount of diethyl ether was added and washed, and the precipitated solid collected by filtration (intermediate 1, 105 mg). To the intermediate 1 (105 mg), TFA/triisopropylsilane/H$_2$O/ethanediol (92.5/2.5/2.5/2.5% by volume) (10 ml) was added, and the mixture stirred overnight at room temperature. To the residue obtained by evaporation under vacuum of the solvent of the mixture, an excess amount of diethyl ether was added and stirred, the precipitation formed collected by filtration, and the obtained solid washed with dichloromethane to obtain the captioned compound (65 mg, 92% yield, 80% purity) (hereinafter, referred to as the compound of Reference Example 20) as a green-yellow solid.

$^1$H-NMR (DMSO-d$_6$) δ: 8.66 (s, 1H), 8.23 (d, J=7.7 Hz, 1H), 8.05 (q, J=6.2 Hz, 2H), 7.66 (d, J=8.6 Hz, 2H), 6.64 (d, J=8.6 Hz, 2H), 4.50 (s, 2H), 4.28 (t, J=10.9 Hz, 1H), 4.18 (dd, J=13.1, 8.2 Hz, 1H), 3.23-3.13 (m, 2H), 2.35 (t, J=8.2 Hz, 1H), 2.22 (dd, J=16.5, 7.5 Hz, 5H), 2.04 (d, J=6.8 Hz, 2H), 1.90 (dd, J=24.7, 10.2 Hz, 3H), 1.70 (t, J=7.2 Hz, 1H), 1.25 (s, 1H).

MS m/z (ESI) [M+H]$^+$: 630. (LC/MS-2)

t$_R$=120.21 min. (HPLC)

Reference Example 21: Synthesis of 4-(2-(2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)thiazole-4-carboxamido)ethyl)phenyl (2-((2-((tert-butoxycarbonyl)(methyl)amino)ethyl)disulfanyl)ethyl)(methyl)carbamate

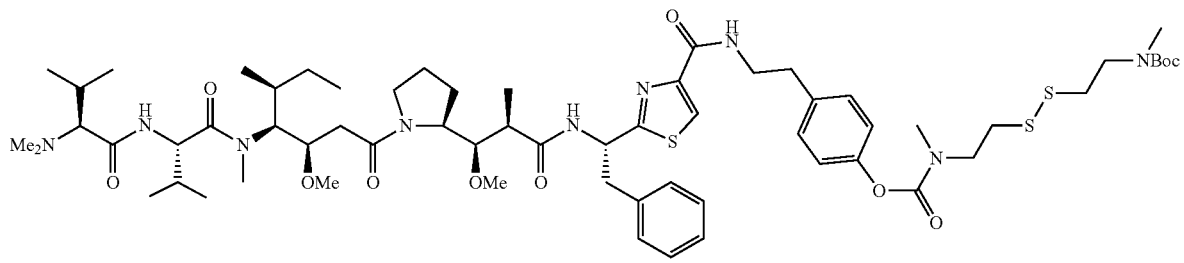 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)NCCc2ccc(OC(=O)N(C)CCSSCCN(C)C(=O)OC(C)(C)C)cc2)cs1)OC)N(C)C(=O)[C@@H](NC(=O)[C@H](C(C)C)N(C)C)C(C)C]

A solution of triphosgen (17 mg, 0.06 mmol) in dichloromethane (1.0 ml) was cooled on ice, and dehydrated pyridine (25 mg, 0.31 mmol) added thereto, and then the mixture stirred for 20 minutes. To the solution, a solution of tert-butyl methyl(2-((2-(methylamino)ethyl)disulfanyl)ethyl)carbamate (15 mg, 0.05 mmol) in dichloromethane (2.0 ml) was added dropwise slowly, and the mixture returned to room temperature and stirred for one hour. To the obtained solution, an excess amount of dichloromethane was added, the mixture washed three times with water, and then the organic layer dehydrated over anhydrous sodium sulfate and then concentrated under vacuum. The obtained residue (7.5 mg) was dissolved in dehydrated pyridine (1.0 ml), the mixture cooled on ice, and a solution of the compound of Example 11 (25 mg, 0.03 mmol) in dehydrated pyridine (3.0 ml) then added thereto, and the mixture stirred overnight while being allowed to room temperature. After adding an excess amount of ethyl acetate, the resultant solution was washed three times with water and once with a saturated aqueous solution of ammonium chloride and saturated brine, respectively, and the organic layer was dehydrated over anhydrous sodium sulfate and then concentrated under vacuum. The obtained residue was purified by amine silica gel column chromatography (methanol/chloroform=0/1→1/20) to obtain the captioned compound (25 mg, 76% yield) (hereinafter, referred to as the compound of Reference Example 21) as a white amorphous.

$^1$H-NMR (400 MHz, CDCl$_3$) δ: 7.96 (1H, s), 7.41-7.30 (2H, m), 7.27-7.10 (5H, m), 7.06 (2H, d, J=8.2 Hz), 5.49-5.44 (1H, m), 4.85-4.77 (2H, m), 4.13-3.64 (9H, m), 3.60-3.29 (15H, m), 3.13 (3H, s), 3.03 (3H, s), 2.51-2.30 (4H, m), 2.25 (6H, s), 2.17-1.98 (2H, m), 1.78 (12H, s), 1.11-0.88 (24H, m), 0.82 (5H, m).

MS m/z (ESI) [M-Boc]$^{2+}$: 577. (LC/MS-1)

Reference Example 22: Synthesis of 4-(2-(2-((S)-1-((2R,3R)-3-((S)-1-((3R,4R,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)thiazole-4-carboxamido)ethyl)phenyl (50-(2,5-dioxo-2,5-dihydro-1H-pyrrol-1-yl)-7-methyl-8,48-dioxo-11,14,17,20,23,26,29,32,35,38,41,44-dodecaoxa-3,4-dithia-7,47-diazapentacontyl)(methyl)carbamate

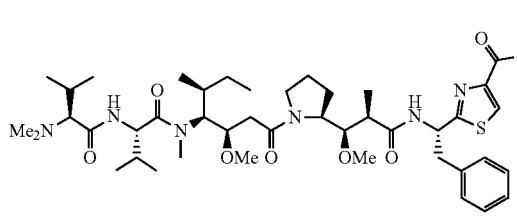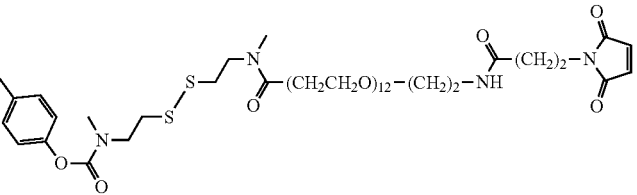

To a solution of Reference Example 21 (20 mg, 0.02 mmol) in dichloromethane (1.0 ml), 4 N hydrogen chloride-dioxane solution (0.5 ml) was added, and the mixture stirred at room temperature for one hour. After the reaction solution was concentrated under vacuum, the obtained solution was dried under vacuum. To the obtained residue, HATU (7.3 mg, 0.02 mmol) and DMF (0.5 ml) were added. To the reaction solution, a solution of 1-(2,5-dioxo-2,5-dihydro-1H-pyrrol-1-yl)-3-oxo-7,10,13,16,19,22,25,28,31,34,37,40-dodecaoxa-4-azatritetracontan-43-oic acid (12 mg, 0.02 mmol) in dichloromethane (1.0 ml), and diisopropylethylamine (10 μl) were added, and the mixture stirred overnight at room temperature. The obtained reaction solution was concentrated under vacuum, the obtained residue was purified by silica gel column chromatography (methanol/chloroform=0/1→1/5) to obtain the captioned compound (15 mg, 40% yield) (hereinafter referred to as the compound of Reference Example 22) as an oily substance.

MS m/z (ESI) [M+H]$^{3+}$: 635. (LC/MS-1)

$t_R$=170.11 min. (HPLC)

Example 12: Synthesis of N2-(4-(((2-amino-4-oxo-4,8-dihydropteridin-6-yl)methyl)amino)benzoyl)-N5-((2S)-4-carboxy-1-((2-((1-(1-(4-(2-(2-((S)-1-((2R,3R)-3-((S)-1-((3R,4R,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)thiazol-4-carboxamido)ethyl)phenoxy)-2,9-dimethyl-1,10,50-trioxo-13,16,19,22,25,28,31,34,37,40,43,46-dodecaoxa-5,6-dithia-2,9,49-triazadopentacontan-52-yl)-2,5-dioxopyrrolidin-3-yl)thio)ethyl)amino)-1-oxobutan-2-yl)-L-glutamine

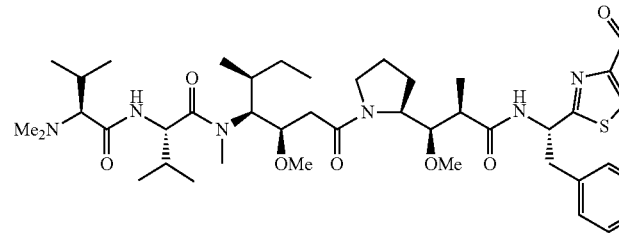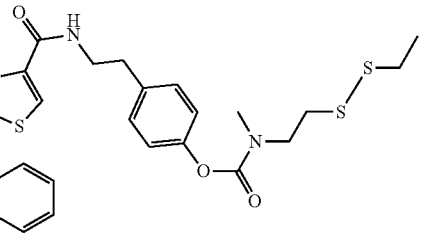

-continued

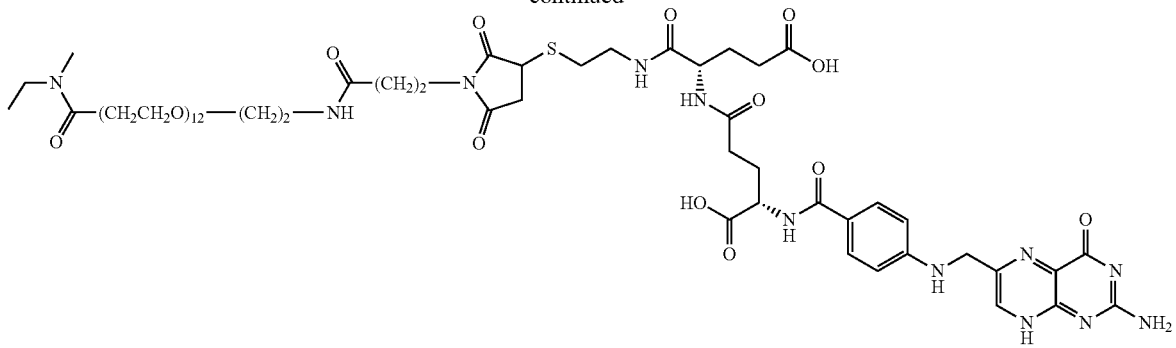

To a solution of Reference Example 22 (6.8 mg, 0.003 mmol) in acetonitrile/methanol (1.0 ml/0.5 ml), a solution of Reference Example 20 (3.0 mg, 0.005 mmol) in DMSO (1.0 ml), and a pH 7.2 phosphate buffer (hereinafter, PBS) (50 mM, 1.0 ml) were added, and the mixture stirred overnight at room temperature. The obtained reaction mixture was purified by reversed-phase ODS column to obtain the captioned compound (6.0 mg, 67% yield) (hereinafter, referred to as the compound of Example 12) as an oily substance.

MS m/z (ESI) $[M-H]^{2-}$: 1266. (LC/MS-1)
HRMS m/z (ESI) $[M-H]^-$: 2532.1754.
Calculated exact mass of $C_{118}H_{180}N_{20}O_{33}S_4$: 2532.1832
$t_R$=160.40 min. (HPLC)

Reference Example 23: Synthesis of tert-butyl (2-((2-(2-((S)-1-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-methylthiazole-4-carboxamido)ethyl)disulfanyl)ethyl)(methyl)carbamate

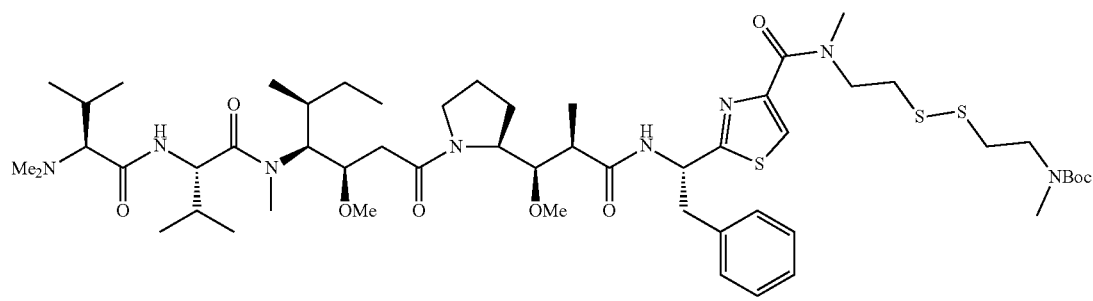 [SMILES: CC[C@H](C)[C@@H]([C@@H](CC(=O)N1CCC[C@H]1[C@H](OC)[C@@H](C)C(=O)N[C@@H](Cc1ccccc1)c1nc(C(=O)N(C)CCSSCCN(C)C(=O)OC(C)(C)C)cs1)OC)N(C)C(=O)[C@@H](NC(=O)[C@H](C(C)C)N(C)C)C(C)C]

The synthesis was performed by the same method as in Reference Example 2 except that tert-butyl methyl(2-((2-(methylamino)ethyl)disulfanyl)ethyl)carbamate was used in place of 2-(tritylthio)ethanamine, to obtain the captioned compound (26 mg, 92% yield) (hereinafter, referred to as the compound of Reference Example 23) as a white solid.

$^1$H-NMR (400 MHz, CDCl$_3$) δ:8.01 (1H, s), 7.87 (1H, brs), 7.46 (1H, brs), 7.26-7.15 (5H, m), 6.90 (1H, d, J=8.2 Hz), 5.56 (1H, brs), 4.81-4.77 (2H, m), 4.12 (1H, brs), 4.05 (1H, brs), 3.97 (1H, brs), 3.88 (1H, d, J=7.7 Hz), 3.80 (2H, m), 3.51-3.16 (4H, m), 3.33 (3H, s), 3.32 (3H, s), 3.13 (3H, s), 3.04 (3H, s), 2.96 (3H, s), 2.81-2.74 (2H, m), 2.89 (3H, s), 2.46-2.34 (3H, m), 2.25 (6H, s), 2.12-1.97 (2H, m), 1.66 (15H, d, J=8.8 Hz), 1.45 (9H, t, J=8.6 Hz), 1.10 (2H, d, J=7.2 Hz), 1.05-0.90 (12H, m), 0.82 (3H, t, J=7.5 Hz).

MS m/z (ESI) $[M+H]^+$: 1092. (LC/MS-1)

Reference Example 24: Synthesis of 2-((S)-1-((2R, 3R)-3-((S)-1-((3R,4R,5S)-4-((S)-2-((S)-2-(dimethyl-amino)-3-methylbutanamido)-N,3-dimethylbutana-mido)-3-methoxy-5-methylheptanoyl)pyrrolidin-2-yl)-3-methoxy-2-methylpropanamido)-2-phenylethyl)-N-(50-(2,5-dioxo-2,5-dihydro-1H-pyrrol-1-yl)-7-methyl-8,48-dioxo-11,14,17,20,23,26,29,32,35,38,41,44-dodecaoxa-3,4-dithia-7,47-diazapentacontyl)-N-methylthiazole-4-carboxamide

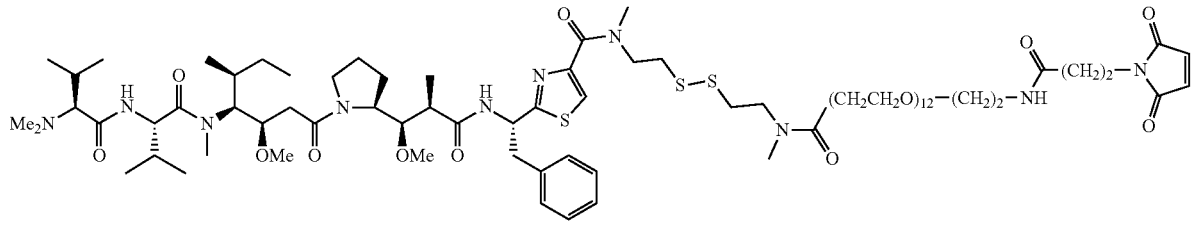

The synthesis was performed by the same method as in Reference Example 22 except that Reference Example 23 was used in place of Reference Example 21, to obtain the captioned compound (17 mg, 31% yield) (hereinafter, referred to as the compound of Reference Example 24) as an oily substance.

MS m/z (ESI) $[M+H]^{2+}$: 871. (LC/MS-1)
$t_R$=160.66 min. (HPLC)

Example 13: Synthesis of N2-(4-(((2-amino-4-oxo-4,8-dihydropteridin-6-yl)methyl)amino)benzoyl)-N5-((2S)-4-carboxy-1-((2-((1-(1-(2-((S)-1-((2R,3R)-3-((S)-1-((3R,4R,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)thiazol-4-yl)-2,9-dimethyl-1,10,50-trioxo-13,16,19,22,25,28,31,34,37,40,43,46-dodecaoxa-5,6-dithia-2,9,49-triazadopentacontan-52-yl)-2,5-dioxopyrrolidin-3-yl)thio)ethyl)amino)-1-oxobutan-2-yl)-L-glutamine

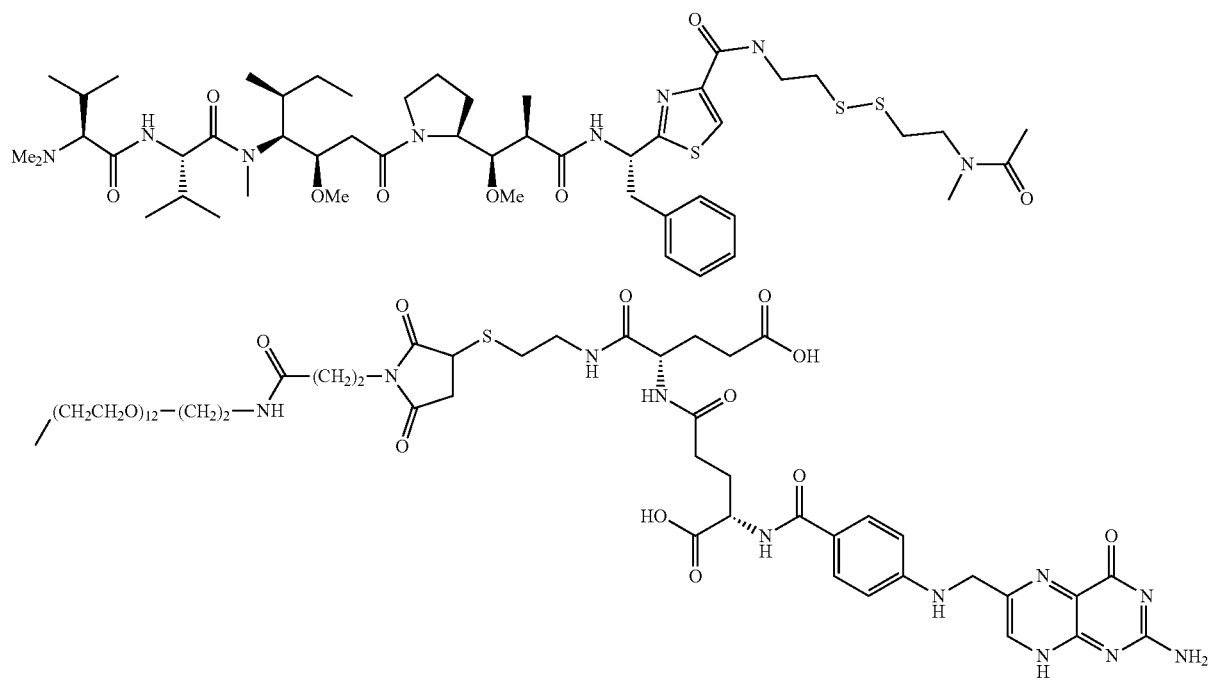

The synthesis was performed by the same method as in Example 12 except that Reference Example 24 was used in place of Reference Example 22, to obtain the captioned compound (8.4 mg, 71% yield) (hereinafter, referred to as the compound of Example 13) as an oily substance.

MS m/z (ESI) [M–H]$^{2-}$: 1184. (LC/MS-1)
HRMS m/z (ESI) [M–H]$^-$: 2369.1162.
Calculated exact mass of $C_{109}H_{171}N_{19}O_{31}S_4$: 2369.1198.
$t_R$=15.85 min. (HPLC)
Analytical conditions for LC/MS-1 are as follows:
(LC/MS-1)
Liquid chromatograph system: LC1200 (Agilent Technologies)
Mass spectrometry: 6130A (Agilent Technologies)
Analytical Conditions
Column: Rapid Resolution HT Cartridge
Mobile phase A: 0.1% by volume of formic acid in distilled water, for HPLC
Mobile phase B: 0.1% by volume formic acid in acetonitrile, for HPLC
Gradient conditions: mobile phase B, % by volume
0-1.5 min: 20%-95%
1.5-3.0 min: 95%
Flow rate: 0.5 mL/min
Injection amount: 2.0 µL
Column temperature: 40° C.
Analytical conditions for LC/MS-2 are as follows:
(LC/MS-2)
Liquid chromatograph system: LC1260 Infinity II (Agilent Technologies)
Mass spectrometer: 6130B (Agilent Technologies)
Analytical Conditions
Column: Rapid Resolution HT Cartridge
Mobile phase A: 0.1% by volume of formic acid in distilled water, for HPLC
Mobile phase B: 0.1% by volume of formic acid in acetonitrile, for HPLC
Gradient conditions: mobile phase B, % by volume
0-1.5 min: 20%-95%
1.5-3.0 min: 95%
Flow rate: 0.5 mL/min
Injection amount: 2.0 µL
Column temperature: 40° C.
Analytical conditions for HRMS are as follows:
Liquid chromatograph system: NexeraX2 (SHIMADZU CORPORATION)
Mass spectrometer: LCMS-IT-TOF Mass Spectrometer (SHIMADZU CORPORATION)
Analytical Conditions
Mobile phase: methanol
Flow rate: 0.1 mL/min
Injection amount: 2.0 µL
Conditions for purification by an ODS column are as follows:
Conditions for purification by an ODS column
Column: YAMAZEN Hi-Flash column ODS (column size M)
Flow rate: 10 ml/min
Column temperature: room temperature
Detection wavelength: 254 nm
Mobile phase A: 0.05% by volume of TFA in $H_2O$
Mobile phase B: 0.05% by volume of TFA in $CH_3CN$
Gradient: mobile phase B, % by volume
0-5 min: 5.0%
5-20 min: increased from 5% to 95%
20-25 min: 95%

Analytical conditions for HPLC are as follows:
(HPLC)
Column: COSMOSIL 5C18-AR-III, 4.6 mm I.D.×150 mm
Flow rate: 1.0 ml/min
Column temperature: 40° C.
Detection wavelength: 254 nm
Mobile phase A: 0.05% by volume of TFA in $H_2O$
Mobile phase B: 0.05% by volume of TFA in $CH_3CN$
Gradient: mobile phase B, % by volume
0-5 min: 5.0%
5-20 min: increased from 5% to 95%
20-25 min: 95%

Example 14: In Vitro Evaluation for the Cytotoxicity of the Peptide Derivative (I)

Cytotoxicity, on SKOV-3 cells, A549 cells, and L1210 cells, of the compounds of Examples 1 to 11, the compound of Reference Example 1, the compound of Reference Example 12, the compound of Reference Example 14, the compound of Reference Example 16, and 2-((S)-1-(((2S,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-2-phenylethyl)-N-ethylthiazole-4-carboxamide (hereinafter, referred to as the compound of Comparative Example) was measured using MTS method.

The cytotoxicity of each test substance is shown in Table 5. In Table 5, $EC_{50}$ means 50% effective concentration and represents a concentration of a drug at which 50% of maximal response from the minimum value of pharmacological action exhibited by the drug is indicated; and SKOV-3 represents SKOV-3 cells, A549 represents A549 cell, and L1210 represents L1210 cell.

TABLE 5

| Test Substance | $EC_{50}$(nmol/L) | | |
| --- | --- | --- | --- |
| | SKOV-3 | A549 | L1210 |
| Compound of Example 1 | 0.44 | 1.93 | 31.4 |
| Compound of Example 2 | 0.13 | 6.88 | 14.2 |
| Compound of Example 3 | 1.05 | 1.22 | 6.96 |
| Compound of Example 4 | 0.85 | 0.83 | 28.7 |
| Compound of Example 5 | 0.56 | 0.81 | 11.7 |
| Compound of Example 6 | 0.22 | 1.94 | 17.23 |
| Compound of Example 7 | 4.67 | 1.74 | 28.4 |
| Compound of Example 8 | 0.09 | 1.75 | 4.74 |
| Compound of Example 9 | 1.50 | 1.64 | 8.52 |
| Compound of Example 10 | 0.27 | 1.08 | 4.05 |
| Compound of Example 11 | 0.37 | 1.31 | 5.61 |
| Compound of Reference Example 1 | >10 | >10 | >50 |
| Compound of Reference Example 12 | >10 | >10 | >50 |
| Compound of Reference Example 14 | >10 | 9.85 | 26.8 |
| Compound of Reference Example 16 | >10 | >10 | >50 |
| Compound of Comparative Example | 0.55 | 0.74 | 6.51 |

As seen from the results in Table 5, the peptide derivatives (I) or the pharmaceutically acceptable salts thereof were indicated to have high cytotoxicity on a plurality of cancer cells.

Example 15: Parallel Artificial Membrane Permeation Assay (PAMPA) of the Peptide Derivatives (I)

The artificial membrane permeation of the compounds of Examples 1 to 11, the compound of Reference Example 1, the compound of Reference Example 12, the compound of Reference Example 14, the Compound of Reference Example 16, and the Compound of Comparative Example was Evaluated by Using Pre-Coated PAMPA PlateSystem (Corning)

The test substance was dissolved in DMSO to give a 10 mmol/L concentration, then the mixture was diluted in PBS containing 20% of methanol to give a 200 μmol/L concentration, and the obtained solution was used as a standard solution. A frozen-stored, Pre-coated PAMPA Plate System was allowed to stand at room temperature for thirty minutes or more. Subsequently, 320 μL of the standard solution was added to a Donor side plate of Pre-coated PAMPA Plate System, and 200 μL of the PBS containing 20% of methanol was added to an Acceptor side plate. Both of the plates were set for the system, and the plates allowed to stand at room temperature for five hours. The reaction liquid in each well of the Donor side and Acceptor side plates was subjected to LC/MS analysis (hereinafter, LC/MS-3), and the concentration of the compounds in each well calculated.

Analytical conditions for LC/MS-3 are as follows:
Liquid chromatograph system: Waters Acquity UPLC (Waters)
Mass spectrometer: Waters SQD Detector (Waters)
Column: Ascentis Express C18, 2.7 μm, 2.1 mm ID×20 mm (Sigma-Aldrich)
Mobile phase A: 0.1% by volume of formic acid aqueous solution
Mobile phase B: acetonitrile
Flow rate: 0.6 mL/min
Gradient: mobile phase B, % by volume
0.0-2.0 min: 3.0→100%
2.0-2.4 min: 100%
2.4-2.5 min: 100→3.0%

Using the obtained concentration of the compounds in the reaction liquid in each well, the membrane permeability coefficients (Pe) (cm/s) were calculated by the following formula:

$$C_{equilibrium} = (CD \times VD - CA \times VA)/(VD - VA)$$

$$Pe = [-\ln(1 - CA/C_{equilibrium})]/S \times (1/VD + 1/VA) \times t$$

$C_{equilibrium}$: Equilibrium concentration of the wells in the Donor side and Acceptor side plates
CD: Concentration after five hours of the wells in the Donor side plate (mmol/L)
VD: Volume of the standard solution added to the wells in the Donor side plate (0.32 mL)
CA: Concentration after five hours of the wells in the Acceptor side plate (mmol/L)
VA: Volume of the PBS containing 20% of methanol added to the wells in the Acceptor side plate (0.2 mL)
S: Surface of the membrane (0.3 cm$^2$)
t: Standing time 18,000 s (=5 hrs).

The artificial membrane permeation of each test substance is shown in Table 6.

TABLE 6

| Test Substance | Membrane Permeability Coefficient ($10^{-6}$ cm/s) |
| --- | --- |
| Compound of Example 1 | 1.15 |
| Compound of Example 2 | 0.005 |
| Compound of Example 3 | 1.14 |
| Compound of Example 4 | 0.01 |
| Compound of Example 5 | 0.01 |
| Compound of Example 6 | N.D. |
| Compound of Example 7 | 0.02 |
| Compound of Example 8 | 0.04 |
| Compound of Example 9 | 0.08 |
| Compound of Example 10 | 0.30 |
| Compound of Example 11 | 0.36 |
| Compound of Reference Example 1 | 0.01 |
| Compound of Reference Example 12 | 0.01 |
| Compound of Reference Example 14 | 0.004 |
| Compound of Reference Example 16 | N.D. |
| Compound of Comparative Example | 1.68 |

In Table 6, N. D. means that the membrane permeability coefficient was not able to be calculated due to the concentration of the well in the Acceptor side plate less than lower limit of determinate quantity.

Example 16: In Vitro Evaluation for the Cytotoxicity of the Conjugate Including the Peptide Derivative (I)

The compound of Example 12 and the compound of Example 13 were measured for cytotoxicity thereof on SKOV-3 cells, A549 cells, and L1210 cells by using MTS method.

The compound of Example 12 is a conjugate that is obtained by conjugating folate as a targeting ligand with the prodrug of the compound of Example 11 by an appropriate method.

An evaluation method of the compound of Example 12 is as follows: To each cell culturing in a medium that is absent of folate, the compound of Example 12 was treated for two hours, and then the cells transferred to a fresh medium absent of the compound and continuously maintained and cultured for 48 hours. Surviving cells after 48 hours were counted by using MTS method.

The compound of Example 13 is a conjugate obtained by conjugating folate as a targeting ligand with the prodrug of the compound of Example 3 by an appropriate method.

An evaluation method of the compound of Example 13 is as follows: To each cell culturing in a medium that is absent of folate, the compound of Example 13 was treated for six hours, and then the cells transferred to a fresh medium absent of the compound and continuously maintained and cultured for 48 hours. Surviving cells after 48 hours were counted by using MTS method.

It has been reported that SKOV-3 cells and L1210 cells express folate acceptors in medium to high expression level on their cell surface. It has been reported that A549 cells express folate acceptors in low expression level or undetectable level on its cell surface (Analytical Biochemistry, (2005), 338: pp. 284-293; Molecular Cancer Therapeutics, (2015), 14: pp. 1605 to 13).

The cytotoxicity of each test substance is shown in Table 7. In Table 7, $EC_{50}$ means 50% effective concentration and represents a concentration of a drug at which 50% of maximal response from the minimum value, of pharmacological action exhibited by the drug is indicated; and SKOV-3 represents SKOV-3 cells, A549 represents A549 cell, and L1210 represents L1210 cell.

TABLE 7

| Test Substance | EC$_{50}$ (nmol/L) | | |
|---|---|---|---|
| | SKOV-3 | A549 | L1210 |
| Compound of Example 12 | 2.00 | >200 | 17.8 |
| Compound of Example 13 | 19.4 | >300 | 36.0 |

As seen from the results in Table 7, the composites including the peptide derivatives (I) or the pharmaceutically acceptable salts thereof were indicated to have high cytotoxicity selectively on cancer cells on which the folate receptors express on the cell surface.

Each peptide derivative (I) has various functional groups at its C-terminus. Thus, it was indicated that the peptide derivative (I) or a prodrug thereof can be conjugated with a targeting ligand or a polymer by an appropriate method to transform into a conjugate.

Furthermore, it was indicated that the conjugate obtained by the conjugation of the peptide derivative (I) or a prodrug thereof and a targeting ligand by an appropriate method has high cytotoxicity selectively on certain cells with an effect by the targeting ligand.

INDUSTRIAL APPLICABILITY

Our peptide derivatives (I) or pharmaceutically acceptable salts thereof have high cytotoxicity and therefore can be used as cytotoxic agents. Furthermore, the peptide derivatives (I) have various functional groups at C-terminus. Therefore, the peptide derivative (I) or a prodrug thereof, and a targeting ligand or a polymer can be conjugated. The resultant conjugates or pharmaceutically acceptable salts thereof can be used as cytotoxic agents.

The invention claimed is:

1. A peptide derivative represented by Formula (I) or a pharmaceutically acceptable salt thereof:

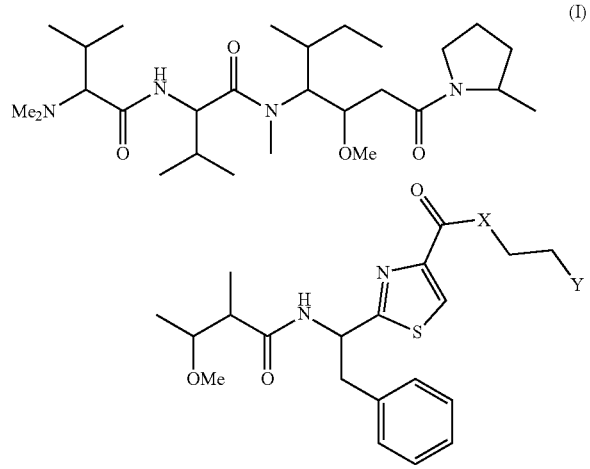

(I)

wherein X represents an oxygen atom or NR, Y represents NH$_2$, N(Me)H, SH, OH, or phenyl in which any one of hydrogen atoms is replaced by NH$_2$ or OH, and R represents a hydrogen atom or C$_1$-C$_3$ alkyl, provided that the derivative where X is NH, and Y is NH$_2$, and the derivative where X is NH, and Y is N(Me)H are excluded.

2. The peptide derivative or the pharmaceutically acceptable salt thereof according to claim 1, wherein X is an oxygen atom.

3. The peptide derivative or the pharmaceutically acceptable salt thereof according to claim 2, wherein Y is NH$_2$, N(Me)H, SH, or OH.

4. The peptide derivative or the pharmaceutically acceptable salt thereof according to claim 1, wherein X is NR.

5. The peptide derivative or the pharmaceutically acceptable salt thereof according to claim 4, wherein R is C$_1$-C$_3$ alkyl.

6. The peptide derivative or the pharmaceutically acceptable salt thereof according to claim 5, wherein R is methyl.

7. A conjugate or a pharmaceutically acceptable salt thereof, comprising: the peptide derivative according to claim 1 and a targeting ligand or a polymer.

8. A cytotoxic agent, comprising: as an active ingredient, the peptide derivative or the pharmaceutically acceptable salt thereof according to claim 1.

9. A cytotoxic agent, comprising: as an active ingredient, the conjugate or the pharmaceutically acceptable salt thereof according to claim 7.

10. A conjugate or a pharmaceutically acceptable salt thereof, comprising: the peptide derivative according to claim 2 and a targeting ligand or a polymer.

11. A conjugate or a pharmaceutically acceptable salt thereof, comprising: the peptide derivative according to claim 3 and a targeting ligand or a polymer.

12. A conjugate or a pharmaceutically acceptable salt thereof, comprising: the peptide derivative according to claim 4 and a targeting ligand or a polymer.

13. A conjugate or a pharmaceutically acceptable salt thereof, comprising: the peptide derivative according to claim 5 and a targeting ligand or a polymer.

14. A conjugate or a pharmaceutically acceptable salt thereof, comprising: the peptide derivative according to claim 6 and a targeting ligand or a polymer.

15. A cytotoxic agent, comprising: as an active ingredient, the peptide derivative or the pharmaceutically acceptable salt thereof according to claim 2.

16. A cytotoxic agent, comprising: as an active ingredient, the peptide derivative or the pharmaceutically acceptable salt thereof according to claim 3.

17. A cytotoxic agent, comprising: as an active ingredient, the peptide derivative or the pharmaceutically acceptable salt thereof according to claim 4.

18. A cytotoxic agent, comprising: as an active ingredient, the peptide derivative or the pharmaceutically acceptable salt thereof according to claim 5.

19. A cytotoxic agent, comprising: as an active ingredient, the peptide derivative or the pharmaceutically acceptable salt thereof according to claim 6.

* * * * *

UNITED STATES PATENT AND TRADEMARK OFFICE
CERTIFICATE OF CORRECTION

PATENT NO. : 10,792,365 B2  
APPLICATION NO. : 16/084994  
DATED : October 6, 2020  
INVENTOR(S) : Nisho et al.

It is certified that error appears in the above-identified patent and that said Letters Patent is hereby corrected as shown below:

In the Claims

In Column 119, at Line 40, please change Formula (I) to the following Formula (I):

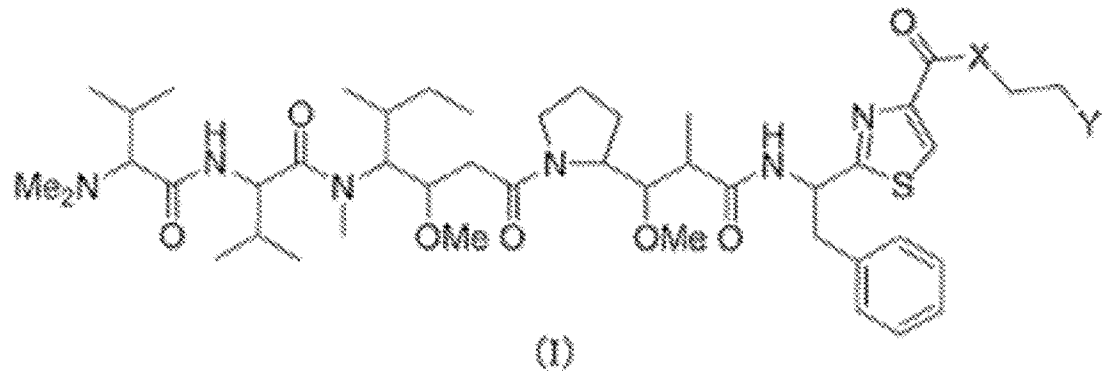

Signed and Sealed this  
Seventeenth Day of August, 2021

Drew Hirshfeld  
*Performing the Functions and Duties of the  
Under Secretary of Commerce for Intellectual Property and  
Director of the United States Patent and Trademark Office*